US011254919B2

(12) United States Patent
Hendriksen et al.

(10) Patent No.: US 11,254,919 B2
(45) Date of Patent: Feb. 22, 2022

(54) POLYNUCLEOTIDE ENCODING POLYPEPTIDE HAVING CARBOXYPEPTIDASE ACTIVITY

(71) Applicant: Novozymes A/S, Bagsvaerd (DK)

(72) Inventors: Hanne Vang Hendriksen, Holte (DK); Gitte Budolfsen Lynglev, Frederiksberg (DK); Henrik Frisner, Frederiksberg (DK); Ciu Liu, Beijing (CN); Ye Liu, Beijing (CN); Eduardo Antonio Della Pia, Lyngby (DK); Hans Peter Heldt-Hansen, Virum (DK); Kenneth Jensen, Oelsted (DK); Wei Peng, Beijing (CN); Ming Li, Beijing (CN)

(73) Assignee: Novozymes A/S, Bagsvaerd (DK)

( * ) Notice: Subject to any disclaimer, the term of this patent is extended or adjusted under 35 U.S.C. 154(b) by 98 days.

(21) Appl. No.: 16/611,539

(22) PCT Filed: Jun. 8, 2018

(86) PCT No.: PCT/CN2018/090425
§ 371 (c)(1),
(2) Date: Nov. 7, 2019

(87) PCT Pub. No.: WO2018/224035
PCT Pub. Date: Dec. 13, 2018

(65) Prior Publication Data
US 2021/0147819 A1 May 20, 2021

(30) Foreign Application Priority Data
Jun. 9, 2017 (WO) ............... PCT/CN2017/087723

(51) Int. Cl.
*C12N 9/48* (2006.01)
*C12P 21/06* (2006.01)
(52) U.S. Cl.
CPC .............. *C12N 9/485* (2013.01); *C12P 21/06* (2013.01)
(58) Field of Classification Search
None
See application file for complete search history.

(56) References Cited

FOREIGN PATENT DOCUMENTS

| CN | 1078495 A | 11/1993 |
|---|---|---|
| EP | 0946106 B1 | 5/2002 |
| TW | 293553 B | 9/2006 |
| WO | 98/51163 A2 | 11/1998 |
| WO | 02/32232 A2 | 4/2002 |
| WO | 02/45524 A2 | 6/2002 |
| WO | 2005/112657 A1 | 12/2005 |
| WO | 2009/147103 A2 | 12/2009 |
| WO | 2010/009400 A1 | 1/2010 |
| WO | 2012/048334 A2 | 4/2012 |
| WO | 2014/059541 A1 | 4/2014 |
| WO | 2014/067950 A1 | 5/2014 |
| WO | 2014/110675 A1 | 7/2014 |
| WO | WO-2014138983 A1 * | 9/2014 ............... C12N 9/00 |
| WO | WO-2014202616 A2 * | 12/2014 ............. C07K 14/37 |
| WO | 2016/062855 A1 | 4/2016 |
| WO | 2016/210395 A1 | 12/2016 |

OTHER PUBLICATIONS

Accession V5G105. Jan. 22, 2014. (Year: 2014).*
Chica et al. Curr Opin Biotechnol. Aug. 2005;16(4):378-84. (Year: 2005).*
Singh et al. Curr Protein Pept Sci. 2017, 18, 1-11 (Year: 2017).*
Accession BBT32274. Feb. 26, 2015 (Year: 2015).*
Accession BBN40302 Nov. 6, 2014 (Year: 2014).*
Saha et al., Biotechnology Advances, vol. 19, No. 5, pp. 355-370 (2001).
Soerensen et al., Protein Science, vol. 6, No. 10, pp. 2227-2232 (1997).
Erickson et al., Digestive Diseases and Sciences, vol. 34, No. 3, pp. 400-406 (1989).
Goptar et al., Insect Biochemistry and Molecular Biology, vol. 43, No. 6, pp. 501-509 (2013).
Mika et al., Appl. Microbiol. Biotechnol., vol. 99, No. 19, pp. 7837-7846 (2015).
Visser et al., EBI Accession No. AZU83349 (2012).
Walter et al., Molecular & Cellular Biochemistry, vol. 30, No. 2, pp. 111-127 (1980).

* cited by examiner

*Primary Examiner* — Christian L Fronda
(74) *Attorney, Agent, or Firm* — Elias Lambiris

(57) ABSTRACT

Provided herein is a method for producing a protein hydrolysate using a polypeptide having endopeptidase activity and a polypeptide having carboxypeptidase activity and the use of these enzymes for hydrolysing a protein substrate. Also provided are polypeptides having carboxypeptidase activity and polynucleotides encoding the polypeptides, nucleic acid constructs, vectors, and host cells comprising the polynucleotides as well as methods of producing and using the polypeptides.

20 Claims, No Drawings
Specification includes a Sequence Listing.

SEQUENCE LISTING

```
<160> NUMBER OF SEQ ID NOS: 20

<210> SEQ ID NO 1
<211> LENGTH: 1718
<212> TYPE: DNA
<213> ORGANISM: Penicillium emersonii
<220> FEATURE:
<221> NAME/KEY: CDS
<222> LOCATION: (1)..(466)
<220> FEATURE:
<221> NAME/KEY: sig_peptide
<222> LOCATION: (1)..(45)
<220> FEATURE:
<221> NAME/KEY: mat_peptide
<222> LOCATION: (358)..(1687)
<220> FEATURE:
<221> NAME/KEY: CDS
<222> LOCATION: (519)..(1687)

<400> SEQUENCE: 1
```

```
atg aga gtt ctt cct gcg acg ctc ctg atc gga gcg gca gct gcg         45
Met Arg Val Leu Pro Ala Thr Leu Leu Ile Gly Ala Ala Ala Ala
            -115             -110            -105 gct gca cct ccg gcc cag cag gtc ctc gac ctg ccc agg cag ggc gcc     93
Ala Ala Pro Pro Ala Gln Gln Val Leu Asp Leu Pro Arg Gln Gly Ala
            -100             -95             -90 gag gcc gtc tcc aag ccg ctc cat cat ctc aag gag cat ctg aag acg    141
Glu Ala Val Ser Lys Pro Leu His His Leu Lys Glu His Leu Lys Thr
            -85              -80             -75 ctc acc gat gat gct cgc agt ctc tgg gag gaa gtg tcc aat atc ttc    189
Leu Thr Asp Asp Ala Arg Ser Leu Trp Glu Glu Val Ser Asn Ile Phe
        -70              -65             -60 ccc ggc gca atg gag agc gtt tcg gtc ttc tcc ttg ccc aag aag cac    237
Pro Gly Ala Met Glu Ser Val Ser Val Phe Ser Leu Pro Lys Lys His
        -55              -50             -45 acc cgt cgc ccc gac tcg cac tgg gac cac atc gtc cgt ggt tcg gac    285
Thr Arg Arg Pro Asp Ser His Trp Asp His Ile Val Arg Gly Ser Asp
-40             -35              -30             -25 gtc cag agc atc tgg gtt acc ggt gcc aac ggc gaa aag gag cgt gag    333
Val Gln Ser Ile Trp Val Thr Gly Ala Asn Gly Glu Lys Glu Arg Glu
            -20              -15             -10 gtt gat gga aag ctg gag gcg tac gac ctg agg gtc aag aag gtc gac    381
Val Asp Gly Lys Leu Glu Ala Tyr Asp Leu Arg Val Lys Lys Val Asp
        -5               -1   1            5 cct agc tcc ctg ggt gtt gat ccc aac gtc aag caa tac agt gga tac    429
Pro Ser Ser Leu Gly Val Asp Pro Asn Val Lys Gln Tyr Ser Gly Tyr
    10              15              20 ttg gac gac aat gag aac gac aag cac cta ttc tac t gtaagaatag       476
Leu Asp Asp Asn Glu Asn Asp Lys His Leu Phe Tyr
25              30              35 tcctgcgcca tgaagaaaag caagaaatta atttcattgc ag gg  ttc ttt gaa     529
                                                  Trp Phe Phe Glu
                                                              40 tct cgc aat gat ccg aag aat gac ccc gtc gtc ctc tgg ctg aat ggt    577
Ser Arg Asn Asp Pro Lys Asn Asp Pro Val Val Leu Trp Leu Asn Gly
            45              50              55 ggc cct ggc tgc tcg tcc ctc acg ggg ctg ttc ctg gag ctc ggg ccc    625
Gly Pro Gly Cys Ser Ser Leu Thr Gly Leu Phe Leu Glu Leu Gly Pro
        60              65              70 agc tcc gtg gat ggg aat ctg aat ctc cat tat aac caa tac tca tgg    673
Ser Ser Val Asp Gly Asn Leu Asn Leu His Tyr Asn Gln Tyr Ser Trp
        75              80              85 aac tcc aac gca tcg gtg atc ttc ctg gac cag ccg gtc aat gtc ggc    721
Asn Ser Asn Ala Ser Val Ile Phe Leu Asp Gln Pro Val Asn Val Gly
    90              95              100 tac tcg tac agc ggg tcc tcc gtc agc gac acc gtg gct gcc ggc aag    769
Tyr Ser Tyr Ser Gly Ser Ser Val Ser Asp Thr Val Ala Ala Gly Lys
105             110             115             120 gat gtt tac gcc ctg ctc act ctc ttc ttc aag caa ttc ccc gaa tat    817
Asp Val Tyr Ala Leu Leu Thr Leu Phe Phe Lys Gln Phe Pro Glu Tyr
            125             130             135 gcc acg cag gat ttc cac att gct ggc gag tcc tac gcc ggc cac tac    865
Ala Thr Gln Asp Phe His Ile Ala Gly Glu Ser Tyr Ala Gly His Tyr
            140             145             150 att cct gtc ttt gct tcg gag atc ctc tcc cac aag aag cgg aac atc    913
Ile Pro Val Phe Ala Ser Glu Ile Leu Ser His Lys Lys Arg Asn Ile
            155             160             165 aat ctg aag tcg gtg ctg atc ggc aac ggt ctc acc gat ggc ctc acc    961
Asn Leu Lys Ser Val Leu Ile Gly Asn Gly Leu Thr Asp Gly Leu Thr
```

```
                170                 175                 180
cag tat gcc tac tac cgg ccc atg gcc tgt gga gag ggc ggt tac ccg       1009
Gln Tyr Ala Tyr Tyr Arg Pro Met Ala Cys Gly Glu Gly Gly Tyr Pro
185                 190                 195                 200 gct gtc ttg gac gag agc tcg tgc cgc tct atg gac aac gcc ctg cct       1057
Ala Val Leu Asp Glu Ser Ser Cys Arg Ser Met Asp Asn Ala Leu Pro
                205                 210                 215 cgc tgc cag tcc atg atc cag agt tgc tac gac acc gag agc acc tgg       1105
Arg Cys Gln Ser Met Ile Gln Ser Cys Tyr Asp Thr Glu Ser Thr Trp
            220                 225                 230 gtg tgt gtg cct gcg gcc atc tac tgc aac aac gcc atg ctg gct ccc       1153
Val Cys Val Pro Ala Ala Ile Tyr Cys Asn Asn Ala Met Leu Ala Pro
        235                 240                 245 tac cag cgc acg ggc caa aat gtt tac gac gtg cgc ggc aag tgt gag       1201
Tyr Gln Arg Thr Gly Gln Asn Val Tyr Asp Val Arg Gly Lys Cys Glu
    250                 255                 260 gac agc agc aac ctg tgc tac aag gct ctg ggc tac acc agc gag tac       1249
Asp Ser Ser Asn Leu Cys Tyr Lys Ala Leu Gly Tyr Thr Ser Glu Tyr
265                 270                 275                 280 ctc aac cag ccg gag gtg atc aag gcg ctg ggt gcc gaa gtg gac agc       1297
Leu Asn Gln Pro Glu Val Ile Lys Ala Leu Gly Ala Glu Val Asp Ser
                285                 290                 295 tac gac tcg tgc aac ttc gac atc aac cgg aac ttc ctc ttc cac ggt       1345
Tyr Asp Ser Cys Asn Phe Asp Ile Asn Arg Asn Phe Leu Phe His Gly
            300                 305                 310 gac tgg atg aag cca tac cac cgt gtg gtg ccg ggc ctg ctg gag cag       1393
Asp Trp Met Lys Pro Tyr His Arg Val Val Pro Gly Leu Leu Glu Gln
        315                 320                 325 atc ccc gtg ctg atc tac gcg ggt gat gcg gac ttt atc tgc aac tgg       1441
Ile Pro Val Leu Ile Tyr Ala Gly Asp Ala Asp Phe Ile Cys Asn Trp
    330                 335                 340 ctc ggc aac aag gcc tgg acg gag gcc ctg gag tgg cac ggc cgg gag       1489
Leu Gly Asn Lys Ala Trp Thr Glu Ala Leu Glu Trp His Gly Arg Glu
345                 350                 355                 360 gaa ttc gcg tcg acc gag ctg gag gat ctg gtg atc gtc aac agc gag       1537
Glu Phe Ala Ser Thr Glu Leu Glu Asp Leu Val Ile Val Asn Ser Glu
                365                 370                 375 cac cag ggc aag aag atc ggt cag gtg aag tcc tcg ggc aac ttc acc       1585
His Gln Gly Lys Lys Ile Gly Gln Val Lys Ser Ser Gly Asn Phe Thr
            380                 385                 390 ttc atg cgg atc tac gga ggc ggc cac atg gtg ccg atg gac cag ccg       1633
Phe Met Arg Ile Tyr Gly Gly Gly His Met Val Pro Met Asp Gln Pro
        395                 400                 405 gag gcg agt ctg gag ttt ttc aac cgc tgg ctc gga ggg gaa tgg ttt       1681
Glu Ala Ser Leu Glu Phe Phe Asn Arg Trp Leu Gly Gly Glu Trp Phe
    410                 415                 420 tct agc tgatcggcaa cctgagaagc gtgtcgcgtt c                            1718
Ser Ser
425

<210> SEQ ID NO 2
<211> LENGTH: 545
<212> TYPE: PRT
<213> ORGANISM: Penicillium emersonii

<400> SEQUENCE: 2

Met Arg Val Leu Pro  Ala Thr Leu Leu Ile  Gly Ala Ala Ala Ala
                -115                 -110                 -105

Ala Ala Pro Pro Ala  Gln Gln Val Leu Asp  Leu Pro Arg Gln Gly Ala
                -100                 -95                  -90
```

```
Glu Ala Val Ser Lys Pro Leu His His Leu Lys Glu His Leu Lys Thr
            -85             -80                 -75

Leu Thr Asp Asp Ala Arg Ser Leu Trp Glu Val Ser Asn Ile Phe
        -70             -65                 -60

Pro Gly Ala Met Glu Ser Val Ser Val Phe Ser Leu Pro Lys Lys His
        -55             -50                 -45

Thr Arg Arg Pro Asp Ser His Trp Asp His Ile Val Arg Gly Ser Asp
-40                 -35             -30                 -25

Val Gln Ser Ile Trp Val Thr Gly Ala Asn Gly Glu Lys Glu Arg Glu
                -20             -15                 -10

Val Asp Gly Lys Leu Glu Ala Tyr Asp Leu Arg Val Lys Lys Val Asp
            -5              -1  1                    5

Pro Ser Ser Leu Gly Val Asp Pro Asn Val Lys Gln Tyr Ser Gly Tyr
            10              15                  20

Leu Asp Asp Asn Glu Asn Asp Lys His Leu Phe Tyr Trp Phe Phe Glu
25                  30              35                  40

Ser Arg Asn Asp Pro Lys Asn Asp Pro Val Leu Trp Leu Asn Gly
                45              50                  55

Gly Pro Gly Cys Ser Ser Leu Thr Gly Leu Phe Leu Glu Leu Gly Pro
            60              65                  70

Ser Ser Val Asp Gly Asn Leu Asn Leu His Tyr Asn Gln Tyr Ser Trp
        75              80                  85

Asn Ser Asn Ala Ser Val Ile Phe Leu Asp Gln Pro Val Asn Val Gly
90                  95              100

Tyr Ser Tyr Ser Gly Ser Val Ser Asp Thr Val Ala Ala Gly Lys
105                 110             115                 120

Asp Val Tyr Ala Leu Leu Thr Leu Phe Phe Lys Gln Phe Pro Glu Tyr
            125             130                 135

Ala Thr Gln Asp Phe His Ile Ala Gly Glu Ser Tyr Ala Gly His Tyr
            140             145                 150

Ile Pro Val Phe Ala Ser Glu Ile Leu Ser His Lys Lys Arg Asn Ile
        155             160                 165

Asn Leu Lys Ser Val Leu Ile Gly Asn Gly Leu Thr Asp Gly Leu Thr
170                 175             180

Gln Tyr Ala Tyr Tyr Arg Pro Met Ala Cys Gly Glu Gly Gly Tyr Pro
185                 190             195                 200

Ala Val Leu Asp Glu Ser Ser Cys Arg Ser Met Asp Asn Ala Leu Pro
            205             210                 215

Arg Cys Gln Ser Met Ile Gln Ser Cys Tyr Asp Thr Glu Ser Thr Trp
            220             225                 230

Val Cys Val Pro Ala Ala Ile Tyr Cys Asn Asn Ala Met Leu Ala Pro
            235             240                 245

Tyr Gln Arg Thr Gly Gln Asn Val Tyr Asp Val Arg Gly Lys Cys Glu
250                 255             260

Asp Ser Ser Asn Leu Cys Tyr Lys Ala Leu Gly Tyr Thr Ser Glu Tyr
265                 270             275                 280

Leu Asn Gln Pro Glu Val Ile Lys Ala Leu Gly Ala Glu Val Asp Ser
            285             290                 295

Tyr Asp Ser Cys Asn Phe Asp Ile Asn Arg Asn Phe Leu Phe His Gly
            300             305                 310

Asp Trp Met Lys Pro Tyr His Arg Val Val Pro Gly Leu Leu Glu Gln
            315             320                 325
```

```
Ile Pro Val Leu Ile Tyr Ala Gly Asp Ala Asp Phe Ile Cys Asn Trp
    330                 335                 340

Leu Gly Asn Lys Ala Trp Thr Glu Ala Leu Glu Trp His Gly Arg Glu
345                 350                 355                 360

Glu Phe Ala Ser Thr Glu Leu Glu Asp Leu Val Ile Val Asn Ser Glu
                365                 370                 375

His Gln Gly Lys Lys Ile Gly Gln Val Lys Ser Ser Gly Asn Phe Thr
            380                 385                 390

Phe Met Arg Ile Tyr Gly Gly His Met Val Pro Met Asp Gln Pro
        395                 400                 405

Glu Ala Ser Leu Glu Phe Phe Asn Arg Trp Leu Gly Gly Trp Phe
    410                 415                 420

Ser Ser
425

<210> SEQ ID NO 3
<211> LENGTH: 1720
<212> TYPE: DNA
<213> ORGANISM: Myceliophthora heterothallica

<400> SEQUENCE: 3
```

| | | | | | |
|---|---|---|---|---|---|
| atgaggatcg | cagcctccac | agtgctgctc | ggcgcggcct | ctgccgcctc | gttccagcag | 60 |
| caggcccagc | atgtgctctc | ggacggcttt | gggaaggccc | aggaggccat | gaagcccctt | 120 |
| tcggacgctc | tcgctgatgc | tgctggtcgc | cctatcgaga | atttcgagga | ggctttctcc | 180 |
| ggcatgaccg | ccgaggcaaa | ggctctctgg | gaggagatca | gctgctcgt | tcccgacagc | 240 |
| gccttcaaga | atccttcgtg | gttcagcaag | cccaagcctc | accgccgccg | cgatgactgg | 300 |
| gaccatgtcg | tcaagggcgc | cgatgtccag | aatatctggg | tgcaggatgc | caacggcgag | 360 |
| agccaccgcc | aagttggcgg | ccgcattgag | gactacaacc | ttcgcgtcaa | gacggtcgac | 420 |
| ccgtccaagc | ttggcgtcga | ttcggtcaag | cagttcagcg | gctaccttga | tgatgaggcc | 480 |
| aacgacaagc | acctcttcta | ctgtaaggtc | cagcgcttta | cactccgtgg | gccccctcgt | 540 |
| actgaccgga | cgtctagggt | tcttcgagtc | gcgcaatgac | cccaagaacg | acccggtcgt | 600 |
| cctctggctc | aacggcggcc | caggctgctc | gtcccttacc | ggcctctttc | tcgagctcgg | 660 |
| tccttcctcg | atcgacaaga | acctgaaggt | cgttaacaat | gagttcagct | ggaacaacaa | 720 |
| cgccagcgtc | atcttcctcg | accagcccgt | caatgtcggc | tattcctatt | ccggttcctc | 780 |
| cgtgagcaat | accattgctg | ctggcaagga | tgtctacgct | ctcttgactc | tcttcttcca | 840 |
| tcaattcccc | gagtacgcga | agcaggactt | ccacatcgct | ggcgagtcgt | atgctggcca | 900 |
| ctacattccc | gtttccgcgt | ccgagattct | gtctcacaag | aaccgcaaca | tcaacctcaa | 960 |
| gtccatcctg | attggtaacg | gcctgaccga | cggcctcacc | cagtacgagt | actaccgtcc | 1020 |
| tatggcttgc | ggagagggtg | gctatcccgc | tgtcctcagc | gagtctgagt | gccggagcat | 1080 |
| ggacaacgcc | ctgccgcggt | gccagtcgct | catccggaac | tgctacgaca | gcggcagcgt | 1140 |
| ctggagctgt | gtcccggcct | ccatctactg | taacaacgcc | ctgattggcc | cctaccagcg | 1200 |
| caccggtcag | aatgtctacg | atatccgcgg | caagtgcgag | gacagcagca | acctttgcta | 1260 |
| cagcgcactc | ggttatatca | gcgactatct | caaccagcag | tccgtcatgg | atgccctcgg | 1320 |
| tgtcgaggtc | tcgagctatg | agagctgcaa | tttcgacatc | aaccgcaatt | tcctgttcca | 1380 |
| aggcgattgg | atgcagccgt | tccatcgcct | ggtgccgaac | attctcaagg | agatccccgt | 1440 |
| cctcatctat | gccggtgatg | ccgactacat | ttgcaactgg | cttggcaacc | gagcttggac | 1500 |

-continued

```
tgagaagctc gagtggcccg gccagaaggc tttcaaccag gccaaggtcc atgatctgaa      1560
gttggctggt gctgacgagg agtacggcaa ggtcaaggcc tcgggcaatt tcaccttcat      1620
gcaaatctac caggccggtc acatggtccc catggaccag cctgagaatt cgctcgattt      1680
cctgaacagg tggctgagcg gcgaatggtt tgccaagtag                            1720
```

```
<210> SEQ ID NO 4
<211> LENGTH: 554
<212> TYPE: PRT
<213> ORGANISM: Myceliophthora heterothallica
<220> FEATURE:
<221> NAME/KEY: SIGNAL
<222> LOCATION: (1)..(15)
<220> FEATURE:
<221> NAME/KEY: mat_peptide
<222> LOCATION: (138)..(554)

<400> SEQUENCE: 4
```

Met Arg Ile Ala Ala Ser Thr Val Leu Leu Gly Ala Ala Ser Ala
     -135           -130           -125

Ala Ser Phe Gln Gln Gln Ala Gln His Val Leu Ser Asp Gly Phe
     -120           -115           -110

Gly Lys Ala Gln Glu Ala Met Lys Pro Leu Ser Asp Ala Leu Ala Asp
     -105           -100           -95

Ala Ala Gly Arg Pro Ile Glu Asn Phe Glu Glu Ala Phe Ser Gly Met
     -90           -85           -80

Thr Ala Glu Ala Lys Ala Leu Trp Glu Glu Ile Lys Leu Leu Val Pro
-75           -70           -65           -60

Asp Ser Ala Phe Lys Asn Pro Ser Trp Phe Ser Lys Pro Lys Pro His
     -55           -50           -45

Arg Arg Arg Asp Asp Trp Asp His Val Val Lys Gly Ala Asp Val Gln
     -40           -35           -30

Asn Ile Trp Val Gln Asp Ala Asn Gly Glu Ser His Arg Gln Val Gly
     -25           -20           -15

Gly Arg Ile Glu Asp Tyr Asn Leu Arg Val Lys Thr Val Asp Pro Ser
     -10           -5           -1  1           5

Lys Leu Gly Val Asp Ser Val Lys Gln Phe Ser Gly Tyr Leu Asp Asp
          10            15            20

Glu Ala Asn Asp Lys His Leu Phe Tyr Trp Phe Phe Glu Ser Arg Asn
          25            30            35

Asp Pro Lys Asn Asp Pro Val Val Leu Trp Leu Asn Gly Gly Pro Gly
          40            45            50

Cys Ser Ser Leu Thr Gly Leu Phe Leu Glu Leu Gly Pro Ser Ser Ile
55           60           65

Asp Lys Asn Leu Lys Val Val Asn Asn Glu Phe Ser Trp Asn Asn
70           75           80           85

Ala Ser Val Ile Phe Leu Asp Gln Pro Val Asn Val Gly Tyr Ser Tyr
          90            95           100

Ser Gly Ser Ser Val Ser Asn Thr Ile Ala Ala Gly Lys Asp Val Tyr
          105           110          115

Ala Leu Leu Thr Leu Phe Phe His Gln Phe Pro Glu Tyr Ala Lys Gln
          120           125          130

Asp Phe His Ile Ala Gly Glu Ser Tyr Ala Gly His Tyr Ile Pro Val
          135           140          145

Phe Ala Ser Glu Ile Leu Ser His Lys Asn Arg Asn Ile Asn Leu Lys
150           155           160          165

Ser Ile Leu Ile Gly Asn Gly Leu Thr Asp Gly Leu Thr Gln Tyr Glu
            170                 175                 180

Tyr Tyr Arg Pro Met Ala Cys Gly Glu Gly Tyr Pro Ala Val Leu
        185                 190                 195

Ser Glu Ser Glu Cys Arg Ser Met Asp Asn Ala Leu Pro Arg Cys Gln
            200                 205                 210

Ser Leu Ile Arg Asn Cys Tyr Asp Ser Gly Ser Val Trp Ser Cys Val
            215                 220                 225

Pro Ala Ser Ile Tyr Cys Asn Asn Ala Leu Ile Gly Pro Tyr Gln Arg
230                 235                 240                 245

Thr Gly Gln Asn Val Tyr Asp Ile Arg Gly Lys Cys Glu Asp Ser Ser
            250                 255                 260

Asn Leu Cys Tyr Ser Ala Leu Gly Tyr Ile Ser Asp Tyr Leu Asn Gln
            265                 270                 275

Gln Ser Val Met Asp Ala Leu Gly Val Glu Val Ser Ser Tyr Glu Ser
            280                 285                 290

Cys Asn Phe Asp Ile Asn Arg Asn Phe Leu Phe Gln Gly Asp Trp Met
            295                 300                 305

Gln Pro Phe His Arg Leu Val Pro Asn Ile Leu Lys Glu Ile Pro Val
310                 315                 320                 325

Leu Ile Tyr Ala Gly Asp Ala Asp Tyr Ile Cys Asn Trp Leu Gly Asn
                330                 335                 340

Arg Ala Trp Thr Glu Lys Leu Glu Trp Pro Gly Gln Lys Ala Phe Asn
            345                 350                 355

Gln Ala Lys Val His Asp Leu Lys Leu Ala Gly Ala Asp Glu Glu Tyr
            360                 365                 370

Gly Lys Val Lys Ala Ser Gly Asn Phe Thr Phe Met Gln Ile Tyr Gln
    375                 380                 385

Ala Gly His Met Val Pro Met Asp Gln Pro Glu Asn Ser Leu Asp Phe
390                 395                 400                 405

Leu Asn Arg Trp Leu Ser Gly Glu Trp Phe Ala Lys
            410                 415

<210> SEQ ID NO 5
<211> LENGTH: 1722
<212> TYPE: DNA
<213> ORGANISM: Chaetomium strumarium

<400> SEQUENCE: 5
atgaggatcg ctgcgtcgac agtgctgttc ggcgctgctt ccgcagcttc gttccagcag      60
caggcccagc atgtgctttc aggcggcttt ggaaaggcgc aagacgccat gaagcccatt     120
tcagatgcct tcgctgacgc agctgctcac cctatcgaga gcttcgagga ggctttccag     180
ggtgtcagcg ccgagacgaa ggcgctctgg gacgagatca agctgctcgt tcccgagagc     240
gccttcaaga tccttcgtg gttgagcaag cccaagccgc accgccggcg caacgattgg     300
gaccatgtcg tcaagggcgc cgatgtgcag aaggtgtggg tgcagggtgc cgatggcgag     360
agccaccgcg aggttggcgg ccggctcgag aactacaaca tgcgcgtcaa gtcggtcgac     420
ccgtccaagc tcggcattga ttcagtcaag caatatagtg ttaccttga cgatgaagct     480 aatgacaagc acttattcta ctgtgagttc ccatcaatag ctcgccaata gccatacccc     540
tgctaactca ccgctatagg gttcttcgag tcgcgcaatg accccaagaa cgacccggtt     600
gtcctctggc tcaacggcgg gcctggttgc tcatccctta cggggctttt cctcgagctt     660
ggtccttcgt cgattgacaa gaagctcaag gttgtgaaca acgagttcag ctggaacaat     720

```
aacgccagcg tcatcttcct tgaccagcct gtcaacgtcg gatactcgta ctccggatct      780
tccgtgagca acaccatcgc tgccggcaag gacgtctacg ctctcttaac cctgttcttc      840
caccaattcc ccgaatacgc caagcaggac ttccacattg ccggcgaatc gtacgctggc      900
cactacattc ccgtcttcgc ttctgagatc ctgtcgcaca agaaccgaaa catcaacctc      960
aagtccgttc tgattggcaa cggtctgacg gacggtctca ctcagtacga gtactaccgt     1020
cccatggcct gcggcgaagg cggctacccc gctgtcctga gcgaatctga gtgccagagc     1080
atggacaacg cgctgccgag atgccagtcg ctgatcaaca actgctacga agcggcagc     1140 gtgtggagct gcgtcccggc ttccatctac tgcaacaacg ctttgattgg ccctaccag     1200 cgcactggcc agaatgtcta cgacatccgc ggcaagtgcg aggacagcag caacctctgc     1260
tacagcgctc taggctggat cagcgactac ctgaaccagc agtccgtcat ggatgccctt     1320
ggcgttgagg tctcgagcta cgagagctgc aacttcgaca tcaaccgcaa cttcctgttc     1380
cagggagact ggatgcagcc tttccaccgc ctggtgccca acatcctcaa ggagatcccg     1440
gtgctcatct atgccggtga tgccgattac atctgcaact ggcttggcaa ccaggcctgg     1500
accgaggctc tggagtggtc cggcaagaag gacttcaacc acgccaaggt caaggacctg     1560
aagcttgccg gggctgacaa ggagtacggc aaggtcaagg catctgggaa cttcaccttc     1620
atgcgcatct accaggccgg tcatatggtc cctatggacc agcccgagaa ctcgcttgac     1680
ttcctgaata ggtggttggg tggcgaatgg ttggcgcact ag                       1722
```

<210> SEQ ID NO 6
<211> LENGTH: 554
<212> TYPE: PRT
<213> ORGANISM: Chaetomium strumarium
<220> FEATURE:
<221> NAME/KEY: SIGNAL
<222> LOCATION: (1)..(15)
<220> FEATURE:
<221> NAME/KEY: mat_peptide
<222> LOCATION: (111)..(554)

<400> SEQUENCE: 6

```
Met  Arg  Ile  Ala  Ala  Ser  Thr  Val  Leu  Phe  Gly  Ala  Ala  Ser  Ala
-110                 -105                 -100

Ala  Ser  Phe  Gln  Gln  Gln  Ala  Gln  His  Val  Leu  Ser  Gly  Gly  Phe  Gly
     -95                  -90                  -85                       -80

Lys  Ala  Gln  Asp  Ala  Met  Lys  Pro  Ile  Ser  Asp  Ala  Phe  Ala  Asp  Ala
                 -75                  -70                       -65

Ala  Ala  His  Pro  Ile  Glu  Ser  Phe  Glu  Ala  Phe  Gln  Gly  Val  Ser
                 -60                  -55                       -50

Ala  Glu  Thr  Lys  Ala  Leu  Trp  Asp  Glu  Ile  Lys  Leu  Leu  Val  Pro  Glu
          -45                  -40                       -35

Ser  Ala  Phe  Lys  Asn  Pro  Ser  Trp  Leu  Ser  Lys  Pro  Lys  Pro  His  Arg
          -30                  -25                       -20

Arg  Arg  Asn  Asp  Trp  Asp  His  Val  Val  Lys  Gly  Ala  Asp  Val  Gln  Lys
          -15                  -10                   -5                   -1  1

Val  Trp  Val  Gln  Gly  Ala  Asp  Gly  Glu  Ser  His  Arg  Glu  Val  Gly  Gly
                 5                    10                        15

Arg  Leu  Glu  Asn  Tyr  Asn  Met  Arg  Val  Lys  Ser  Val  Asp  Pro  Ser  Lys
                 20                   25                        30

Leu  Gly  Ile  Asp  Ser  Val  Lys  Gln  Tyr  Ser  Gly  Tyr  Leu  Asp  Asp  Glu
                 35                   40                        45
```

Ala Asn Asp Lys His Leu Phe Tyr Trp Phe Glu Ser Arg Asn Asp
 50                  55                  60                  65

Pro Lys Asn Asp Pro Val Val Leu Trp Leu Asn Gly Gly Pro Gly Cys
             70                  75                  80

Ser Ser Leu Thr Gly Leu Phe Leu Glu Leu Gly Pro Ser Ser Ile Asp
                 85                  90                  95

Lys Lys Leu Lys Val Val Asn Asn Glu Phe Ser Trp Asn Asn Asn Ala
            100                 105                 110

Ser Val Ile Phe Leu Asp Gln Pro Val Asn Val Gly Tyr Ser Tyr Ser
        115                 120                 125

Gly Ser Ser Val Ser Asn Thr Ile Ala Ala Gly Lys Asp Val Tyr Ala
130                 135                 140                 145

Leu Leu Thr Leu Phe Phe His Gln Phe Pro Glu Tyr Ala Lys Gln Asp
                150                 155                 160

Phe His Ile Ala Gly Glu Ser Tyr Ala Gly His Tyr Ile Pro Val Phe
                165                 170                 175

Ala Ser Glu Ile Leu Ser His Lys Asn Arg Asn Ile Asn Leu Lys Ser
            180                 185                 190

Val Leu Ile Gly Asn Gly Leu Thr Asp Gly Leu Thr Gln Tyr Glu Tyr
        195                 200                 205

Tyr Arg Pro Met Ala Cys Gly Glu Gly Gly Tyr Pro Ala Val Leu Ser
210                 215                 220                 225

Glu Ser Glu Cys Gln Ser Met Asp Asn Ala Leu Pro Arg Cys Gln Ser
                230                 235                 240

Leu Ile Asn Asn Cys Tyr Glu Ser Gly Ser Val Trp Ser Cys Val Pro
            245                 250                 255

Ala Ser Ile Tyr Cys Asn Asn Ala Leu Ile Gly Pro Tyr Gln Arg Thr
        260                 265                 270

Gly Gln Asn Val Tyr Asp Ile Arg Gly Lys Cys Glu Asp Ser Ser Asn
275                 280                 285

Leu Cys Tyr Ser Ala Leu Gly Trp Ile Ser Asp Tyr Leu Asn Gln Gln
290                 295                 300                 305

Ser Val Met Asp Ala Leu Gly Val Glu Val Ser Ser Tyr Glu Ser Cys
            310                 315                 320

Asn Phe Asp Ile Asn Arg Asn Phe Leu Phe Gln Gly Asp Trp Met Gln
        325                 330                 335

Pro Phe His Arg Leu Val Pro Asn Ile Leu Lys Glu Ile Pro Val Leu
            340                 345                 350

Ile Tyr Ala Gly Asp Ala Asp Tyr Ile Cys Asn Trp Leu Gly Asn Gln
        355                 360                 365

Ala Trp Thr Glu Ala Leu Glu Trp Ser Gly Lys Lys Asp Phe Asn His
370                 375                 380                 385

Ala Lys Val Lys Asp Leu Lys Leu Ala Gly Ala Asp Lys Glu Tyr Gly
            390                 395                 400

Lys Val Lys Ala Ser Gly Asn Phe Thr Phe Met Arg Ile Tyr Gln Ala
        405                 410                 415

Gly His Met Val Pro Met Asp Gln Pro Glu Asn Ser Leu Asp Phe Leu
            420                 425                 430

Asn Arg Trp Leu Gly Gly Glu Trp Leu Ala His
        435                 440

<210> SEQ ID NO 7
<211> LENGTH: 1824
<212> TYPE: DNA

```
<213> ORGANISM: Lasiodiplodia theobromae
<220> FEATURE:
<221> NAME/KEY: CDS
<222> LOCATION: (1)..(248)
<220> FEATURE:
<221> NAME/KEY: CDS
<222> LOCATION: (304)..(357)
<220> FEATURE:
<221> NAME/KEY: CDS
<222> LOCATION: (410)..(534)
<220> FEATURE:
<221> NAME/KEY: CDS
<222> LOCATION: (586)..(749)
<220> FEATURE:
<221> NAME/KEY: CDS
<222> LOCATION: (804)..(1314)
<220> FEATURE:
<221> NAME/KEY: CDS
<222> LOCATION: (1363)..(1454)
<220> FEATURE:
<221> NAME/KEY: CDS
<222> LOCATION: (1520)..(1694)
<220> FEATURE:
<221> NAME/KEY: CDS
<222> LOCATION: (1760)..(1821)

<400> SEQUENCE: 7 atg cgg tct tcg ctc gcc ttt gtg gct tct gcc ctc tcc gtg gcc cac       48
Met Arg Ser Ser Leu Ala Phe Val Ala Ser Ala Leu Ser Val Ala His
1               5                   10                  15 ctg gcc ctg gct gct ccc ttc tcc ggc aag gtc gac aag cgt tcg acc       96
Leu Ala Leu Ala Ala Pro Phe Ser Gly Lys Val Asp Lys Arg Ser Thr
            20                  25                  30 gtc gag aag gat gga gtg cgc tac aac gtc ttc gag cac gct gcc acg      144
Val Glu Lys Asp Gly Val Arg Tyr Asn Val Phe Glu His Ala Ala Thr
        35                  40                  45 ggt gcg aag ctg gag ttt gtc aac aac agc gga atc tgt gag acc act      192
Gly Ala Lys Leu Glu Phe Val Asn Asn Ser Gly Ile Cys Glu Thr Thr
    50                  55                  60 ccc ggc gtc aat cag tac tcg ggt tac ctt tcg gtc ggc acc aac atg      240
Pro Gly Val Asn Gln Tyr Ser Gly Tyr Leu Ser Val Gly Thr Asn Met
65                  70                  75                  80 aac atg tg  gtacgtaaca gccaccccgg ctgaaaagat ttcgaaacat              288
Asn Met Trp tgacgaaaca cgcag g ttc tgg ctg ttt gag gcg aga gag aac ccc acg       337
                Phe Trp Leu Phe Glu Ala Arg Glu Asn Pro Thr
                    85                  90 act gcg ccg ctt gcc gca tg  gtacttgctg ggccctccct gttttgaaac         387
Thr Ala Pro Leu Ala Ala Trp
95              100 gaaggattta ctgatgaaac ag g ttc aac ggc ggt cct gga tgc tcc agc       437
                        Phe Asn Gly Gly Pro Gly Cys Ser Ser
                                105                 110 atg atc ggc ctc ttc cag gag aac ggt ccc tgc cac ttc gtc gac ggt      485
Met Ile Gly Leu Phe Gln Glu Asn Gly Pro Cys His Phe Val Asp Gly
                115                 120                 125 tcc acc gag ccc agc ctg aac gag tac agc tgg aac tcg tac gcc aac a    534
Ser Thr Glu Pro Ser Leu Asn Glu Tyr Ser Trp Asn Ser Tyr Ala Asn
            130                 135                 140 gtacgcaaat cctcatgtga caccttctg cattattga cattatcaaa g tg atc        590
                                                        Met Ile tac att gat cag cca att ggc gtc ggc ttc agc tac gga aat gac gaa      638
Tyr Ile Asp Gln Pro Ile Gly Val Gly Phe Ser Tyr Gly Asn Asp Glu
145                 150                 155                 160 gtt gtc gat tcc acc gag act gcc gct cct tac gtg tgg aag ctt atc      686
```

```
Val Val Asp Ser Thr Glu Thr Ala Ala Pro Tyr Val Trp Lys Leu Ile
        165                 170                 175 cag gcc ttc tat gac gct ttt ccc cag tac gag agc agg gat ttc ggc      734
Gln Ala Phe Tyr Asp Ala Phe Pro Gln Tyr Glu Ser Arg Asp Phe Gly
        180                 185                 190 att ttc acc gaa tcc gtaagttctt tcttgacgca cgtagcgctt gtccgacggc      789
Ile Phe Thr Glu Ser
            195 taatagctct ccag tac ggc ggt cac tac ggt cct gaa ttt gcc cac tac      839
               Tyr Gly Gly His Tyr Gly Pro Glu Phe Ala His Tyr
                            200                 205 atc cag gat cag aac aac ggc att gcc agt ggc agt gtt gac ggc caa      887
Ile Gln Asp Gln Asn Asn Gly Ile Ala Ser Gly Ser Val Asp Gly Gln
210                 215                 220                 225 aaa atc aat ctg att gca ctt ggc gtc aac aac ggc tgg att gat gcc      935
Lys Ile Asn Leu Ile Ala Leu Gly Val Asn Asn Gly Trp Ile Asp Ala
                230                 235                 240 gag ctg cag gag aag gcc tac atc gac tac agt ctc aac aac acc tac      983
Glu Leu Gln Glu Lys Ala Tyr Ile Asp Tyr Ser Leu Asn Asn Thr Tyr
            245                 250                 255 aag aag att atc agc cag agc gag gct acg tct tac tac aac gcc tac     1031
Lys Lys Ile Ile Ser Gln Ser Glu Ala Thr Ser Tyr Tyr Asn Ala Tyr
        260                 265                 270 aca aag acc tgc ctg ccc gcc atc cag agc tgc gag agc acc ggc act     1079
Thr Lys Thr Cys Leu Pro Ala Ile Gln Ser Cys Glu Ser Thr Gly Thr
275                 280                 285 gtc tcg gcc tgc gtc aac gcc gac aac aag tgc tac aac agc atc gag     1127
Val Ser Ala Cys Val Asn Ala Asp Asn Lys Cys Tyr Asn Ser Ile Glu
290                 295                 300                 305 ggc cct ctg agt gaa gag gct gac ttc aac gtt tat gat gtc cgc att     1175
Gly Pro Leu Ser Glu Glu Ala Asp Phe Asn Val Tyr Asp Val Arg Ile
            310                 315                 320 gga gcc agt gtg acg gac ccg ccc gag acc tac gcc gac tat ctc gcc     1223
Gly Ala Ser Val Thr Asp Pro Pro Glu Thr Tyr Ala Asp Tyr Leu Ala
            325                 330                 335 cgt gat gat gtg aag aag gcc atc ggt gcg cgc tcc acc tac tct gag     1271
Arg Asp Asp Val Lys Lys Ala Ile Gly Ala Arg Ser Thr Tyr Ser Glu
        340                 345                 350 tgc gcg gat acc ccg tac aac aag ttc tcg tcc acc ggt gac a            1314
Cys Ala Asp Thr Pro Tyr Asn Lys Phe Ser Ser Thr Gly Asp
        355                 360                 365 gtatgttttc ttcctgatgc ctgtatgaaa atccactgac catcccag ac  ccg cgc     1370
                                                        Asn Pro Arg
                                                                370 tcc ttc ctg ccc gag ctc aac tcc gtc gtc caa tcg ggc ttg acc acc     1418
Ser Phe Leu Pro Glu Leu Asn Ser Val Val Gln Ser Gly Leu Thr Thr
                375                 380                 385 ctc gtc tgg gct ggc gat gct gac tgg att tgc aac gtaagctttt          1464
Leu Val Trp Ala Gly Asp Ala Asp Trp Ile Cys Asn
            390                 395 gatcctgtct gccccgtgaa acaatttcat ttctgacatt taccaaacaa tgcag tgg    1522
                                                                Trp atg ggt aac tac gac gct gcg caa gct gtt gag ttt gat ggt cag acc     1570
Met Gly Asn Tyr Asp Ala Ala Gln Ala Val Glu Phe Asp Gly Gln Thr
400                 405                 410                 415 gag ttc cgc gcc gcc tcg ctt gag cct tac aaa gtc aac ggc gtc gag     1618
Glu Phe Arg Ala Ala Ser Leu Glu Pro Tyr Lys Val Asn Gly Val Glu
            420                 425                 430 ggt ggc acc ttc aag acc gtc gac aac ttc tcg ttc ctg cgc gtc tat     1666
```

-continued

```
Gly Gly Thr Phe Lys Thr Val Asp Asn Phe Ser Phe Leu Arg Val Tyr
            435                 440                 445 gag gcc ggt cac gag gtg cct tac tac c gtaagtttcc taagcatatc         1714
Glu Ala Gly His Glu Val Pro Tyr Tyr
            450                 455 cgtagcagac accggtgcaa catgaactga cgtcgtttcc cgcag ag  ccc gag ctt   1770
                                                     Gln Pro Glu Leu
                                                                 460 gcc ctc cag gtc ttc aag cag acc atg cag aag aag ccc atc tcg tcg    1818
Ala Leu Gln Val Phe Lys Gln Thr Met Gln Lys Lys Pro Ile Ser Ser
                465                 470                 475 act tag                                                             1824
Thr

<210> SEQ ID NO 8
<211> LENGTH: 477
<212> TYPE: PRT
<213> ORGANISM: Lasiodiplodia theobromae

<400> SEQUENCE: 8

Met Arg Ser Ser Leu Ala Phe Val Ala Ser Ala Leu Ser Val Ala His
1               5                   10                  15

Leu Ala Leu Ala Ala Pro Phe Ser Gly Lys Val Asp Lys Arg Ser Thr
                20                  25                  30

Val Glu Lys Asp Gly Val Arg Tyr Asn Val Phe Glu His Ala Ala Thr
            35                  40                  45

Gly Ala Lys Leu Glu Phe Val Asn Asn Ser Gly Ile Cys Glu Thr Thr
        50                  55                  60

Pro Gly Val Asn Gln Tyr Ser Gly Tyr Leu Ser Val Gly Thr Asn Met
65                  70                  75                  80

Asn Met Trp Phe Trp Leu Phe Glu Ala Arg Glu Asn Pro Thr Thr Ala
                85                  90                  95

Pro Leu Ala Ala Trp Phe Asn Gly Gly Pro Gly Cys Ser Ser Met Ile
            100                 105                 110

Gly Leu Phe Gln Glu Asn Gly Pro Cys His Phe Val Asp Gly Ser Thr
        115                 120                 125

Glu Pro Ser Leu Asn Glu Tyr Ser Trp Asn Ser Tyr Ala Asn Met Ile
    130                 135                 140

Tyr Ile Asp Gln Pro Ile Gly Val Gly Phe Ser Tyr Gly Asn Asp Glu
145                 150                 155                 160

Val Val Asp Ser Thr Glu Thr Ala Ala Pro Tyr Val Trp Lys Leu Ile
                165                 170                 175

Gln Ala Phe Tyr Asp Ala Phe Pro Gln Tyr Glu Ser Arg Asp Phe Gly
            180                 185                 190

Ile Phe Thr Glu Ser Tyr Gly Gly His Tyr Gly Pro Glu Phe Ala His
        195                 200                 205

Tyr Ile Gln Asp Gln Asn Asn Gly Ile Ala Ser Gly Ser Val Asp Gly
    210                 215                 220

Gln Lys Ile Asn Leu Ile Ala Leu Gly Val Asn Asn Gly Trp Ile Asp
225                 230                 235                 240

Ala Glu Leu Gln Glu Lys Ala Tyr Ile Asp Tyr Ser Leu Asn Asn Thr
                245                 250                 255

Tyr Lys Lys Ile Ile Ser Gln Ser Glu Ala Thr Ser Tyr Tyr Asn Ala
            260                 265                 270

Tyr Thr Lys Thr Cys Leu Pro Ala Ile Gln Ser Cys Glu Ser Thr Gly
        275                 280                 285
```

-continued

```
Thr Val Ser Ala Cys Val Asn Ala Asp Asn Lys Cys Tyr Asn Ser Ile
    290                 295                 300

Glu Gly Pro Leu Ser Glu Glu Ala Asp Phe Asn Val Tyr Asp Val Arg
305                 310                 315                 320

Ile Gly Ala Ser Val Thr Asp Pro Pro Glu Thr Tyr Ala Asp Tyr Leu
                325                 330                 335

Ala Arg Asp Asp Val Lys Lys Ala Ile Gly Ala Arg Ser Thr Tyr Ser
                340                 345                 350

Glu Cys Ala Asp Thr Pro Tyr Asn Lys Phe Ser Ser Thr Gly Asp Asn
                355                 360                 365

Pro Arg Ser Phe Leu Pro Glu Leu Asn Ser Val Val Gln Ser Gly Leu
    370                 375                 380

Thr Thr Leu Val Trp Ala Gly Asp Ala Asp Trp Ile Cys Asn Trp Met
385                 390                 395                 400

Gly Asn Tyr Asp Ala Ala Gln Ala Val Glu Phe Asp Gly Gln Thr Glu
                405                 410                 415

Phe Arg Ala Ala Ser Leu Glu Pro Tyr Lys Val Asn Gly Val Glu Gly
                420                 425                 430

Gly Thr Phe Lys Thr Val Asp Asn Phe Ser Phe Leu Arg Val Tyr Glu
                435                 440                 445

Ala Gly His Glu Val Pro Tyr Tyr Gln Pro Glu Leu Ala Leu Gln Val
    450                 455                 460

Phe Lys Gln Thr Met Gln Lys Pro Ile Ser Ser Thr
465                 470                 475

<210> SEQ ID NO 9
<211> LENGTH: 2267
<212> TYPE: DNA
<213> ORGANISM: Thermoascus aurantiacus
<220> FEATURE:
<221> NAME/KEY: CDS
<222> LOCATION: (1)..(352)
<220> FEATURE:
<221> NAME/KEY: sig_peptide
<222> LOCATION: (1)..(21)
<220> FEATURE:
<221> NAME/KEY: mat_peptide
<222> LOCATION: (22)..(560)
<220> FEATURE:
<221> NAME/KEY: CDS
<222> LOCATION: (409)..(513)
<220> FEATURE:
<221> NAME/KEY: CDS
<222> LOCATION: (564)..(680)
<220> FEATURE:
<221> NAME/KEY: CDS
<222> LOCATION: (735)..(858)
<220> FEATURE:
<221> NAME/KEY: CDS
<222> LOCATION: (921)..(936)
<220> FEATURE:
<221> NAME/KEY: CDS
<222> LOCATION: (990)..(1106)
<220> FEATURE:
<221> NAME/KEY: CDS
<222> LOCATION: (1162)..(1212)
<220> FEATURE:
<221> NAME/KEY: CDS
<222> LOCATION: (1271)..(1415)
<220> FEATURE:
<221> NAME/KEY: CDS
<222> LOCATION: (1488)..(1546)
<220> FEATURE:
<221> NAME/KEY: CDS
<222> LOCATION: (1612)..(2205)
```

```
<400> SEQUENCE: 9 atg ttg ggc tac ggg ctg ttg ttg ctg cca ttg gca gcg gcc agt ttg      48
Met Leu Gly Tyr Gly Leu Leu Leu Leu Pro Leu Ala Ala Ala Ser Leu
     -5              -1   1               5 gtt cct gca acg ggg gaa cgt gct gtt gtc gac aat gtc cga cga cag      96
Val Pro Ala Thr Gly Glu Arg Ala Val Val Asp Asn Val Arg Arg Gln
 10              15                  20                  25 ctt ccc aag gag cct act gga gtc aaa acc atc acg acc ccg aac aac     144
Leu Pro Lys Glu Pro Thr Gly Val Lys Thr Ile Thr Thr Pro Asn Asn
             30                  35                  40 gtc acc atc cgg tac aaa gag ccc ggg aag gag gga gtc tgc gag acg     192
Val Thr Ile Arg Tyr Lys Glu Pro Gly Lys Glu Gly Val Cys Glu Thr
                 45                  50                  55 act cca gga gta aac tcg tac tcg gga tac atc gac ctc gca ccg gac     240
Thr Pro Gly Val Asn Ser Tyr Ser Gly Tyr Ile Asp Leu Ala Pro Asp
             60                  65                  70 gcg cac acg ttc ttt tgg ttt ttc gaa gcc cgc cac gac ccc gca aat     288
Ala His Thr Phe Phe Trp Phe Phe Glu Ala Arg His Asp Pro Ala Asn
 75                  80                  85 gcg ccg att act ctg tgg ttg aac ggg ggc ccg ggg agt gac tcg ttg     336
Ala Pro Ile Thr Leu Trp Leu Asn Gly Gly Pro Gly Ser Asp Ser Leu
 90                  95                 100                 105 att gga ctc ttt gaa g gtctgctgcg cttgcgaatc gggtgctata tgttgagcgc   392
Ile Gly Leu Phe Glu
             110 agctaacatg tgctag aa  ctc ggt cct tgc ttc atc aac gcc agc tac gaa   443
                     Glu Leu Gly Pro Cys Phe Ile Asn Ala Ser Tyr Glu
                                     115                 120 tct gag atc aac ccg tac tcg tgg agc gaa gtc tcc aat ctg ctc ttc     491
Ser Glu Ile Asn Pro Tyr Ser Trp Ser Glu Val Ser Asn Leu Leu Phe
             125                 130                 135 ctg tca cag ccg ttg ggc gtt g gtatgtgtct gcagtttcga ttggagaagt     543
Leu Ser Gln Pro Leu Gly Val
             140                 145 acgaatctaa tatttggcag gg  ttc tcg tat agc cag aaa gaa cct ggg tcg   595
                         Gly Phe Ser Tyr Ser Gln Lys Glu Pro Gly Ser
                                         150                 155 ctg aac ccc tac acc ggg gtc tac gaa aac gcg tcc ttt gcc ggg gtg     643
Leu Asn Pro Tyr Thr Gly Val Tyr Glu Asn Ala Ser Phe Ala Gly Val
             160                 165                 170 cag ggt cgc tat ccg gtc att gat gcg act att ctt g gtatgttgtc       690
Gln Gly Arg Tyr Pro Val Ile Asp Ala Thr Ile Leu
 175                 180 tgtttgatca gagaccatca ctagaaacta atcataggat atag ac  acc acg gat    745
                                                    Asp Thr Thr Asp
                                                             185 ctc gcc gcc cac gct gcc tgg gaa gcg ctg cag ggc ttc tac agt gcg     793
Leu Ala Ala His Ala Ala Trp Glu Ala Leu Gln Gly Phe Tyr Ser Ala
 190                 195                 200 cta cca cag ctg gac tcg gaa gtc aag tcc aag agc ttc aac ctc tgg     841
Leu Pro Gln Leu Asp Ser Glu Val Lys Ser Lys Ser Phe Asn Leu Trp
205                 210                 215                 220 acg gaa agt tac gga gg gtaagtcaga agacataccc ttgagagtcc            888
Thr Glu Ser Tyr Gly Gly
                 225 tggtctggaa tcttctgtac tgacctaagc ag a cac tat gga cct gct           936
                                     His Tyr Gly Pro Ala
                                                 230 gtgggttgaa cctcaaacaa ttcatgttga tgtcaagact cactccttt tag ttc      992
```

```
                                                                Phe
ttc aat tac ttc cgc gag cag aac gaa aag atc gcc aga ggt gaa gca     1040
Phe Asn Tyr Phe Arg Glu Gln Asn Glu Lys Ile Ala Arg Gly Glu Ala
        235                 240                 245 caa ggc gtc cac ctg gac ttc aac tct ctt ggc ata atc aac ggc att     1088
Gln Gly Val His Leu Asp Phe Asn Ser Leu Gly Ile Ile Asn Gly Ile
250                 255                 260 atc gac gag gct att cag gtgagacctt ttacaaccga atgcgcggac            1136
Ile Asp Glu Ala Ile Gln
265             270 acttaggtag ctcacaggtt gccag gcg agc tac tac ccg gag ttt gct gtg     1188
                            Ala Ser Tyr Tyr Pro Glu Phe Ala Val
                                                275 cat aac acc tat ggc atc aag gct gtaagatata tcgatcttcg aatttcattg    1242
His Asn Thr Tyr Gly Ile Lys Ala
280                 285 gagaacagcc gacgctgaca ggatgcag gtt aac gag act gtt tac aac tac      1294
                                Val Asn Glu Thr Val Tyr Asn Tyr
                                                290                 295 atg aag ttc tcc aac acg ata tgc caa gac cta atc tcg acc tgc aag     1342
Met Lys Phe Ser Asn Thr Ile Cys Gln Asp Leu Ile Ser Thr Cys Lys
                300                 305                 310 aag acg aac agg acg tca ctt gcc gat tac gcc atc tgc tct gag gct     1390
Lys Thr Asn Arg Thr Ser Leu Ala Asp Tyr Ala Ile Cys Ser Glu Ala
            315                 320                 325 acc aac gtg tgc aga gac acc gtg g gtacgtatac catttcgcat             1435
Thr Asn Val Cys Arg Asp Thr Val
        330                 335 agactaggaa gagttgagcc agagaagagt caagactaat aagaccaaaa ag ag  gga   1492
                                                              Glu Gly ccg tac tac acc ttc agc ggc cgt gga acg tac gac atc cgg cac ccg     1540
Pro Tyr Tyr Thr Phe Ser Gly Arg Gly Thr Tyr Asp Ile Arg His Pro
        340                 345                 350 agc cag gtgagtatag aatgataaca gcgacactat ataggaaaga atggacgcga      1596
Ser Gln
355 gctcacgtcg aatag gac ccc acc cca ccc aac ttc ttc ccc gaa tac ctg    1647
                 Asp Pro Thr Pro Pro Asn Phe Phe Pro Glu Tyr Leu
                                 360                 365 aag aag gac tac gtc atg aac gcc atc ggc gtc gac atc aac tac acc     1695
Lys Lys Asp Tyr Val Met Asn Ala Ile Gly Val Asp Ile Asn Tyr Thr
        370                 375                 380 tcc tcc aac tcc gag gtc tac tac gcc ttc cag cag acc ggc gac ttt     1743
Ser Ser Asn Ser Glu Val Tyr Tyr Ala Phe Gln Gln Thr Gly Asp Phe
385                 390                 395 gtc tgg ccc aac ttc atc gac gac ctc gag cag ctc ctc gag ctc ccc     1791
Val Trp Pro Asn Phe Ile Asp Asp Leu Glu Gln Leu Leu Glu Leu Pro
400                 405                 410                 415 gtc cgc atc tcc ctc atc tac ggc gac gcc gac tac atc tgc aac tgg     1839
Val Arg Ile Ser Leu Ile Tyr Gly Asp Ala Asp Tyr Ile Cys Asn Trp
                420                 425                 430 ttc ggc ggc gag gcc gtc tcc ctg gcc gcc aac tac aaa gac gcg gcc     1887
Phe Gly Gly Glu Ala Val Ser Leu Ala Ala Asn Tyr Lys Asp Ala Ala
            435                 440                 445 aag ttc cgc gcc gcg ggc tac acg ccc ctg atc gtc gac ggc gtc gag     1935
Lys Phe Arg Ala Ala Gly Tyr Thr Pro Leu Ile Val Asp Gly Val Glu
        450                 455                 460 tac ggc gag acg cgc gag tac ggc aac ttc tcc ttc acc cgc gtc tac     1983
Tyr Gly Glu Thr Arg Glu Tyr Gly Asn Phe Ser Phe Thr Arg Val Tyr
```

```
                465                 470                 475
gag gcg ggc cac gag gtg ccg tac tac cag ccc atc ccg gcg ctg cag     2031
Glu Ala Gly His Glu Val Pro Tyr Tyr Gln Pro Ile Pro Ala Leu Gln
480                 485                 490                 495 atc ttc aac cgg acg ctc ttc ggg tgg gac att gcc acg ggg acg acc     2079
Ile Phe Asn Arg Thr Leu Phe Gly Trp Asp Ile Ala Thr Gly Thr Thr
                500                 505                 510 aag atc tgg gcg gac tac cgg acc gac ggt tcc ccg aag gcg acg cac     2127
Lys Ile Trp Ala Asp Tyr Arg Thr Asp Gly Ser Pro Lys Ala Thr His
            515                 520                 525 acg gag cct tac gtg ccc ctg ccg acg atc ccg cct aat gcg agt gtc     2175
Thr Glu Pro Tyr Val Pro Leu Pro Thr Ile Pro Pro Asn Ala Ser Val
        530                 535                 540 ggc gtg gcg gcg cag ccg aag tgg gac aga tgaagtcggt gttagtaatc       2225
Gly Val Ala Ala Gln Pro Lys Trp Asp Arg
    545                 550 cgaagaactc atcggccatc tgatctgatc tgatgccatt cc                      2267

<210> SEQ ID NO 10
<211> LENGTH: 560
<212> TYPE: PRT
<213> ORGANISM: Thermoascus aurantiacus

<400> SEQUENCE: 10

Met Leu Gly Tyr Gly Leu Leu Leu Pro Leu Ala Ala Ser Leu
        -5              -1  1               5

Val Pro Ala Thr Gly Glu Arg Ala Val Val Asp Asn Val Arg Arg Gln
10              15                  20                  25

Leu Pro Lys Glu Pro Thr Gly Val Lys Thr Ile Thr Thr Pro Asn Asn
                30                  35                  40

Val Thr Ile Arg Tyr Lys Glu Pro Gly Lys Glu Gly Val Cys Glu Thr
            45                  50                  55

Thr Pro Gly Val Asn Ser Tyr Ser Gly Tyr Ile Asp Leu Ala Pro Asp
        60                  65                  70

Ala His Thr Phe Phe Trp Phe Phe Glu Ala Arg His Asp Pro Ala Asn
    75                  80                  85

Ala Pro Ile Thr Leu Trp Leu Asn Gly Gly Pro Gly Ser Asp Ser Leu
90                  95                  100                 105

Ile Gly Leu Phe Glu Glu Leu Gly Pro Cys Phe Ile Asn Ala Ser Tyr
                110                 115                 120

Glu Ser Glu Ile Asn Pro Tyr Ser Trp Ser Glu Val Ser Asn Leu Leu
            125                 130                 135

Phe Leu Ser Gln Pro Leu Gly Val Gly Phe Ser Tyr Ser Gln Lys Glu
        140                 145                 150

Pro Gly Ser Leu Asn Pro Tyr Thr Gly Val Tyr Glu Asn Ala Ser Phe
    155                 160                 165

Ala Gly Val Gln Gly Arg Tyr Pro Val Ile Asp Ala Thr Ile Leu Asp
170                 175                 180                 185

Thr Thr Asp Leu Ala Ala His Ala Ala Trp Glu Ala Leu Gln Gly Phe
                190                 195                 200

Tyr Ser Ala Leu Pro Gln Leu Asp Ser Glu Val Lys Ser Lys Ser Phe
        205                 210                 215

Asn Leu Trp Thr Glu Ser Tyr Gly Gly His Tyr Gly Pro Ala Phe Phe
    220                 225                 230

Asn Tyr Phe Arg Glu Gln Asn Glu Lys Ile Ala Arg Gly Glu Ala Gln
235                 240                 245
```

```
Gly Val His Leu Asp Phe Asn Ser Leu Gly Ile Ile Asn Gly Ile Ile
250                 255                 260                 265

Asp Glu Ala Ile Gln Ala Ser Tyr Tyr Pro Glu Phe Ala Val His Asn
            270                 275                 280

Thr Tyr Gly Ile Lys Ala Val Asn Glu Thr Val Tyr Asn Tyr Met Lys
        285                 290                 295

Phe Ser Asn Thr Ile Cys Gln Asp Leu Ile Ser Thr Cys Lys Lys Thr
    300                 305                 310

Asn Arg Thr Ser Leu Ala Asp Tyr Ala Ile Cys Ser Glu Ala Thr Asn
315                 320                 325

Val Cys Arg Asp Thr Val Glu Gly Pro Tyr Tyr Thr Phe Ser Gly Arg
330                 335                 340                 345

Gly Thr Tyr Asp Ile Arg His Pro Ser Gln Asp Pro Thr Pro Pro Asn
            350                 355                 360

Phe Phe Pro Glu Tyr Leu Lys Lys Asp Tyr Val Met Asn Ala Ile Gly
        365                 370                 375

Val Asp Ile Asn Tyr Thr Ser Ser Asn Ser Glu Val Tyr Tyr Ala Phe
    380                 385                 390

Gln Gln Thr Gly Asp Phe Val Trp Pro Asn Phe Ile Asp Asp Leu Glu
395                 400                 405

Gln Leu Leu Glu Leu Pro Val Arg Ile Ser Leu Ile Tyr Gly Asp Ala
410                 415                 420                 425

Asp Tyr Ile Cys Asn Trp Phe Gly Gly Glu Ala Val Ser Leu Ala Ala
            430                 435                 440

Asn Tyr Lys Asp Ala Ala Lys Phe Arg Ala Ala Gly Tyr Thr Pro Leu
        445                 450                 455

Ile Val Asp Gly Val Glu Tyr Gly Glu Thr Arg Glu Tyr Gly Asn Phe
    460                 465                 470

Ser Phe Thr Arg Val Tyr Glu Ala Gly His Glu Val Pro Tyr Tyr Gln
475                 480                 485

Pro Ile Pro Ala Leu Gln Ile Phe Asn Arg Thr Leu Phe Gly Trp Asp
490                 495                 500                 505

Ile Ala Thr Gly Thr Thr Lys Ile Trp Ala Asp Tyr Arg Thr Asp Gly
            510                 515                 520

Ser Pro Lys Ala Thr His Thr Glu Pro Tyr Val Pro Leu Pro Thr Ile
        525                 530                 535

Pro Pro Asn Ala Ser Val Gly Val Ala Ala Gln Pro Lys Trp Asp Arg
            540                 545                 550

<210> SEQ ID NO 11
<211> LENGTH: 274
<212> TYPE: PRT
<213> ORGANISM: Bacillus licehniformis

<400> SEQUENCE: 11

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
```

```
                65                  70                  75                  80
Leu Gly Val Ala Pro Ser Val Ser Leu Tyr Ala Val Lys Val Leu Asn
                85                  90                  95
Ser Ser Gly Ser Gly Ser Tyr Ser Gly Ile Val Ser Gly Ile Glu Trp
            100                 105                 110
Ala Thr Thr Asn Gly Met Asp Val Ile Asn Met Ser Leu Gly Gly Ala
            115                 120                 125
Ser Gly Ser Thr Ala Met Lys Gln Ala Val Asp Asn Ala Tyr Ala Arg
        130                 135                 140
Gly Val Val Val Ala Ala Ala Gly Asn Ser Gly Ser Ser Gly Asn
145                 150                 155                 160
Thr Asn Thr Ile Gly Tyr Pro Ala Lys Tyr Asp Ser Val Ile Ala Val
                165                 170                 175
Gly Ala Val Asp Ser Asn Ser Asn Arg Ala Ser Phe Ser Ser Val Gly
                180                 185                 190
Ala Glu Leu Glu Val Met Ala Pro Gly Ala Gly Val Tyr Ser Thr Tyr
            195                 200                 205
Pro Thr Asn Thr Tyr Ala Thr Leu Asn Gly Thr Ser Met Ala Ser Pro
        210                 215                 220
His Val Ala Gly Ala Ala Ala Leu Ile Leu Ser Lys His Pro Asn Leu
225                 230                 235                 240
Ser Ala Ser Gln Val Arg Asn Arg Leu Ser Ser Thr Ala Thr Tyr Leu
                245                 250                 255
Gly Ser Ser Phe Tyr Tyr Gly Lys Gly Leu Ile Asn Val Glu Ala Ala
                260                 265                 270
Ala Gln

<210> SEQ ID NO 12
<211> LENGTH: 269
<212> TYPE: PRT
<213> ORGANISM: Bacillus lentus

<400> SEQUENCE: 12

Ala Gln Ser Val Pro Trp Gly Ile Ser Arg Val Gln Ala Pro Ala Ala
1               5                   10                  15
His Asn Arg Gly Leu Thr Gly Ser Gly Val Lys Val Ala Val Leu Asp
                20                  25                  30
Thr Gly Ile Ser Thr His Pro Asp Leu Asn Ile Arg Gly Gly Ala Ser
            35                  40                  45
Phe Val Pro Gly Glu Pro Ser Thr Gln Asp Gly Asn Gly His Gly Thr
        50                  55                  60
His Val Ala Gly Thr Ile Ala Ala Leu Asn Asn Ser Ile Gly Val Leu
65                  70                  75                  80
Gly Val Ala Pro Ser Ala Glu Leu Tyr Ala Val Lys Val Leu Gly Ala
                85                  90                  95
Ser Gly Ser Gly Ser Val Ser Ser Ile Ala Gln Gly Leu Glu Trp Ala
            100                 105                 110
Gly Asn Asn Gly Met His Val Ala Asn Leu Ser Leu Gly Ser Pro Ser
            115                 120                 125
Pro Ser Ala Thr Leu Glu Gln Ala Val Asn Ser Ala Thr Ser Arg Gly
        130                 135                 140
Val Leu Val Val Ala Ala Ser Gly Asn Ser Gly Ala Gly Ser Ile Ser
145                 150                 155                 160
Tyr Pro Ala Arg Tyr Ala Asn Ala Met Ala Val Gly Ala Thr Asp Gln
```

```
            165                 170                 175
Asn Asn Asn Arg Ala Ser Phe Ser Gln Tyr Gly Ala Gly Leu Asp Ile
        180                 185                 190

Val Ala Pro Gly Val Asn Val Gln Ser Thr Tyr Pro Gly Ser Thr Tyr
    195                 200                 205

Ala Ser Leu Asn Gly Thr Ser Met Ala Thr Pro His Val Ala Gly Ala
210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 13
<211> LENGTH: 268
<212> TYPE: PRT
<213> ORGANISM: Artificial Sequence
<220> FEATURE:
<223> OTHER INFORMATION: variant

<400> SEQUENCE: 13

Gln Thr Val Pro Trp Gly Ile Ser Phe Ile Asn Thr Gln Gln Ala His
1               5                   10                  15

Asn Arg Gly Ile Phe Gly Asn Gly Ala Arg Val Ala Val Leu Asp Thr
            20                  25                  30

Gly Ile Ala Ser His Pro Asp Leu Arg Ile Ala Gly Gly Ala Ser Phe
        35                  40                  45

Ile Ser Ser Glu Pro Ser Tyr His Asp Asn Asn Gly His Gly Thr His
    50                  55                  60

Val Ala Gly Thr Ile Ala Ala Leu Asn Asn Ser Ile Gly Val Leu Gly
65                  70                  75                  80

Val Ala Pro Ser Ala Asp Leu Tyr Ala Val Lys Val Leu Asp Arg Asn
                85                  90                  95

Gly Ser Gly Ser Leu Ala Ser Val Ala Gln Gly Ile Glu Trp Ala Ile
            100                 105                 110

Asn Asn Asn Met His Ile Ile Asn Met Ser Leu Gly Ser Thr Ser Gly
        115                 120                 125

Ser Ser Thr Leu Glu Leu Ala Val Asn Arg Ala Asn Asn Ala Gly Ile
130                 135                 140

Leu Leu Val Gly Ala Ala Gly Asn Thr Gly Arg Gln Gly Val Asn Tyr
145                 150                 155                 160

Pro Ala Arg Tyr Ser Gly Val Met Ala Val Ala Ala Val Asp Gln Asn
                165                 170                 175

Gly Gln Arg Ala Ser Phe Ser Thr Tyr Gly Pro Glu Ile Glu Ile Ser
            180                 185                 190

Ala Pro Gly Val Asn Val Asn Ser Thr Tyr Thr Gly Asn Arg Tyr Val
        195                 200                 205

Ser Leu Ser Gly Thr Ser Met Ala Thr Pro His Val Ala Gly Val Ala
    210                 215                 220

Ala Leu Val Lys Ser Arg Tyr Pro Ser Tyr Thr Asn Asn Gln Ile Arg
225                 230                 235                 240

Gln Arg Ile Asn Gln Thr Ala Thr Tyr Leu Gly Ser Pro Ser Leu Tyr
                245                 250                 255

Gly Asn Gly Leu Val His Ala Gly Arg Ala Thr Gln
```

<210> SEQ ID NO 14
<211> LENGTH: 542
<212> TYPE: PRT
<213> ORGANISM: Aspergillus oryzae

<400> SEQUENCE: 14

```
Met Arg Val Leu Pro Ala Thr Leu Leu Val Gly Ala Ser Ala Ala
1               5                   10                  15

Val Pro Pro Leu Gln Gln Val Leu Gly Arg Pro Glu Gly Met Ser
                20                  25                  30

Phe Ser Lys Pro Leu His Ala Phe Gln Glu Gln Leu Lys Thr Leu Ser
                35                  40                  45

Glu Asp Ala Arg Lys Leu Trp Asp Glu Val Ala Asn Tyr Phe Pro Asp
                50                  55                  60

Ser Met Asp His Ser Pro Ile Phe Ser Leu Pro Lys Lys His Thr Arg
65                  70                  75                  80

Arg Pro Asp Ser His Trp Asp His Ile Val Arg Gly Ser Asp Val Gln
                        85                  90                  95

Lys Ile Trp Val Asn Asn Ala Asp Gly Glu Lys Glu Arg Glu Ile Asp
                100                 105                 110

Gly Lys Leu Glu Ala Tyr Asp Leu Arg Ile Lys Lys Ala Asp Pro Ser
                115                 120                 125

Ala Leu Gly Ile Asp Pro Asn Val Lys Gln Tyr Thr Gly Tyr Leu Asp
                130                 135                 140

Asp Asn Gly Asn Asp Lys His Leu Phe Tyr Trp Phe Phe Glu Ser Arg
145                 150                 155                 160

Asn Asp Pro Lys Asn Asp Pro Val Val Leu Trp Leu Asn Gly Gly Pro
                        165                 170                 175

Gly Cys Ser Ser Leu Thr Gly Leu Phe Met Glu Leu Gly Pro Ser Ser
                180                 185                 190

Ile Asp Glu Asn Ile Lys Pro Val Tyr Asn Asp Phe Ser Trp Asn Ser
                195                 200                 205

Asn Ala Ser Val Ile Phe Leu Asp Gln Pro Val Asn Val Gly Tyr Ser
                210                 215                 220

Tyr Ser Gly Ser Ala Val Ser Asp Thr Val Ala Ala Gly Lys Asp Val
225                 230                 235                 240

Tyr Ala Leu Leu Ser Leu Phe Phe Lys Gln Phe Pro Glu Tyr Ala Glu
                        245                 250                 255

Gln Asp Phe His Ile Ala Gly Glu Ser Tyr Ala Gly His Tyr Ile Pro
                260                 265                 270

Val Phe Ala Ser Glu Ile Leu Ala His Lys Asn Arg Asn Ile Asn Leu
                275                 280                 285

Lys Ser Val Leu Ile Gly Asn Gly Leu Thr Asp Gly Leu Thr Gln Tyr
                290                 295                 300

Gly Tyr Tyr Arg Pro Met Gly Cys Gly Glu Gly Gly Tyr Lys Ala Val
305                 310                 315                 320

Leu Asp Glu Ala Thr Cys Glu Ser Met Asp Asn Ala Leu Pro Arg Cys
                        325                 330                 335

Arg Ser Met Ile Glu Ser Cys Tyr Asn Ser Glu Ser Ala Trp Val Cys
                340                 345                 350

Val Pro Ala Ser Ile Tyr Cys Asn Asn Ala Leu Ile Gly Pro Tyr Gln
                355                 360                 365
```

```
Arg Thr Gly Gln Asn Val Tyr Asp Val Arg Ser Lys Cys Glu Asp Glu
    370                 375                 380

Ser Asn Leu Cys Tyr Lys Gly Met Gly Tyr Val Ser Glu Tyr Leu Asn
385                 390                 395                 400

Lys Ala Glu Val Arg Glu Ala Val Gly Ala Glu Val Gly Gly Tyr Asp
                405                 410                 415

Ser Cys Asn Phe Asp Ile Asn Arg Asn Phe Leu Phe His Gly Asp Trp
            420                 425                 430

Met Lys Pro Tyr His Arg Leu Val Pro Gly Leu Leu Glu Gln Ile Pro
                435                 440                 445

Val Leu Ile Tyr Ala Gly Asp Ala Asp Tyr Ile Cys Asn Trp Leu Gly
    450                 455                 460

Asn Lys Ala Trp Thr Glu Ala Leu Glu Trp Pro Gly Gln Lys Glu Tyr
465                 470                 475                 480

Ala Ser Ala Glu Leu Glu Asp Leu Lys Ile Glu Gln Asn Glu His Thr
                485                 490                 495

Gly Lys Lys Ile Gly Gln Val Lys Ser His Gly Asn Phe Thr Phe Met
                500                 505                 510

Arg Leu Tyr Gly Gly Gly His Met Val Pro Met Asp Gln Pro Glu Ala
                515                 520                 525

Ser Leu Glu Phe Phe Asn Arg Trp Leu Gly Gly Glu Trp Phe
530                 535                 540

<210> SEQ ID NO 15
<211> LENGTH: 558
<212> TYPE: PRT
<213> ORGANISM: Aspergillus oryzae

<400> SEQUENCE: 15

Cys Pro Tyr Met Arg Gly Tyr Glu Phe Leu Ser Val Leu Pro Leu Val
1               5                   10                  15

Ala Ala Ser Trp Ala Leu Pro Gly Ser Thr Pro Ala Ser Val Gly Arg
                20                  25                  30

Arg Gln Leu Pro Lys Asn Pro Thr Gly Val Lys Thr Leu Thr Thr Ala
            35                  40                  45

Asn Asn Val Thr Ile Arg Tyr Lys Glu Pro Gly Ala Glu Gly Val Cys
50                  55                  60

Glu Thr Thr Pro Gly Val Lys Ser Tyr Ser Gly Tyr Val Asp Thr Ser
65                  70                  75                  80

Pro Glu Ser His Thr Phe Phe Trp Phe Phe Glu Ala Arg His Asn Pro
                85                  90                  95

Glu Thr Ala Pro Ile Thr Leu Trp Leu Asn Gly Gly Pro Gly Ser Asp
                100                 105                 110

Ser Leu Ile Gly Leu Phe Glu Glu Leu Gly Pro Cys His Val Asn Ser
            115                 120                 125

Thr Phe Asp Asp Tyr Ile Asn Pro His Ser Trp Asn Glu Val Ser Asn
130                 135                 140

Leu Leu Phe Leu Ser Gln Pro Leu Gly Val Gly Phe Ser Tyr Ser Asp
145                 150                 155                 160

Thr Val Asp Gly Ser Ile Asn Pro Val Thr Gly Val Val Glu Asn Ser
                165                 170                 175

Ser Phe Ala Gly Val Gln Gly Arg Tyr Pro Thr Ile Asp Ala Thr Leu
            180                 185                 190

Ile Asp Thr Thr Asn Leu Ala Ala Glu Ala Ala Trp Glu Ile Leu Gln
            195                 200                 205
```

Gly Phe Leu Ser Gly Leu Pro Ser Leu Asp Ser Arg Val Gln Ser Lys
210                 215                 220

Asp Phe Ser Leu Trp Thr Glu Ser Tyr Gly His Tyr Gly Pro Ala
225                 230                 235                 240

Phe Phe Asn His Phe Tyr Glu Gln Asn Glu Arg Ile Ala Asn Gly Ser
                245                 250                 255

Val Asn Gly Val Gln Leu Asn Phe Asn Ser Leu Gly Ile Ile Asn Gly
            260                 265                 270

Ile Ile Asp Glu Ala Ile Gln Ala Pro Tyr Tyr Pro Glu Phe Ala Val
        275                 280                 285

Asn Asn Thr Tyr Gly Ile Lys Ala Val Asn Glu Thr Val Tyr Asn Tyr
    290                 295                 300

Met Lys Phe Ala Asn Gln Met Pro Asn Gly Cys Gln Asp Leu Ile Ser
305                 310                 315                 320

Thr Cys Lys Gln Thr Asn Arg Thr Ala Leu Ala Asp Tyr Ala Leu Cys
                325                 330                 335

Ala Glu Ala Thr Asn Met Cys Arg Asp Asn Val Glu Gly Pro Tyr Tyr
            340                 345                 350

Ala Phe Ala Gly Arg Gly Val Tyr Asp Ile Arg His Pro Tyr Asp Asp
        355                 360                 365

Pro Thr Pro Pro Ser Tyr Tyr Asn Lys Phe Leu Ala Lys Asp Ser Val
370                 375                 380

Met Asp Ala Ile Gly Val Asn Ile Asn Tyr Thr Gln Ser Asn Asn Asp
385                 390                 395                 400

Val Tyr Tyr Ala Phe Gln Gln Thr Gly Asp Phe Val Trp Pro Asn Phe
                405                 410                 415

Ile Glu Asp Leu Glu Glu Ile Leu Ala Leu Pro Val Arg Val Ser Leu
            420                 425                 430

Ile Tyr Gly Asp Ala Asp Tyr Ile Cys Asn Trp Phe Gly Gly Gln Ala
        435                 440                 445

Val Ser Leu Ala Ala Asn Tyr Ser Gln Ala Ala Gln Phe Arg Ser Ala
    450                 455                 460

Gly Tyr Thr Pro Leu Lys Val Asn Gly Val Glu Tyr Gly Glu Thr Arg
465                 470                 475                 480

Glu Tyr Gly Asn Phe Ser Phe Thr Arg Val Tyr Glu Ala Gly His Glu
                485                 490                 495

Val Pro Tyr Tyr Gln Pro Ile Ala Ser Leu Gln Leu Phe Asn Arg Thr
            500                 505                 510

Ile Phe Gly Trp Asp Ile Ala Glu Gly Gln Lys Lys Ile Trp Pro Ser
        515                 520                 525

Tyr Lys Thr Asn Gly Thr Ala Thr Ala Thr His Thr Gln Ser Ser Val
    530                 535                 540

Pro Leu Pro Thr Ala Thr Ser Met Ser Ser Val Gly Met Ala
545                 550                 555

<210> SEQ ID NO 16
<211> LENGTH: 496
<212> TYPE: PRT
<213> ORGANISM: Aspergillus oryzae

<400> SEQUENCE: 16

Met Arg Ser Leu Leu Trp Ala Ser Leu Leu Ser Gly Val Leu Ala Gly
1               5                   10                  15

Arg Ala Leu Val Ser Pro Asp Glu Phe Pro Glu Asp Ile Gln Leu Glu

```
                20                  25                  30
Asp Leu Leu Glu Gly Ser Gln Gln Leu Glu Asp Phe Ala Tyr Ala Tyr
            35                  40                  45
Pro Glu Arg Asn Arg Val Phe Gly Lys Ala His Asp Asp Thr Val
 50                  55                  60
Asn Tyr Leu Tyr Glu Glu Leu Lys Lys Thr Gly Tyr Tyr Asp Val Tyr
 65                  70                  75                  80
Lys Gln Pro Gln Val His Leu Trp Ser Asn Ala Asp Gln Thr Leu Lys
                85                  90                  95
Val Gly Asp Glu Glu Ile Glu Ala Lys Thr Met Thr Tyr Ser Pro Ser
            100                 105                 110
Val Glu Val Thr Ala Asp Val Ala Val Lys Asn Leu Gly Cys Ser
            115                 120                 125
Glu Ala Asp Tyr Pro Ser Asp Val Glu Gly Lys Val Ala Leu Ile Lys
            130                 135                 140
Arg Gly Glu Cys Pro Phe Gly Asp Lys Ser Val Leu Ala Ala Lys Ala
145                 150                 155                 160
Lys Ala Ala Ala Ser Ile Val Tyr Asn Asn Val Ala Gly Ser Met Ala
                165                 170                 175
Gly Thr Leu Gly Ala Ala Gln Ser Asp Lys Gly Pro Tyr Ser Ala Ile
            180                 185                 190
Val Gly Ile Ser Leu Glu Asp Gly Gln Lys Leu Ile Lys Leu Ala Glu
            195                 200                 205
Ala Gly Ser Val Ser Val Asp Leu Trp Val Asp Ser Lys Gln Glu Asn
            210                 215                 220
Arg Thr Thr Tyr Asn Val Val Ala Gln Thr Lys Gly Gly Asp Pro Asn
225                 230                 235                 240
Asn Val Val Ala Leu Gly Gly His Thr Asp Ser Val Glu Ala Gly Pro
                245                 250                 255
Gly Ile Asn Asp Asp Gly Ser Gly Ile Ile Ser Asn Leu Val Ile Ala
            260                 265                 270
Lys Ala Leu Thr Gln Tyr Ser Val Lys Asn Ala Val Arg Phe Leu Phe
            275                 280                 285
Trp Thr Ala Glu Glu Phe Gly Leu Leu Gly Ser Asn Tyr Tyr Val Ser
            290                 295                 300
His Leu Asn Ala Thr Glu Leu Asn Lys Ile Arg Leu Tyr Leu Asn Phe
305                 310                 315                 320
Asp Met Ile Ala Ser Pro Asn Tyr Ala Leu Met Ile Tyr Asp Gly Asp
                325                 330                 335
Gly Ser Ala Phe Asn Gln Ser Gly Pro Ala Gly Ser Ala Gln Ile Glu
            340                 345                 350
Lys Leu Phe Glu Asp Tyr Tyr Asp Ser Ile Asp Leu Pro His Ile Pro
            355                 360                 365
Thr Gln Phe Asp Gly Arg Ser Asp Tyr Glu Ala Phe Ile Leu Asn Gly
            370                 375                 380
Ile Pro Ser Gly Gly Leu Phe Thr Gly Ala Glu Gly Ile Met Ser Glu
385                 390                 395                 400
Glu Asn Ala Ser Arg Trp Gly Gly Gln Ala Gly Val Ala Tyr Asp Ala
                405                 410                 415
Asn Tyr His Ala Ala Gly Asp Asn Met Thr Asn Leu Asn His Glu Ala
            420                 425                 430
Phe Leu Ile Asn Ser Lys Ala Thr Ala Phe Ala Val Ala Thr Tyr Ala
            435                 440                 445
```

```
Asn Asp Leu Ser Ser Ile Pro Lys Arg Asn Thr Thr Ser Ser Leu His
        450                 455                 460

Arg Arg Ala Arg Thr Met Arg Pro Phe Gly Lys Arg Ala Pro Lys Thr
465                 470                 475                 480

His Ala His Val Ser Gly Ser Gly Cys Trp His Ser Gln Val Glu Ala
                485                 490                 495

<210> SEQ ID NO 17
<211> LENGTH: 39
<212> TYPE: DNA
<213> ORGANISM: Penicillium emersonii

<400> SEQUENCE: 17
acacaactgg ggatccacca tgagagttct tcctgcgac                           39

<210> SEQ ID NO 18
<211> LENGTH: 35
<212> TYPE: DNA
<213> ORGANISM: Penicillium emersonii

<400> SEQUENCE: 18
ccctctagat ctcgaggaac gcgacacgct tctca                               35

<210> SEQ ID NO 19
<211> LENGTH: 40
<212> TYPE: DNA
<213> ORGANISM: Thermoascus aurantiacus

<400> SEQUENCE: 19
acacaactgg ggatccacca tgttgggcta cgggctgttg                          40

<210> SEQ ID NO 20
<211> LENGTH: 40
<212> TYPE: DNA
<213> ORGANISM: Thermoascus aurantiacus

<400> SEQUENCE: 20
ccctctagat ctcgagggaa tggcatcaga tcagatcaga                          40
```

POLYNUCLEOTIDE ENCODING POLYPEPTIDE HAVING CARBOXYPEPTIDASE ACTIVITY

CROSS-REFERENCE TO RELATED APPLICATIONS

This application is a 35 U.S.C. 371 national application of international application no. PCT/CN2018/090425 filed Jun. 8, 2018, which claims priority or the benefit under 35 U.S.C. 119 of international application nos. PCT/CN2017/087723 filed Jun. 9, 2017. The content of each application is fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to a method for producing a protein hydrolysate using a polypeptide having endopeptidase activity and a polypeptide having carboxypeptidase activity and the use of these enzymes for hydrolysing a protein substrate. In addition the present invention relates to polypeptides having carboxypeptidase activity and polynucleotides encoding the polypeptides. The invention also relates to nucleic acid constructs, vectors, and host cells comprising the polynucleotides as well as methods of producing and using the polypeptides.

Description of the Related Art

Protein hydrolysates are used as an additive or ingredient in various food products. The advantages of using protein hydrolysates in food products are reduced allergenicity, easier digestion and absorbtion and thereby also faster absorption of the nutrients. Such products can be used in medical nutrition, infant nutrition, health foods, sports nutritions or can be used for enhancing the protein content of the food product. Also protein hydrolysates are used for enhancing the flavour of the food product e.g. by adding umami taste to the product.

Conventionally, protein hydrolysates are produced chemically by hydrolysing protein (e.g. defatted soy flour or wheat gluten) with hydrochloric acid. The hydrolysates are cheap to produce, but the chemical hydrolysis results in byproducts, which are undesirable in food products.

An alternative method for hydrolysing protein is enzymatic hydrolysis, where protein substrate is subjected to peptidases, e.g. as Flavourzyme® (Novozymes) or Alcalase® (Novozymes). The peptidases used for hydrolysing can be either endopeptidases or exopeptidases, where the exopeptidases are categorised in aminopeptidases and carboxypeptidases. Endoproteases attack proteins and peptides within the molecule. Exoproteases attack from the terminal of the molecule, where aminopeptidases and carboxypeptidases cleaves off amino acids or peptides from the protein substrate from the amino-terminal end or the carboxy-terminal end, respectively.

International patent application WO2016/210395 concerns use of aminopeptidases for producing protein hydrolysate. EP0946106 describes a method for producing a protein hydrolysate with a proteolytic enzyme mixture comprising only one exo-peptidase.

SUMMARY OF THE INVENTION

The invention provides a method for producing a protein hydrolysate which method comprises:
a. providing an aqueous solution or suspension of a protein substrate; and
b. exposing the aqueous solution or suspension of the protein substrate to a polypeptide having endopeptidase activity and to a polypeptide having carboxypeptidase activity, to obtain the protein hydrolysate;
wherein the polypeptide having carboxypeptidase activity is characterised by having a Pro/ACHA*100 ratio of at least 30.

The present invention provides polypeptides having carboxypeptidase activity and polynucleotides encoding the polypeptides.

Accordingly, the present invention relates to polypeptides having carboxypeptidase activity selected from the group consisting of:
a. a polypeptide having at least 60% sequence identity to the mature polypeptide of SEQ ID NO: 2, SEQ ID NO: 4 or SEQ ID NO: 6, SEQ ID NO: 8, SEQ ID NO; 10;
b. a polypeptide encoded by a polynucleotide having at least 60% sequence identity to the mature polypeptide coding sequence of SEQ ID NO: 1, SEQ ID NO: 3 or SEQ ID NO: 5, SEQ ID NO: 7, SEQ ID NO: 9 or the cDNA sequence thereof;
c. a variant of the mature polypeptide of SEQ ID NO: 2, SEQ ID NO: 4, SEQ ID NO: 6, SEQ ID NO: 8 or SEQ ID NO: 10 comprising a substitution, deletion, and/or insertion at one or more positions; and
d. a fragment of the polypeptide of (a), (b) or (c) that has carboxypeptidase activity.

The invention further concerns a liquid or granulate composition comprising the polypeptide of the invention. And the invention concerns a whole broth formulation or cell culture composition comprising the polypeptide of the invention.

The invention also concerns a polynucleotide encoding the inventive polypeptide, a nucleoic acid construct or expression vector comprising the polynucleotide.

DEFINITIONS

ACHA—Average Carboxypeptidase Hydrophobic Activity

Based on the activities measured in Assay II, the ACHA can be calculated as the the average of the specific activity of the carboxypeptidase on the following substrates: Z-Ala-Ala-OH, Z-Ala-Val-OH, Z-Ala-Ile-OH, Z-Ala-Leu-OH, Z-Ala-Met-OH, Z-Ala-Phe-OH and Z-Ala-Trp-OH. Z-Ala-Pro-OH is not included in this calculation.

ACLA—Average Carboxypeptidase Activity for Lysine and Arginine

Based on the activities measured in Assay II, the ACLA can be calculated as the average of the specific activity of the carboxypeptidase on the following two substrates: Z-Ala-Lys-OH, Z-Ala-Arg-OH.

Pro/ACHA*100 Ratio—Pro/Average Carboxypeptidase Hydrofobic Activity (ACHA) Ratio Based on the activities measured in Assay I and Assay II and the calculation of ACHA, the Pro/ACHA*100 ratio can be calculated as the activity on Pro as measured in Assay I divided by ACHA (the average of the activity on the hydrophobic amino acids Ala, Val, Ile, Met, Phe, Leu and Trp measured in Assay II) and multiplied with 100, Carboxypeptidase or Polypeptide Having Carboxypeptidase Activity:

The term "carboxy-peptidase" means a protein or a polypeptide having carboxypeptidase activity (3.4.16.X, 3.4.17.X, 3.4.18.X) that catalyzes the cleavage of the peptide bond at the carboxy-terminal end of the protein or peptide. For purposes of the present invention, carboxypeptidase activity is determined according to the procedure described in the Assay II, where a polypeptide having carboxypeptidase activity is capable of cleaving at least one of the substrates in the assay (e.g. Z-Ala-Val-OH). In one aspect, the polypeptides of the present invention have at least 20%, e.g., at least 40%, at least 50%, at least 60%, at least 70%, at least 80%, at least 90%, at least 95%, or at least 100% of the carboxypeptidase activity of the mature polypeptide of SECS ID NO: 2, 4, 6, 8 or 10. The terms "polypeptide having carboxypeptidase activity" and "carboxypeptidase" are used interchangeably.

Endopeptidase, Endoprotease or Polypeptide Having Endopeptidase Activity:

The term "endopeptidase" means a protein or a polypeptide having endopeptidase activity (3.4.19.X, 3.4.21.X, 3.4.22.X, 3.4.23.X, 3.4.24.X, 3.4.25.X) that catalyzes the cleavage of the peptide bonds within the protein or peptide molecule. For purposes of the present invention, endopeptidase activity is determined according to the procedure described in Assay III. The terms "polypeptide having endopeptidase activity", "endoprotease" and "endopeptidase" are used interchangeably.

Aminopeptidase or Polypeptide Having Aminopeptidase Activity:

The term "aminopeptidase" means a protein or a polypeptide having aminopeptidase activity (3.4.11.X) that catalyzes the cleavage of the peptide bond at the amino-terminal end of the protein or peptide. For purposes of the present invention, aminopeptidase activity is determined according to the procedure described in the Assay IV. The terms "polypeptide having aminopeptidase activity" and "aminopeptidase" are used interchangeably.

Allelic Variant:

The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA:

The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding Sequence:

The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control Sequences:

The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression:

The term "expression" includes any step involved in the production of a polypeptide including, but not limited to, transcription, post-transcriptional modification, translation, post-translational modification, and secretion.

Expression Vector:

The term "expression vector" means a linear or circular DNA molecule that comprises a polynucleotide encoding a polypeptide and is operably linked to control sequences that provide for its expression.

Fragment:

The term "fragment" means a polypeptide or a catalytic or carboxypeptidase binding domain having one or more (e.g., several) amino acids absent from the amino and/or carboxyl terminus of a mature polypeptide or domain; wherein the fragment has carboxypeptidase activity.

Host Cell:

The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated:

The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the invention. The fermentation broth from that host cell will comprise the isolated polypeptide.

Mature Polypeptide:

The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1-426 of SEQ ID NO: 2, amino acids 1-443 of SEQ ID NO: 4, amino acids 1-444 of SEQ ID NO: 6, amino acids 1-477 SEQ ID NO: 8 or amino acids 1-553 of SEQ ID NO: 10.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature Polypeptide Coding Sequence:

The term "mature polypeptide coding sequence" means a polynucleotide that encodes a mature polypeptide having carboxypeptidase activity. In one aspect, the mature polypeptide coding sequence is nucleotides 358 to 1687 of SEQ ID NO: 1 and nucleotides 1 to 45 of SEQ ID NO: 1 encode a signal peptide.

Nucleic Acid Construct:

The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably Linked:

The term "operably linked" means a configuration in which a control sequence is placed at an appropriate position relative to the coding sequence of a polynucleotide such that the control sequence directs expression of the coding sequence.

Sequence Identity:

The relatedness between two amino acid sequences or between two nucleotide sequences is described by the parameter "sequence identityFor purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment− Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Variant: The term "variant" means a polypeptide having carboxypeptidase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

DETAILED DESCRIPTION OF THE INVENTION

The present invention concerns a method for producing a protein hydrolysate comprising:
a. providing an aqueous solution or suspension of a protein substrate; and
b. exposing the aqueous solution or suspension of the protein substrate to a polypeptide having endopeptidase activity and polypeptide having carboxypeptidase activity to obtain the protein hydrolysate;
   wherein the polypeptide having carboxypeptidase activity is characterised by having a Pro/ACHA*100 ratio of at least 30.

By the use of two different polypeptides, a polypeptide having endopeptidase activity and a polypeptide having carboxypeptidase activity, the protein substrate is attacked in two different ways. The polypeptide having endopeptidase activity attacks the protein substrate by cleaving the peptide bonds within the protein molecule, whereby the protein substrate is hydrolysed to smaller peptides, which can be attacked by the polypeptide having carboxypeptidase activity. The method thereby provides protein hydrolysates with a high degree of hydrolysis, which are suitable for use in various products, e.g. food products, cosmetic products, medical products.

Any type of protein substrate can be used for protein hydrolysis. Usually the applications of the protein hydrolysate determines the type of protein substrate used. The protein substrate can be from animal or vegetable source. In one embodiment the animal protein is selected from milk protein such as casein or whey proteins.

In one embodiment the protein substrate is a vegetable protein selected from the group consisting of cereal, legumes and oilseed. The protein substrate can be from a cereal such as wheat, barley, oat, rye, triticale, maize, rice, sorghum, buckwheat, quinoa, Chia, millet or fonio. In a preferred embodiment, the protein is gluten. In a particularly preferred embodiment, the protein is wheat gluten. Another source of vegetable protein is legumes, where the protein can be from peas, beans, lentils or chick peas. Protein from oilseeds can be used in the inventive method e.g. soy bean, cotton seed, peanut, rape seed, sunflower seed, palm kernel, coconut, corn, safflower seed, sunflower seed and lin seed. In a preferred embodiment the protein substrate is soy protein. The soy protein can be defatted soy (e.g. flakes or flour), soy protein concentrates and soy isolates. The protein content in defatted soy products accounts for 50% of the dry matter, whereas soy protein concentrates and soy isolates may contain 70% protein and 90% protein, respectively.

The concentration of the protein substrate in the aqueous solution or suspension should be in the range of 5-35% depending on which protein substrate that is used.

In one embodiment of the invention the concentration of the protein substrate is in the range of 5-30%, in the range of 5-25%, in the range of 5-20%, in the range of 5-15% or in the range of 10-15%.

The concentration of the polypeptides used in the method depends on the amount of protein substrate used. In one embodiment of the invention the concentration of the polypeptide having carboxypeptidase activity is in the range of 0.01-4 mg enzyme protein/gram protein substrate. In one embodiment of the invention the concentration of polypeptide is in the range of 0.01-3.9 mg enzyme protein/gram protein substrate, such as in the range of 0.1-3.8 mg enzyme protein/gram protein substrate, in the range of 0.1-3.6, in the range of 0.2-3.4, in the range of 0.2-3.2, in the range of 0.3-3.0, in the range of 0.3-2.8, in the range of 0.4-2.6, in the range of 0.4-2.4, in the range of 0.5-2.2, in the range of 0.5-2.0.

In one embodiment of the invention, the concentration of the polypeptide having endopeptidase activity is in the range of 0.1-3.0% w/w on protein, such as is in the range of 0.1-2.8% w/w on protein, such as in the range of 0.1-2.6% w/w on protein, in the range of 0.1-2.4% w/w on protein, in the range of 0.1-2.2% w/w on protein, in the range of 0.1-2.0% w/w on protein, in the range of 0.1-1.8% w/w on protein, in the range of 0.1-1.6% w/w on protein, in the range of 0.1-1.4% w/w on protein, in the range of 0.1-1.2% w/w on protein, in the range of 0.1-1.0% w/w on protein, in the range of 0.2-1.0% w/w on protein, in the range of 0.3-1.0% w/w on protein, in the range of 0.4-1.0% w/w on protein or in the range of 0.5-1.0% w/w on pro.

The polypeptide having carboxypeptidase activity used in the inventive method can be any polypeptide having carboxypeptiddase activity and which has a Pro/ACHA*100 ratio of at least 30. The Pro/ACHA*100 ratio is at least 35, at least at least 40, such as at least 41, at least 42, at least 45, at least 50, at least 51, at least 50, at least 52, at least 53, at least 54, at least 55, at least 56, at least 57, at least 58, at least 59, at least 60 or at least 61.

Some polypeptide having carboxypeptide activity may have an activity on Proline when measured with Assay I of at least 0.15. In one embodiment of the invention the activity on Proline when measured with Assay I is at least at least at least 0.16, at least 0.17, at least 0.18, at least 0.19, at least 0.2, at least 0.21, at least 0.22, at least 0.23, at least 0.24, at least 0.25, at least 0.3, at least 0.35, at least 0.4, at least 0.45, at least 0.5, at least 0.55, at least 0.6 or at least 0.625.

The polypeptides having carboxypeptidase activity tend to have a higher activity on hydrophobic amino acids. In one embodiment the polypeptide having carboxypeptiddase activity has an average hydrophobic activity of at least 0.51 when measured in Assay II.

In one embodiment, the polypeptide having carboxypeptidase activity has an ACHA value of at least 0.52 when measured in Assay II, such as at least 0.53, at least 0.54, at least 0.56, at least 0.57, at least 0.58 or at least 0.59.

Some polypeptides having carboxypeptidase activity may have an an ACLA value in the range of 0.16-0.25, such as in the range of 0.17-0.25, in the range of 0.18-0.25, in the range of 0.19-0.25.

Specific polypeptides having carboxypeptidase activity which may be used in the inventive method are described in the below.

When producing a protein hydrolysate according to the invention, the temperature of the aqueous solution/suspension comprising the protein substrate should be within the temperature range where the enymes work, so the temperature should be above 5° C. or above 10° C. In one embodiment, the temperature is in the range of 10-90° C., such as in the range of 20-80° C., in the range of 30-70° C., in the range of 40-60° C., in the range of 45-55° C. or in the range of 50-60° C.

In the inventive method, the protein substrate is exposed to the polypeptide having endopeptidase activity and the polypeptide having carboxypeptidase activity for at least 4 hours. In one embodiment the protein substrate is exposed to the polypeptide having endopeptidase activity and the polypeptide having carboxypeptidase activity for 3-48 hours, such as 4-48 hours, 4-36 hours, 6-32 hours, 8-28 hours, 10-26 hours, 12-24 hours, 12-22 hours, 12-20 hours, 12-18 hours, 12-16 hours or for 12-14 hours.

The pH of the aqueous solution/suspension is in the range of 5-8, such as in the range of 5.5-6.5 or in the range of 6.0-7.0.

When producing the protein hydrolysate, the aqueous solution/suspension comprising the protein substrate should be exposed to the polypeptide having endopeptidase activity and the polypeptide having carboxypeptidase activity either at the same time, or the protein substrate should be exposed to the polypeptide having endopeptidase activity first. The advantage of adding the polypeptide having endopeptidase activity to the aqueous solution/suspension comprising the protein substrate first, is that the polypeptide having endopeptidase activity can hydrolyse the protein substrate and cut into peptides, which are available for the polypeptide having carboxypeptidase activity to hydrolyse.

The hydrolysis can be stopped when the hydrolysed proteins have the desired degree of hydrolysis, however by the inventive method protein hydrolysates with a high degree of hydrolysis can be produced. In one embodiment, the method is carried out until the obtained protein hydrolysate has a degree of hydrolysis (% DH) in the range of 40%-70%, such as in the range of 45%-70%, in the range of 50%-70%, in the range of 55%-70%, in the range of 60%70%, in the range of 65%-70%.

The polypeptide having endopeptidase activity may be obtained from a strain of *Bacillus*, preferably *Bacillus licheniformis* or *Bacillus subtilis*, a strain of *Staphylococcus*, preferably *Staphylococcus aureus*. Or the polypeptide having endopeptidase activity may be obtained from fungal source, e.g. a strain of *Streptomyces*, preferably *Streptomyces thermovularis* or *Streptomyces griseus*, a strain of *Actinomyces* species, a strain of *Aspergillus*, preferably *Aspergillus aculeates, Aspergillus awamori, Aspergillus foetidus, Aspergillus nidulans, Aspergillus niger*, ox *Aspergillus oryzae*, or a strain of *Trichoderma*, preferably *Trichoderma reesei*, or *Fusarium*, preferably *Fusarium venenatum*. The polypeptide having endopeptidase activity may be a substilisin. In some embodiments, the endopeptidase is comprised in the products Alcalase® (Novozymes A/S), Flavourzyme® (Novozymes A/S), Savinase® (Novozymes A/S), Esperase® (Novozymes A/S), Alphalase® (Dupont).

The protein substrate can be hydrolysed to an even higher degree of hydrolysis by exposing the protein substrate to a polypeptide having aminopeptidase activity or a fermentation broth supernatant of an *Aspergillus* strain having aminopeptidase activity. Amino peptidase 2 described in WO2016/210395 (Dupont Nutrition Biosciences APS) can be used in the present invention, especially aminopeptidase 2 defined in SEQ ID Nos: 1-8 or WO2016/210395 is preferred. Other suitable aminopeptidases are described in WO97/29179 (Gist Brocades BV) and WO2003/102195 (DSM IP Assets BV). The protein substrate may be exposed to the polypeptide having aminopeptidase activity at the same time as being exposed to the polypeptide having endopeptidase activity. In one embodiment of the invention, the protein substrate is exposed to the polypeptide having endopeptidase activity and then subsequently to the polypeptide having carboxypeptidase activity and the polypeptide having aminopeptidase activity. In one embodiment, the protein substrate is exposed to the polypeptide having aminopeptidase activity before, simultaneously or after the protein substrate is exposed to the polypeptide having carboxypeptidase activity.

The concentration of the polypeptide having aminopeptidase activity should be in the range of 0.05-4 mg enzyme protein per gram protein substrate. In one embodiment, the concentration of the polypeptide having aminopeptidase activity may be 0.05-3.5 mg enzyme protein per gram protein substrate, such as 0.05-3.0 mg enzyme protein per gram protein substrate, 0.05-2.5 mg enzyme protein per gram protein substrate, 0.05-2.0 mg enzyme protein per gram protein substrate, 0.06-2.0 mg enzyme protein per gram protein substrate, 0.07-2.0 mg enzyme protein per gram protein substrate, 0.08-2.0 mg enzyme protein per gram protein substrate, 0.09-2.0 mg enzyme protein per gram protein substrate or 0.1-2.0 mg enzyme protein per gram protein substrate.

In one embodiment, the invention concerns an isolated polypeptide having carboxypeptidase activity, selected from the group consisting of:

a. a polypeptide having [at least 60% sequence identity to the mature polypeptide of SEQ ID NO: 2, SEQ ID NO: 4 or SEQ ID NO: 6, SEQ ID NO: 8, SEQ ID NO: 10;

b. a polypeptide encoded by a polynucleotide having at least 60% sequence identity to the mature polypeptide coding sequence of SEQ ID NO: 1, SEQ ID NO: 3 or SEQ ID NO: 5, SEQ ID NO: 7, SEQ ID NO: 9 [if SEQ ID NO: 1, 3, 5 does not contain any introns, then end (b) here. Otherwise, insert: or the cDNA sequence thereof];

c. a variant of the mature polypeptide of SEQ ID NO: 2, SEQ ID NO: 4, or SEQ ID NO: 6, SEQ ID NO: 8 or SEQ ID NO: 10 comprising a substitution, deletion, and/or insertion at one or more positions; and d. a fragment of the polypeptide of (a), (b) or, (c), or (d) that has carboxypeptidase activity.

In one embodiment, the invention concerns a protein hydrolysate produced by the inventive method.

In one embodiment, the invention concerns a protein hydrolysate comprising free amino acids, wherein the amount of free amino acids is at least 20 g per 100 gram protein, the total amount of Ala, Val, Ile, Leu, Met, Phe and Trp is at least 7 g per 100 g protein and at least 1.0 g Pro per 100 g protein.

In one embodiment, the amount of free amino acids is at least 25 g per 100 g protein hydrolysate, such as at least 30 g per 100 g hydrolysate, at least 30 g per 100 g hydrolysate, at least 35 g per 100 g hydrolysate or at least 40 g per 100 g hydrolysate.

In one embodiment, the amount of Ala, Val, Ile, Leu, Met, Phe and Trp is at least 13 g per 100 g protein substrate and at least 1.8 g per 100 g protein hydrolysate.

In one embodiment, the hydrolysate further has a degree of hydrolysation (% dH) in the range of 30%-70%, such as in the range of 45%-70%, in the range of 50%-70%, in the range of 55%-70%, in the range of 60%-70%, in the range of 65%-70%.

Overview of Sequences Listing

SEQ ID NO: 1 is the sequence of a polynucleotide derived from *Penicillium emersonii*.

SEQ ID NO: 2 is the amino acid sequence of the polypeptide encoded by SEQ ID NO: 1.

SEQ ID NO: 3 is the sequence of a polynucleotide derived from *Myceliophthora heterothallica*.

SEQ ID NO: 4 is the amino acid sequence of the polypeptide encoded by SEQ ID NO: 3.

SEQ ID NO: 5 is the sequence of a polynucleotide derived from *Chaetomium strumarium*.

SEQ ID NO: 6 is the amino acid sequence of the polypeptide encoded by SEQ ID NO: 5.

SEQ ID NO: 7 is the sequence of a polynucleotide derived from *Lasiodiplodia theobromae*.

SEQ ID NO: 8 is the amino acid sequence of the polypeptide encoded by SEQ ID NO: 7.

SEQ ID NO: 9 is the sequence of a polynucleotide derived from *Thermoascus aurantiacus*.

SEQ ID NO: 10 is the amino acid sequence of the polypeptide encoded by SEQ ID NO: 9.

SEQ ID NO: 11 is the amino acid sequence of a substilisin protease.

SEQ ID NO: 12 is the amino acid sequence of a substilisin protease.

SEQ ID NO: 13 is the amino acid sequence of a substilisin protease.

SEQ ID NO: 14 is the amino acid sequence of carboxypeptidase CPY.

SEQ ID NO: 15 is the amino acid sequence of carboxypeptidase CP1.

Polypeptides Having Carboxypeptidase Activity

In an embodiment, the present invention relates to polypeptides having a sequence identity to the mature polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have carboxypeptidase activity. In one aspect, the polypeptides differ by up to 10 amino acids, e.g., 1, 2, 3, 4, 5, 6, 7, 8, 9, or 10, from the mature polypeptide of SEQ ID NO: 2.

In a particular embodiment, the invention relates to polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the carboxypeptidase activity of the mature polypeptide of SEQ ID NO: 2.

In a particular embodiment, the invention relates to polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the carboxypeptidase activity of the mature polypeptide of SEQ ID NO: 2.

In a particular embodiment, the invention relates to polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the carboxypeptidase activity of the mature polypeptide of SEQ ID NO: 2.

In a particular embodiment, the invention relates to polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the carboxypeptidase activity of the mature polypeptide of SEQ ID NO: 2.

In a particular embodiment, the invention relates to polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the carboxypeptidase activity of the mature polypeptide of SEQ ID NO: 2.

In a particular embodiment, the invention relates to polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the carboxypeptidase activity of the mature polypeptide of SEQ ID NO: 2.

In a particular embodiment, the invention relates to polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the carboxypeptidase activity of the mature polypeptide of SEQ ID NO: 2.

In an embodiment, the present invention relates to polypeptides having a sequence identity to the mature polypeptide of SEQ ID NO: 4 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have carboxypeptidase activity. In one aspect, the polypeptides differ by up to 10 amino acids, e.g., 1, 2, 3, 4, 5, 6, 7, 8, 9, or 10, from the mature polypeptide of SEQ ID NO: 4.

In a particular embodiment, the invention relates to polypeptides having a sequence identity to the mature polypeptide of SEQ ID NO: 4 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the carboxypeptidase activity of the mature polypeptide of SEQ ID NO: 4.

In a particular embodiment, the invention relates to polypeptides having a sequence identity to the mature polypeptide of SEQ ID NO: 4 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the carboxypeptidase activity of the mature polypeptide of SEQ ID NO: 4.

In a particular embodiment, the invention relates to polypeptides having a sequence identity to the mature polypeptide of SEQ ID NO: 4 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the carboxypeptidase activity of the mature polypeptide of SEQ ID NO: 4.

In a particular embodiment, the invention relates to polypeptides having a sequence identity to the mature polypeptide of SEQ ID NO: 4 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the carboxypeptidase activity of the mature polypeptide of SEQ ID NO: 4.

In a particular embodiment, the invention relates to polypeptides having a sequence identity to the mature polypeptide of SEQ ID NO: 4 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the carboxypeptidase activity of the mature polypeptide of SEQ ID NO: 4.

In a particular embodiment, the invention relates to polypeptides having a sequence identity to the mature polypeptide of SEQ ID NO: 4 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the carboxypeptidase activity of the mature polypeptide of SEQ ID NO: 4.

In a particular embodiment, the invention relates to polypeptides having a sequence identity to the mature polypeptide of SEQ ID NO: 4 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the carboxypeptidase activity of the mature polypeptide of SEQ ID NO: 4.

In an embodiment, the present invention relates to polypeptides having a sequence identity to the mature polypeptide of SEQ ID NO: 6 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have carboxypeptidase activity. In one aspect, the polypeptides differ by up to 10 amino acids, e.g., 1, 2, 3, 4, 5, 6, 7, 8, 9, or 10, from the mature polypeptide of SEQ ID NO: 6.

In a particular embodiment, the invention relates to polypeptides having a sequence identity to the mature polypeptide of SEQ ID NO: 6 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the carboxypeptidase activity of the mature polypeptide of SEQ ID NO: 6.

In a particular embodiment, the invention relates to polypeptides having a sequence identity to the mature polypeptide of SEQ ID NO: 6 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the carboxypeptidase activity of the mature polypeptide of SEQ ID NO: 6.

In a particular embodiment, the invention relates to polypeptides having a sequence identity to the mature polypeptide of SEQ ID NO: 6 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the carboxypeptidase activity of the mature polypeptide of SEQ ID NO: 6.

In a particular embodiment, the invention relates to polypeptides having a sequence identity to the mature polypeptide of SEQ ID NO: 6 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the carboxypeptidase activity of the mature polypeptide of SEQ ID NO: 6.

In a particular embodiment, the invention relates to polypeptides having a sequence identity to the mature polypeptide of SEQ ID NO: 6 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the carboxypeptidase activity of the mature polypeptide of SEQ ID NO: 6.

In a particular embodiment, the invention relates to polypeptides having a sequence identity to the mature polypeptide of SEQ ID NO: 6 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the carboxypeptidase activity of the mature polypeptide of SEQ ID NO: 6.

In a particular embodiment, the invention relates to polypeptides having a sequence identity to the mature polypeptide of SEQ ID NO: 6 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the carboxypeptidase activity of the mature polypeptide of SEQ ID NO: 6.

In an embodiment, the present invention relates to polypeptides having a sequence identity to the mature polypeptide of SEQ ID NO: 8 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have carboxypeptidase activity. In one aspect, the polypeptides differ by up to 10 amino acids, e.g., 1, 2, 3, 4, 5, 6, 7, 8, 9, or 10, from the mature polypeptide of SEQ ID NO: 8.

In a particular embodiment, the invention relates to polypeptides having a sequence identity to the mature polypeptide of SEQ ID NO: 8 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the carboxypeptidase activity of the mature polypeptide of SEQ ID NO: 8.

In a particular embodiment, the invention relates to polypeptides having a sequence identity to the mature polypeptide of SEQ ID NO: 8 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the carboxypeptidase activity of the mature polypeptide of SEQ ID NO: 8.

In a particular embodiment, the invention relates to polypeptides having a sequence identity to the mature polypeptide of SEQ ID NO: 8 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the carboxypeptidase activity of the mature polypeptide of SEQ ID NO: 8.

In a particular embodiment, the invention relates to polypeptides having a sequence identity to the mature polypeptide of SEQ ID NO: 8 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the carboxypeptidase activity of the mature polypeptide of SEQ ID NO: 8.

In a particular embodiment, the invention relates to polypeptides having a sequence identity to the mature polypeptide of SEQ ID NO: 8 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the carboxypeptidase activity of the mature polypeptide of SEQ ID NO: 8.

In a particular embodiment, the invention relates to polypeptides having a sequence identity to the mature polypeptide of SEQ ID NO: 8 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the carboxypeptidase activity of the mature polypeptide of SEQ ID NO: 8.

In a particular embodiment, the invention relates to polypeptides having a sequence identity to the mature polypeptide of SEQ ID NO: 8 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the carboxypeptidase activity of the mature polypeptide of SEQ ID NO: 8.

In an embodiment, the present invention relates to polypeptides having a sequence identity to the mature polypeptide of SEQ ID NO: 10 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have carboxypeptidase activity. In one aspect, the polypeptides differ by up to 10 amino acids, e.g., 1, 2, 3, 4, 5, 6, 7, 8, 9, or 10, from the mature polypeptide of SEQ ID NO: 10.

In a particular embodiment, the invention relates to polypeptides having a sequence identity to the mature polypeptide of SEQ ID NO: 10 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the carboxypeptidase activity of the mature polypeptide of SEQ ID NO: 10.

In a particular embodiment, the invention relates to polypeptides having a sequence identity to the mature polypeptide of SEQ ID NO: 10 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the carboxypeptidase activity of the mature polypeptide of SEQ ID NO: 10.

In a particular embodiment, the invention relates to polypeptides having a sequence identity to the mature polypeptide of SEQ ID NO: 10 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the carboxypeptidase activity of the mature polypeptide of SEQ ID NO: 10.

In a particular embodiment, the invention relates to polypeptides having a sequence identity to the mature polypeptide of SEQ ID NO: 10 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the carboxypeptidase activity of the mature polypeptide of SEQ ID NO: 10.

In a particular embodiment, the invention relates to polypeptides having a sequence identity to the mature polypeptide of SEQ ID NO: 10 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the carboxypeptidase activity of the mature polypeptide of SEQ ID NO: 10.

In a particular embodiment, the invention relates to polypeptides having a sequence identity to the mature polypeptide of SEQ ID NO: 10 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the carboxypeptidase activity of the mature polypeptide of SEQ ID NO: 10.

In a particular embodiment, the invention relates to polypeptides having a sequence identity to the mature polypeptide of SEQ ID NO: 10 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the carboxypeptidase activity of the mature polypeptide of SEQ ID NO: 10.

In an embodiment, the polypeptide has been isolated. A polypeptide of the present invention preferably comprises or consists of the amino acid sequence of SEQ ID NO: 2, 4 or 6, 8, 10 or an allelic variant thereof; or is a fragment thereof having carboxypeptidase activity. In another aspect, the polypeptide comprises or consists of the mature polypeptide of SEQ ID NO: 2, 4, 6, 8 or 10. In another aspect, the polypeptide comprises or consists of amino acids-119-426 of SEQ ID NO: 2. In another aspect, the polypeptide comprises or consists of amino acids-111-443 of SEQ ID NO: 4. In another aspect, the polypeptide comprises or consists of amino acids 110-444 of SEQ ID NO: 6. In another aspect, the polypeptide comprises or consists of amino acids 1-477 of SEQ ID NO: 8. In another aspect, the polypeptide comprises or consists of amino acids-7-553 of SEQ ID NO: 10.

The polynucleotide of SEQ ID NO: 1, 3, 5, 7, 9 or a subsequence thereof, as well as the polypeptide of SEQ ID NO: 2, 4, 6, 8, 10 or a fragment thereof may be used to design nucleic acid probes to identify and clone DNA encoding polypeptides having carboxypeptidase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having carboxypeptidase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, 3, 5, 7, 9 or a subsequence thereof, the carrier material is used in a Southern blot.

For purposes of the present invention, hybridization indicates that the polynucleotide hybridizes to a labeled nucleic acid probe corresponding to (i) SEQ ID NO: 1, 3, 5, 7 or 9; (ii) the mature polypeptide coding sequence of SEQ ID NO: 1, 3, 5, 7 or 9; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In another embodiment, the present invention relates to a polypeptide having carboxypeptidase activity encoded by a polynucleotide having a sequence identity to the mature polypeptide coding sequence of SEQ ID NO: 1, 3, 5, 7 or 9 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to variants of the mature polypeptide of SEQ ID NO: 2, 4, 6, 8 or 10 comprising a substitution, deletion, and/or insertion at one or more (e.g., several) positions. In an embodiment, the number of amino acid substitutions, deletions and/or insertions introduced into the mature polypeptide of SEQ ID NO: 2, 4, 6, 8 or 10 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant molecules are tested for carboxypeptidase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Carboxypeptidase Activity

A polypeptide having carboxypeptidase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In one embodiment, the polypeptide is a *Penicillium* polypeptide, e.g., a polypeptide obtained from *Penicillium emersonii*.

In one embodiment, the polypeptide is a *Myceliophthora* polypeptide, e.g., a polypeptide obtained from *Myceliophthora heterothallica*.

In one embodiment, the polypeptide is a *Chaetomium* polypeptide, e.g., a polypeptide obtained from *Chaetomium strumarium*.

In one embodiment, the polypeptide is a *Lasiodiplodia* polypeptide, e.g., a polypeptide obtained from *Lasiodiplodia theobromae*.

In one embodiment, the polypeptide is a *Thermoascus* polypeptide, e.g., a polypeptide obtained from *Thermoascus aurantiacus*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Nucleic Add Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dana (WO 00/56900), *Fusarium venenatum* Quinn (WO 00/56900), *Rhizomucor miehei* lipase, *Rhizomucor miehei* aspatic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extra-chromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus altitudinis, Bacillus amyloliquefaciens, B. amyloliquefaciens* subsp. *plantarum, Bacillus brevis, Bacillus circulans, Bacillus clausii, Bacillus coagulans, Bacillus firmus, Bacillus lautus, Bacillus lentos, Bacillus licheniformis, Bacillus megaterium, Bacillus methylotrophicus, Bacillus pumilus, Bacillus safensis, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp, *Zooepidemicus* cells, The bacterial host cell may also be any *Streptomyces* cell including, but not limited to, *Streptomyces achromogenes, Streptomyces avermitifis, Streptomyces coelicolor Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ, Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbial.* 65: 3800-3804), or conjugation (see, e.g., Clewell, 1981, *Microbial, Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oornycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (*Endomycetales*), basidiosporogenous yeast, and yeast belonging to the *Fungi Imperfecti* (*Blastomycetes*). Since the classification of yeast may change in the future, for the purposes of this invention, yeast shall be defined as described in *Biology and Activities of Yeast* (Skinner, Passmore, and Davenport, editors, *Soc. App. Bacteria. Symposium Series* No. 9, 1980).

The yeast host cell may be a *Candida, Hansenula, Kluyveramyces, Pichia, Saccharomyces, Schizosaccharomyces,* or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandere, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergilius awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chtysosporium keratinophilum, Chtysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophile, Neurospora crassa, Penicillium purpurogenum, Phanerochaete chrysosporium, Phlebia radiate, Pleurotus eryngii, Thielavia terrestris, Trametes villose, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito of al., 1983, *J. Bacterial.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide. In one aspect, the cell is a *Aspergillus* cell. In another aspect, the cell is a *Aspergillus oryzae* cell.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides having carboxypeptidase activity. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, UCH Publishers, New York, 1989) to obtain substantially pure polypeptides.

The invention is further summarized in the following paragraphs:

1. A method for producing a protein hydrolysate comprising:
    a. providing an aqueous solution or suspension of a protein substrate; and
    b. exposing the aqueous solution or suspension of the protein substrate to a polypeptide having endopeptidase activity and to a polypeptide having carboxypeptidase activity, to obtain the protein hydrolysate; wherein the polypeptide having carboxypeptiddase activity is characterised by having a Pro/ACHA*100 ratio of at least 30.
2. Method according to paragraph 1, wherein the Pro/ACHA*100 ratio is at least 35, at least at least 40, such as at least 41, at least 42, at least 45, at least 50, at least 51, at least 50, at least 52, at least 53, at least 54, at least 55, at least 56, at least 57, at least 58, at least 59, at least 60 or at least 61.
3 Method according to any of paragraphs 1-2, wherein the protein substrate is a vegetable protein or an animal protein.
4. Method according to paragraph 3, wherein the vegetable protein substrate is selected from the group consisting of cereal, legumes and oilseed.
5. Method according to paragraph 4, wherein the vegetable protein substrate from cereal is selected from the group comprising wheat, barley, oat, rye, triticale, maize, rice, sorghum, buckwheat, quinoa, chia, millet or fonio.
6. Method according to paragraph 5, wherein the protein substrate is gluten, preferably wheat gluten.
7. Method according to paragraph 4, wherein the vegetable protein substrate from legumes is selected from the group consisting of peas, beans, lentils and chick peas.
8. Method according to paragraph 4, wherein the vegetable protein substrate from oilseed is selected from soy bean, cotton seed, peanut, rape seed, sunflower seed, palm kernel, coconut, corn, safflower seed, sunflower seed and lin seed.
9. Method according to paragraph 8, wherein the protein substrate is soy protein.
10. Method according to paragraph 3, wherein the animal protein is selected from milk proteins such as casein or whey proteins.
11. Method according to any of the preceding paragraphs, wherein the concentration of the protein substrate in the aqueous solution or suspension is in the range of 5-35%.
12. Method according to paragraph 11, wherein the concentration of the protein substrate is in the range of 5-30%, in the range of 5-25%, in the range of 5-20%, in the range of 5-15% or in the range of 10-15%.
13. Method according to any of the preceding paragraphs, wherein the polypeptide having carboxypeptidase activity has an activity of at least 0.15 on Proline when measured in Assay 1, such as at least at least 0.16, at least 0.17, at least 0.18, at least 0.19, at least 0.2, at least 0.21, at least 0.22, at least 0.23, at least 0.24, at least 0.25, at least 0.3, at least 0.35, at least 0.4, at least 0.45, at least 0.5, at least 0.55, at least 0.6 or at least 0.625.
14. Method according to any of the preceding paragraphs, wherein the polypeptide having carboxypeptiddase activity has an average hydrophobic activity of at least 0.51 when measured in Assay II.
15. Method according to any of the preceding paragraphs wherein the polypeptide having carboxypeptidase activity has an ACHA value of at least 0.52, such as at least 0.53, at least 0.54, at least 0.56, at least 0.57, at least 0.58 or at least 0.59.
16. Method according to any of paragraphs 1-12, wherein the polypeptide having carboxypeptidase activity has an ACLA value in the range of 0.15-0.25.
17. Method according to paragraph 16, wherein the polypeptide having carboxypeptidase activity has an ACLA value in the range of 0.16-0.25, such as in the range of 0.17-0.25, in the range of 0.18-0.25, in the range of 0.19-0.25.
18. Method according to any of the preceding paragraphs wherein the concentration of the polypeptide having endopeptidase activity is in the range of 0.1-3.0% w/w on protein.
19. Method according to paragraph 18, wherein the concentration is in the range of 0.1-2.8%, such as in the range of 0.1-2.6%, in the range of 0.1-2.4%, in the range of 0.1-2.2%, in the range of 0.1-2.0%, in the range of 0.1-1.8%, in the range of 0.1-1.6%, in the range of 0.1-1.4%, in the range of 0.1-1.2%, in the range of 0.1-1.0%, in the range of 0.2-1.0%, in the range of 0.3-1.0%, in the range of 0.4-1.0% or in the range of 0.5-1.0%.
20. Method according to any of the preceding paragraphs wherein the concentration of the polypeptide having carboxypeptidase activity is in the range of 0.01-4 mg enzyme protein/gram protein substrate.
21. Method according to paragraph 20, wherein the concentration is in the range of 0.01-3.9 mg enzyme protein/gram protein substrate, such as in the range of 0.1-3.8 mg enzyme protein/gram protein substrate, in the range of 0.1-3.6, in the range of 0.2-3.4, in the range of 0.2-3.2, in the range of 0.3-3.0, in the range of 0.3-2.8, in the range of 0.4-2.6, in the range of 0.4-2.4, in the range of 0.5-2.2, in the range of 0.5-2.0.
22. The method of any of the preceding paragraphs wherein the protein substrate is exposed to the polypeptide having endopeptidase activity and the polypeptide having carboxypeptidase activity for at least 3 hours.
23. Method according to paragraph 22, wherein the protein substrate is exposed to the polypeptide having endopeptidase activity and the polypeptide having carboxypeptidase activity for 3-48 hours, such as 4-48

23. (continued) hours, such as 4-36 hours, 6-32 hours, 8-28 hours, 10-26 hours, 12-24 hours, 12-22 hours, 12-20 hours, 12-18 hours, 12-16 hours or for 12-14 hours.

24. Method according to any of the preceding paragraphs, wherein method is carried out at a temperature above 10° C.

25. Method according to paragraph 24, wherein the temperature is in the range of 10-90° C., such as in the range of 20-80° C., in the range of 30-70° C., in the range of 40-60° C., in the range of 45-55° C. or in the range of 50-60° C.

26. Method according to any of the preceding paragraphs, wherein the pH of the aqueous solution or the aqueous suspension is in the range of 5-8, such as in the range of 5.5-6.5 or in the range of 6.0-7.0.

27. Method according to any of the preceding paragraphs wherein the protein substrate is exposed to polypeptide having endopeptidase activity and the polypeptide having carboxypeptidase activity at the same time.

28. Method according to any of the preceding paragraphs, wherein the protein substrate is exposed to the polypeptide having endopeptidase activity before being exposed to the polypeptide having carboxypeptidase activity.

29. Method according to any of the preceding paragraphs, wherein the protein substrate is further exposed to a polypeptide having aminopeptidase activity such as aminopeptidase 2.

30. Method according to paragraph 29, wherein the aminopeptidase is the polypeptide of SECS ID NO: 16.

31. Method according to paragraph 29, wherein the protein substrate is exposed to the polypeptide having aminopeptidase activity at the same time as being exposed to the polypeptide having endopeptidase activity.

32. Method according to paragraph 29, wherein the protein substrate is exposed to the polypeptide having aminopeptidase activity before, simultaneously or after the protein substrate is exposed to the polypeptide having carboxypeptidase activity.

33. Method according to paragraph 29, wherein the concentration of the polypeptide having aminopeptidase activity is in the range of 0.05-4 mg enzyme protein per gram protein substrate, such as 0.05-3.5 mg enzyme protein per gram protein substrate, 0.05-3.0 mg enzyme protein per gram protein substrate, 0.05-2.5 mg enzyme protein per gram protein substrate, 0.05-2.0 mg enzyme protein per gram protein substrate, 0.06-2.0 mg enzyme protein per gram protein substrate, 0.07-2.0 mg enzyme protein per gram protein substrate, 0.08-2.0 mg enzyme protein per gram protein substrate, 0.09-2.0 mg enzyme protein per gram protein substrate or 0.1-2.0 mg enzyme protein per gram protein substrate.

34. Method according to any of the preceding paragraphs, wherein the method is carried out until the obtained protein hydrolysate has a degree of hydrolysis (% DH) in the range of 30%-70%, such as in the range of 45%-70%, in the range of 50%-70%, in the range of 55%-70%, in the range of 60%-70%, in the range of 65%-70%.

35. Method according to any of the preceding paragraphs, wherein the polypeptide having endopeptidase activity is a subtilisin.

36. Method according to paragraph 35, wherein the subtilisin is selected from SEQ ID NO: 11, SEQ ID NO: 12, SEQ ID NO: 13.

37. Method according to any of the preceding paragraphs, wherein the polypeptide having carboxypeptidase activity is obtained from fungal source.

38. Method according to paragraph 37, wherein the polypeptide having carboxypeptidase activity is defined in paragraphs 39-45.

39. An isolated polypeptide having carboxypeptidase activity, selected from the group consisting of:
    a. a polypeptide having at least 60% sequence identity to the mature polypeptide of SEQ ID NO: 2, SEQ ID NO: 4 or SEQ ID NO: 6, SEQ ID NO: 8, SEQ ID NO: 10;
    b. a polypeptide encoded by a polynucleotide having at least 60% sequence identity to the mature polypeptide coding sequence of SEQ ID NO: 1, SEQ ID NO: 3 or SEQ ID NO: 5, SEQ ID NO: 7, SEQ ID NO: 9 or the cDNA sequence thereof;
    c. a variant of the mature polypeptide of SEQ ID NO: 2, SEQ ID NO: 4, SEQ ID NO: 6, SEQ ID NO: 8 or SEQ ID NO: 10 comprising a substitution, deletion, and/or insertion at one or more positions; and
    d. a fragment of the polypeptide of (a), (b) or (c) that has carboxypeptidase activity.

40. Polypeptide according to paragraph 39, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2, SEQ ID NO: 4, SEQ ID NO: 6, SEQ ID NO: 8 or SEQ ID NO: 10.

41. Polypeptide according to any of paragraphs 39-40, which is encoded by a polynucleotide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1 SEQ ID NO: 3, SEQ ID NO: 5, SEQ ID NO: 7 or SEQ ID NO: 9 or the cDNA sequence thereof.

42. Polypeptide according to any of paragraphs 39-41, comprising or consisting of SEQ ID NO: 2, SEQ ID NO: 4, SEQ ID NO: 6, SEQ ID NO: 8 or SEQ ID NO: 10; or the mature polypeptide of SEQ ID NO: 2, SEQ ID NO: 4, SEQ ID NO: 6, SEQ ID NO: 8 or SEQ ID NO: 10.

43. Polypeptide according to paragraph 42, wherein the mature polypeptide is amino acids 1-426 of SEQ ID NO: 2, amino acids 1-443 of SEQ ID NO: 4, amino acids 1-444 of SEQ ID NO: 6, amino acids 1-477 SEQ ID NO: 8 or amino acids 1-553 of SEQ ID NO: 10.

44. Polypeptide according to any of paragraphs 39-43, which is a variant of the mature polypeptide of SEQ ID NO: 2, SEQ ID NO: 4, SEQ ID NO: 6, SEQ ID NO: 8 or SEQ ID NO: 10 comprising a substitution, deletion, and/or insertion at one or more positions.

45. Polypeptide according to paragraph 39, which is a fragment of SEQ ID NO: 2, SEQ ID NO: 4, SEQ ID NO: 6, SEQ ID NO: 8 or SEQ ID NO: 10, wherein the fragment has carboxypeptidase activity.

46. A liquid or granulate composition comprising the polypeptide of any of paragraphs 39-45.

47. A whole broth formulation or cell culture composition comprising the polypeptide of any of paragraphs 39-45.

48. An polynucleotide encoding the polypeptide of any of paragraphs 39-45.

49. A nucleic acid construct or expression vector comprising the polynucleotide of paragraph 48 operably linked to one or more control sequences that direct the production of the polypeptide in an expression host.
50. A recombinant host cell comprising the polynucleotide of paragraph 49 operably linked to one or more control sequences that direct the production of the polypeptide.
51. A method of producing the polypeptide of any of paragraphs 39-45, comprising cultivating a cell, which in its wild-type form produces the polypeptide, under conditions conducive for production of the polypeptide.
52. Method according to paragraph 51, further comprising recovering the polypeptide.
53. A method for producing a polypeptide having carboxypeptidase activity, comprising cultivating the host cell of paragraph 50 under conditions conducive for production of the polypeptide.
54. Method according to paragraph 53, further comprising recovering the polypeptide.
55. Use of an polypeptide having endopeptidase activity and a polypeptide having carboxypeptidase activity for hydrolysing a protein substrate to obtain a protein hydrolysate, wherein the polypeptide having carboxypeptiddase activity is characterised by having a Pro/ACHA*100 ratio of at least 30.
56. Use according to paragraph 60, wherein the endopeptidase and a polypeptide having carboxypeptidase activity is used in a method according to any of paragraphs 1-38.
57. Protein hydrolysate produced by the method according to any of paragraphs 1-38.
58. Protein hydrolysate comprising free amino acids, wherein the amount of free amino acids is at least 20 g per 100 gram protein, the total amount of Ala, Val, Ile, Leu, Met, Phe and Trp is at least 7 g per 100 g protein and at least 1.0 g Pro per 100 g protein.
59. Protein hydrolysate according to paragraph 58, wherein the amount of free amino acids is at least 25 g per 100 g protein hydrolysate, such as at least 30 g per 100 g hydrolysate, at least 30 g per 100 g hydrolysate, at least 35 g per 100 g hydrolysate or at least 40 g per 100 g hydrolysate.
60. Protein hydrolysate according to any of paragraphs 58-59, wherein the amount of Ala, Val, Ile, Leu, Met, Phe and Trp is at least 13 g per 100 g protein substrate and at least 1.8 g per 100 g protein hydrolysate.
61. Protein hydrolysate according to any of paragraphs 58-60, wherein the hydrolysate further has a degree of hydrolysation (% dH) in the range of 30%-70%, such as in the range of 45%-70%, in the range of 50%-70%, in the range of 55%-70%, in the range of 60%-70%, in the range of 65%-70%.

Assays

Assay I

Carboxypeptidase Activity for Proline (Z-Ala-Pro-OH Substrate)

Reagents and Chemicals

Assay buffer: 100 mM succinic acid (Sigma), 50 mM KCl (Sigma), 1 mM CaCl2) (Sigma), 0.01% Triton X-100 (Sigma), pH adjusted to 6.0

Substrate: Z-L-alanyl-L-Pro-OH substrate (Z-Ala-Pro-OH, Bachem, C-1185) was dissolved in DMSO to a concentration of 40 mM.

Procedure

25 µL of assay buffer, 25 µL deionized water, 5 µL of the 7-Ala-Pro-OH substrate and 10 µL of enzyme diluted to a concentration of 5 µg/mL were added to the wells of a 96 well microtiter plate (MTP). The MTP was incubated at 55° C. for 30 minutes with shaking at 1000 rpm in an Eppendorf Thermomixer comfort. Then the MTP was transferred to a fridge kept at 4° C. for 10 minutes. 100 µL of 2.0 M HEPES pH 10.0 and then 100 µL of a 6% solution of ninhydrin (Sigma) dissolved in 100% ethanol were added to the wells containing the enzyme and substrate solution. The MTP was incubated at 80° C. for 5 minutes with moderate shaking (350 rpm). The MTP was then kept at room temperature for 10 minutes and the absorbance of the sample at 450 nm was then measured.

The activity of the enzyme towards (or on) the Z-Ala-Pro-OH substrate was calculated as the absorption at 450 nm minus the background absorption of a blank (blank sample with 10 µL assay buffer added instead of enzyme solution). Results was rounded off to the second decimal digit.

Assay II

Carboxypeptidase Assay

Reagents and Chemicals

Assay buffer: 100 mM succinic acid (Sigma), 50 mM KCl (Sigma), 1 mM CaCl2 (Sigma), 0.01% Triton X-100 (Sigma), pH adjusted to 6.0

Stop reagent: 17.9 g trichloro acetic acid (Sigma), 29.9 g sodium acetate trihydrate (Sigma) and 19.0 mL concentrated acetic acid (Sigma) were mixed and deionized water was added to a final volume of 500 mL OPA reagent: 47.6 g disodium tetraborate decahydrate (Sigma) and 12.5 g sodium dodecyl sulfate (Sigma) were dissolved in 1 L deionized water Substrate working solution: The Z-L-alanyl-L-XXX-OH substrate listed in table 1 were dissolved in DMSO or deionized water to a concentration of 40 mM (Z-Ala-XXX-OH, where XXX is one of the 17 amino acid listed below).

TABLE 1

| Code | Name | Supplier | Code | Solvent |
| --- | --- | --- | --- | --- |
| G | Z-Ala-Gly-OH | Bachem | C-1080 | DMSO |
| A | Z-Ala-Ala-OH | Bachem | C-1045 | DMSO |
| S | Z-Ala-Ser-OH | Bachem | C-1215 | DMSO |
| V | Z-Ala-Val-OH | Bachem | C-1245 | DMSO |
| L | Z-Ala-Leu-OH | Bachem | C-3155 | DMSO |
| I | Z-Ala-Ile-OH | Bachem | C-1130 | DMSO |
| M | Z-Ala-Met-OH | Bachem | C-1145 | DMSO |
| F | Z-Ala-Phe-OH | Bachem | C-1155 | DMSO |
| Y | Z-Ala-Tyr-OH | Bachem | C-1235 | DMSO |
| W | Z-Ala-Trp-OH | Bachem | C-1225 | DMSO |
| D | Z-Ala-Asp-OH | Bachem | C-1070 | DMSO |
| E | Z-Ala-Glu-OH | Bachem | C-1075 | DMSO |
| N | Z-Ala-Asn-OH | Bachem | C-1065 | DMSO |
| H | Z-Ala-His-OH | Bachem | C-1120 | DMSO |
| K | Z-Ala-Lys-OH | Bachem | C-1140 | dH2O |
| R | Z-Ala-Arg-OH | Bachem | C-1060 | DMSO |
| Q | Z-Ala-Gln-OH | Santa Cruz Biotechnology | sc-475969 | dH2O |

Procedure

Carboxypeptidase activity can be determined using the substrates listed in Table 1 as follows. 50 µL of assay buffer, 10 µL of enzyme diluted to a concentration of 5 µg/mL, 5 µL of the Z-Ala-XXX-OH substrate were added to the wells of a 96 well microtiter plate (MTP). The MTP was incubated at 55° C. for 30 minutes with shaking at 1000 rpm in an Eppendorf Thermomixer comfort. Then the MTP was transferred to a fridge kept at 4° C. for 10 minutes. 100 µL of stop reagent was added to the wells containing the enzyme and substrate solution and the MTP was shaken for 10 seconds at 1000 rpm to ensure complete mixing of the two solutions.

80 mg ortho-phtaldialdehyde (OPA, Sigma) were dissolved in 2 mL ethanol (Sigma) and 88 mg DL-Dithiothreitol (Sigma) were dissolved in 2 mL deionized water. The two solutions were added to 80 mL of OPA reagent and the solutions were stirred at room temperature. After 5 minutes mixing the solution volume was adjusted to 100 mL with deionized water (OPA solution). 225 µL of the freshly-prepared OPA solution was added to the wells of a new MTP. 30 µL supernatant from the MTP containing enzymes and substrate was added to the well of the second MTP. The solution was mixed for 10 seconds at room temperature and absorbance of the sample at 340 nm was measured after 2 minutes of addition of the OPA solution.

The activity of the enzyme for a substrate was calculated as the absorption at 340 nm minus the background absorption of a blank (blank sample with 10 µL assay buffer added instead of enzyme solution). Results were rounded off to the second decimal digit.

Assay III
Testing for endopeptidase activity
Reagent and chemicals
Substrate: Protazyme OL (Megazyme T-PROL 1000).
Temperature: 30° C.
Assay buffer: 100 mM HEPES (Sigma), 50 mM KCl (Sigma), 1 mM CaCl2 (Sigma), 0.01% Triton X-100 (Sigma), pH adjusted to 6.0
Procedure A Protazyme OL tablet (from Megazyme) was suspended in 2.0 ml 0.01% Triton X-100 by gentle stirring. 500 µL of this suspension and 500 µL assay buffer were mixed in an Eppendorf tube and placed on ice. 20 µL Alcalase sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate (1400 rpm.). The reaction was stopped by transferring the tube back to the ice bath. Then the tube was centrifuged in an ice cold centrifuge for a few minutes and 200 µL supernatant was transferred to a microtiter plate. The absorbance at 650 nm (OD650) was read as a measure of protease activity. A blank sample (20 µL 0.01% Triton X-100 instead of enzyme) was prepared and was included in the assay. The enzymatic activity was calculated as OD 650(sample)-OD650(blank).

Assay IV
Testing for aminopeptidase activity
Reagents and Chemicals
Assay buffer: 100 mM succinic acid (Sigma), 50 mM KCl (Sigma), 1 mM CaCl2) (Sigma), 0.01% Triton X-100 (Sigma), pH adjusted to 6.0
Substrate listed in table 1B were dissolved in DMSO to a concentration of 40 mM (H-XXX-pNA, where XXX is one of the 18 amino acid listed below).
Procedure 100 µL of assay buffer, 5 µL of the H-XXX-pNA substrate and 10 µL of enzyme diluted to a concentration of 5 µg/mL were added to the wells of a 96 well microtiter plate (MTP). The MTP was incubated at 55° C. for 60 minutes with shaking at 1000 rpm in an Eppendorf Thermomixer comfort. Then the absorbance of the sample at 405 nm was measured.

The activity of the enzyme towards (or on) the H-XXX-pNA substrate was calculated as the absorption at 405 nm minus the background absorption of a blank (blank sample with 10 µL assay buffer added instead of enzyme solution). Results was rounded off to the second decimal digit.

TABLE 1B

| Code | Name | Supplier | Code | Solvent |
| --- | --- | --- | --- | --- |
| G | H-Gly-pNA | Bachem | L-1280 | DMSO |
| A | H-Ala-pNA | Bachem | L-1070 | DMSO |
| S | H-Ser-pNA | TAG Copenhagen | N.A. | DMSO |
| C | H-Cys-pNA | TAG Copenhagen | N.A. | DMSO |
| V | H-Val-pNA | Bachem | L-1440 | DMSO |
| L | H-Leu-pNA | Bachem | I-1305 | DMSO |
| I | H-Ile-pNA | Bachem | L-1815 | DMSO |
| M | H-Met-pNA | Bachem | L-1320 | DMSO |
| P | H-Pro-pNA | Bachem | L-1370 | DMSO |
| F | H-Phe-pNA | Bachem | L-1355 | DMSO |
| Y | H-Tyr-pNA | TAG Copenhagen | N.A. | DMSO |
| W | H-Trp-pNA | TAG Copenhagen | N.A. | DMSO |
| D | H-Asp-pNA | Bachem | L-1525 | DMSO |
| E | H-Glu-pNA | Bachem | L-1540 | DMSO |
| N | H-Asn-pNA | TAG Copenhagen | N.A. | DMSO |
| H | H-His-pNA | Bachem | L-1785 | DMSO |
| K | H-Lys-pNA · 2 HBr | Bachem | L-1315 | DMSO |
| R | H-Arg-pNA · 2 HCl | Bachem | L-1120 | DMSO |

N.A.=not available
Assay V
OPA Assay:

20 µl of a diluted sample with a protein concentration of 0.06-0.1% was added to a microtiterplate followed by 200 µl OPA solution. The plate was shaken and absorbance read immediately at 340 nm. OPA solution was in 100 ml MQ water: 0.504 g sodium bicarbonate, 0.429 g sodium carbonate decahydrate, 88 mg dithiothreitol, 1 ml 10% SDS, 80 mg ophthaldialdehyde (OPA) in 2 ml 96% ethanol. A standard curve using 125 mg L-serine in 250 ml MQ water and diluted 2, 4, 8, 16, 32, 64 fold was included, and the response of the samples calculated by comparing to this.

Calculations:

$$DH(\%) = \frac{Ser\text{-equivalents in sample (mg }Ser/\text{ml)} * \text{Dilution factor (ml/g)} * 100\%}{\text{Protein content in samples (g/100 g)} * 1000(\text{mg/g})}$$

HPLC Analysis:

Amino acid content was analysed using a ThermoFischer WPS3000 high pressure liquid chromatography system comprising a quaternary pump, an autosampler, a column oven, and a tuneable fluorescence detector. Prior to the analysis, samples were filtered using 0.22 µm PVDF filters and norvaline added as an internal standard. Samples were analysed after automated pre-column derivatization. 28 µL milli-Q water, 10 µL of 0.4 M borate buffer pH 10.2, 2 µL sample, 2 µL ortho-phthaldialdehyde 2.5 g/L in 0.1 M borate buffer pH 10.2 and 2 µL fluorenylmethyl chloroformate 0.6 g/L in acetonitrile were collected and mixed by pipetting up and down in a mixing vial. 100 µL milli-Q water was added followed by mixing, and 10 µL was finally injected for chromatographic analysis on a Kinetex 5 µm EVO C18 100 Å LC column (150 mm×4.6 mm) with a corresponding SecurityGuard ULTRA cartridge guard column. Solvents were: A: 20 mM potassium phosphate buffer pH 7.2 and B: 50% methanol, 50% acetonitrile. The pump was set to a constant flow rate of 1 ml/minute, and a linear gradient implemented from 0 to 26 min using 3% solvent B up to 60% solvent B. After 26 min, the solvent composition was changed to 3% solvent B and the column equilibrated until 35 min. Column temperature was 40° C. Primary amino acids were excited at 340 nm and emission wavelength was 460 nm while for the secondary amino acids the excitation wavelength was 288 nm and the emission wavelength 308 nm. Samples were analysed by comparison to an amino acids standard mix in a concentration range up to 0.3125 mM. All 20 amino acids were analysed except cysteine. Histidine and glycine coeluted.

EXAMPLES

Materials and Methods
Overview of Sequences Listing
SEQ ID NO: 1 is the sequence of a polynucleotide derived from *Penicillium emersonii*.
SEQ ID NO: 2 is the amino acid sequence of the polypeptide encoded by SEQ ID NO: 1.
SEQ ID NO: 3 is the sequence of a polynucleotide derived from *Myceliophthora heterothallica*.
SEQ ID NO: 4 is the amino acid sequence of the polypeptide encoded by SEQ ID NO: 3.
SEQ ID NO: 5 is the sequence of a polynucleotide derived from *Chaetomium strumarium*.
SEQ ID NO: 6 is the amino acid sequence of the polypeptide encoded by SEQ ID NO: 5.
SEQ ID NO: 7 is the sequence of a polynucleotide derived from *Lasiodiplodia theobromae*.
SEQ ID NO: 8 is the amino acid sequence of the polypeptide encoded by SEQ ID NO: 7.
SEQ ID NO: 9 is the sequence of a polynucleotide derived from *Thermoascus aurantiacus*.
SEQ ID NO: 10 is the amino acid sequence of the polypeptide encoded by SEQ ID NO: 9.
SEQ ID NO: 11 is the amino acid sequence of a substilisin protease.
SEQ ID NO: 12 is the amino acid sequence of a substilisin protease.
SEQ ID NO: 13 is the amino acid sequence of a substilisin protease.
SEQ ID NO: 14 is the amino acid sequence of Carboxypeptidase CPY
SEQ ID NO: 15 is the amino acid sequence of Carboxypeptidase CP1
SEQ ID NO: 16 is the amino acid sequence of an amino peptidase.

Example 1

Strain
A fungal strain was isolated from a compost sample collected from Yunnan province, China by the dilution plate method with FDA medium at 45° C. It was then purified by transferring a single conidium onto a YG agar plate. The strain was identified as *Penicillium emersonii*, based on both morphological characteristics and ITS rDNA sequence.
Media
PDA medium was composed of 39 grams of potato dextrose agar and deionized water to 1 liter.
YG agar plates were composed of 5.0 g of yeast extract, 10.0 g of glucose, 20.0 g of agar, and deionized water to 1 liter.
YPG medium contained 0.4% of yeast extract, 0.1% of $KH_2PO_4$, 0.05% of $MgSO_4.7H_2O$, 1.5% glucose in deionized water.
YPM medium contained 1% yeast extract, 2% of peptone, and 2% of maltose in deionized water.
Genomic DNA Extraction of *Penicillium emersonii*
*Penicillium emersonii* strain was inoculated onto a PDA plate and incubated for 3 days at 45° C. in the darkness. Several mycelia-PDA plugs were inoculated into 500 ml shake flasks containing 100 nil of YPG medium. The flasks were incubated for 3 days at 45° C. with shaking at 160 rpm. The mycelia were collected by filtration through MIRACLOTH® (Calbiochem, La Jolla, Calif., USA) and frozen in liquid nitrogen. Frozen mycelia were ground, by mortar and pestle, to a fine powder, and genomic DNA was isolated using an Andybio Large-Scale Column Fungal DNAout Kit (Bioserver Inc., BeiJing, China).

Genome Sequencing, Assembly and Annotation
The extracted genomic DNA samples were delivered to Beijing Genome Institute (BGI, Shenzhen, China) for genome sequencing using an ILLUMINA® GA2 System (Illumina, Inc., San Diego, Calif., USA). The raw reads were assembled at BGI using program SOAPdenovo (Li et al., 2010, *Genome Research* 20(2): 265-72). The assembled sequences were analyzed using standard bioinformatics methods for gene finding and functional prediction. GeneID (Parra et al., 2000, *Genome Research* 10(4): 511-515) was used for gene prediction. Blastall version 2.2.10 (Altschul et al., 1990, J. Mol. Biol. 215 (3): 403-410, National Center for Biotechnology Information (NCBI), Bethesda, Md., USA) and HMMER version 2.1.1 (National Center for Biotechnology Information (NCBI), Bethesda, Md., USA) were used to predict function based on structural homology. The carboxypeptidase gene, S10_Pe1, was identified directly by analysis of the Blast results. The Agene program (Munch and Krogh, 2006, *BMC Bioinformatics* 7: 263) and SignalP program (Nielsen et al., 1997, *Protein Engineering* 10: 1-6) were used to identify start codons. The SignalP program was further used to predict signal peptides. Pepstats (Rice et al., 2000, *Trends Genet.* 16(6): 276-277) was used to predict the isoelectric points and molecular weights of the deduced amino acid sequences.

Cloning of the Carboxypeptidase Gene of *Penicillium emersonii* from Genomic DNA
The expression vector pCaHj505 was used for gene cloning. It contained the TAKA-amylase promoter derived from *Aspergillus oryzae* and the *Aspergillus niger* glucoamylase terminator elements. Furthermore pCaHj505 had pUC18 derived sequences for selection and propagation in *E. coli*, and an amdS gene, which encoded an acetoamidase gene derived from *Aspergillus nidulans* for selection of an amdS+ *Aspergillus* transformant.
The carboxypeptidase gene, S10_Pe1, SEQ ID NO: 1 for the genomic DNA sequence and SEQ ID NO: 2 for the deduced amino acid sequence, was selected for expression cloning.
Based on the DNA information obtained from genome sequencing, oligonucleotide primers, shown below, were designed to amplify the coding sequence of the carboxypeptdase genes from the genomic DNA of *Penicillium emersonii* NN051602. The primers were synthesized by Invitrogen, Beijing, China.

```
Primer1:
                                          [SEQ ID NO: 17]
5' ACACAACTGGGGATC CACC atgagagttcttcctgcgac 3'

Primer2:
                                          [SEQ ID NO: 18]
5' CCCTCTAGATCTCGAG gaacgcgacacgcttctca 3'
```

Lowercase characters of the forward primer represent the coding region of the gene and lowercase characters of the reverse primer represent the flanking region of the gene, while captalized characters represent a region homologous to insertion sites of pCaHj505 (WO2013029496). The 4 underlined characters ahead of the coding sequence in the forward primer represent the Kozak sequence as the initiation of translation process.

Ten picomoles of the forward and reverse primers above, primer1 and primer2, were used in a PCR reaction for amplification of the *Penicillium emersonii* carboxypeptidase gene S10_Pe1. The PCR reaction was composed of 2 μl of genomic DNA of *Penicillium emersonii* NN051602, 10 μl of 5× Phusion® HF Buffer (Finnzymes Oy, Espoo, Finland), 1.5 μl of DMSO, 1.5 ul of 2.5 mM each of dATP, dTTP, dGTP, and dCTP, and 0.6 unit of PHUSION® High-Fidelity DNA Polymerase (Finnzymes Oy, Espoo, Finland) in a final volume of 50 μl. The amplification was performed using a Peltier Thermal Cycler (MJ Research Inc., South San Francisco, Calif., USA) programmed for denaturing at 98° C. for 1 minute; 7 cycles of denaturing each at 98° C. for 30 seconds, annealing at 65° C. for 30 seconds with 1° C. decrease per cycle, and elongation at 72° C. for 2 minutes; 25 cycles each at 94° C. for 30 seconds, 60° C. for 30 seconds, and 72° C. for 2 minutes; and a final extension at 72° C. for 5 minutes. The heat block then went to a 4° C. soak cycle.

The PCR product was isolated by 1.0% agarose gel electrophoresis using 90 mM Trisborate and 1 mM EDTA (TBE) buffer where a single product band of approximately 1.8 kb from the reaction was visualized under UV light. The PCR product was then purified from solution by using an Illustra™ GFX™ PCR DNA and Gel Band Purification Kit (GE Healthcare, Buckinghamshire, UK) according to the manufacturers instructions.

Plasmid pCaHj505 was digested with Bam HI and Xho I, isolated by 1.0% agarose gel electrophoresis using TBE buffer, and purified using an ILLUSTRA™ GFX™ PCR DNA and Gel Band Purification Kit according to the manufacturer's instructions.

In-Fusion® HD Cloning Kit (Clontech Laboratories, Inc., Mountain View, Calif., USA) was used to clone the PCR fragment directly into the expression vector pCaHj505, without the need for restriction digestion.

The purified PCR fragment and the digested vector were ligated together using the In-Fusion® HD Cloning Kit according to the manufacturer's instructions resulting in plasmid p505-S10_Pe1 (Figure 1), in which the transcription of the carboxypeptidase polypeptide coding sequence was under the control of an *Aspergillus oryzae* alpha-amylase gene promoter. In brief, 0.8 ul of 30 ng/ul of pCaHj505, digested with Bam HI and Xho I, and 3.2 ul of the purified PCR fragment containing ~60 ng of the *Penicillium emersonii* carboxypeptidase gene PCR fragment were added to 1 ul of 5× In-Fusion® HD Enzyme Premix. The reaction was incubated at 50° C. for 15 minutes. The ligation reaction was used to transform *E. coli* TOP10 competent cells (TIANGEN Biotech Co. Ltd., Beijing, China). *E. coli* transformants containing an expression construct were detected by colony PCR. Colony PCR is a method for quick screening of plasmid inserts directly from *E. coli* colonies. Briefly, a single colony was transferred to a premixed PCR solution in a PCR tube, including PCR buffer, $MgCl_2$, dNTPs, Taq DNA polymerase and primer pairs from which the PCR fragment was generated. Several colonies were screened. After the PCR, reactions were analyzed by 1.0% agarose gel electrophoresis using TBE buffer. Plasmid DNA was prepared using a QIAPREP® Spin Miniprep Kit (QIAGEN GmbH, Hilden, Germany) from the colony showing an insert with the expected size. The carboxypeptidase gene coding sequence inserted in p505-S10_Pe1 was confirmed by DNA sequencing using 3730XL DNA Analyzers (Applied Biosystems Inc, Foster City, Calif., USA).

Expression of the *Penicillium emersonii* Carboxypeptidase Gene in *Aspergillus oryzae*

*Aspergillus oryzae* strain MT3568 was used for heterologous expression of the gene encoding the *Penicillium emersonii* carboxypeptidase gene. *A. oryzae* MT3568 is an amdS (acetamidase) disrupted derivative of *A. oryzae* JaL355 (WO02/40694) in which pyrG auxotrophy was restored by disrupting the *A. oryzae* acetamidase (amdS) gene with the pyrG gene.

Protoplasts were prepared according to the method described as "Transformation of *Aspergillus* Expression Host" in Example 2 of US20140179588 A1. Three μg of p505-S10_Pe1 were used to transform *Aspergillus oryzae* MT3568.

The transformation of *Aspergillus oryzae* MT3568 with p505-S10_Pe1 yielded about 10 transformants. Four transformants were isolated to plate for resolution and were then inoculated separately into 3 ml of YPM medium in 24-well plate and incubated at 30° C., 150 rpm. After 3 days incubation, 20 μl of supernatant from each culture were analyzed on NUPAGE® NOVEX® 4-12% Bis-Tris Gel with 50 mM MES (Invitrogen Corporation, Carlsbad, Calif., USA) according to the manufacturer's instructions. The resulting gel was stained with INSTANTBLUE™ (Expedeon Ltd., Babraham Cambridge, UK). SDS-PAGE profiles of the cultures showed that the majority of the transformants had a smear band of approximately 60 kDa. The expression strain was designated as O82P5E.

Fermentation of *Aspergillus oryzae* Expression Strain O82P5E

Two slants of the expression strain O82P5E, was washed with 10 ml of YPM and inoculated into 18 2-liter flasks each containing 400 ml of YPM medium, shaking at 30 C, 80 rpm. The culture was harvested on day 3 and filtered using a 0.45 μm DURAPORE Membrane (Millipore, Bedford, Mass., USA).

Example 2

Purification of Recombinant Carboxypeptidase by Hydrophobic Interaction Chromatography (HIC)

The culture broth harvested in example 1 was precipitated with ammonium sulfate (80% saturated). Precipitates were re-dissolved in 200 ml of 20 mM phosphate-buffered saline (PBS) pH 6.0, and ammonium sulfate was replenished to get final concentration 1.2 M. Crude protein solution was filtered through a 0.45 μm filter, and then applied to a 50 ml self-packed Phenyl Sepharose 6 Fast Flow (low sub) column (GE Healthcare, Buckinghamshire, UK) equilibrated with 20 mM PBS pH 6.0 and 1.2 M ammonium sulfate buffer. Proteins were eluted with a linear 1.2 M-0 M ammonium sulfate gradient. Fractions were analyzed by SDS-PAGE using a Mini-PROTEAN TGX Stain-Free 4-15% Precast Gel (Bio-Rad Laboratories, CA, United States). Carboxypeptidase activities of fractions were assessed by halo zone assay on skim-milk agarose plate at pH 5.0, 50° C. Fractions were pooled containing recombinant protein bands and showing positive activities. Then the pooled solution was concentrated by ultrafiltration.

Example 3

Cloning and Expression of a S10 Peptidase from *Myceliophthora heterothallica* Gene A fungal strain was isolated and based on both morphological and molecular characterization (ITS sequencing) classified as *Myceliophthora heterothallica*. The *Myceliophthora heterothallica* strain was annotated as *Myceliophthora heterothallica* CBS 202.75 strain and fully genome sequenced. The genomic DNA sequence of a S10 peptidase polypeptide encoding sequence was identified in the genome of *Myceliophthora heterothallica* CBS 202.75 strain and the genomic DNA sequence and deduced amino acid sequence are shown in SEQ ID NO: 3 and SEQ ID NO: 4, respectively. The genomic DNA sequence of 1720 nucleotides contains 1 intron of 55 bp (nucleotides 503 to 557). The genomic DNA fragment encodes a polypeptide of 554 amino acids.

Expression Vector

The *Aspergillus* expression vector pDau109 (WO 2005/042735) consists of an expression cassette based on the partly duplicated *Aspergillus niger* neutral amylase II (NA2) promoter fused to the *Aspergillus nidulans* triose phosphate isomerase non translated leader sequence (Pna2/tpi) and the *Aspergillus niger* amyloglycosidase terminator (Tamg). Also present on the vector is the *Aspergillus* selective marker amdS from *Aspergillus nidulans* enabling growth on acetamide as sole nitrogen source and the amplicillin resistance gene (beta lactamase) allowing for facile selection for positive recombinant *E. coli* clones using commercially available and highly competent strains on commonly used LB ampicillin plates. pDau109 contains a multiple cloning site situated between the promoter region and terminator, allowing for insertion of the gene of interest in front of the promoter region.

Expression Cloning

The gene encoding the *Myceliophthora heterothallica* CBS 202.75 S10 peptidase (SEQ ID NO: 3) was PCR amplified from genomic DNA isolated from *Myceliophthora heterothallica* CBS 202.75 strain. The PCR product encoding the *Myceliophthora heterothallica* CBS 202.75 S10 peptidase (SEQ ID NO: 3) was cloned into the pDau109 *Aspergillus* expression vector using the unique restriction sites BamHI and HindIII and transformed into *E. coli* (Top10, Invitrogen). Expression plasmids containing the insert were purified from the *E. coli* transformants, and sequenced with vector primers and gene specific primers in order to determine a representative plasmid expression clone that was free of PCR errors. The plasmid expression clone was transformed into *A. oryzae* and a recombinant *A. oryzae* clone containing the integrated expression construct were grown in liquid culture. Expression of the *Myceliophthora heterothallica* CBS 202.75 S10 peptidase was verified by SDS-page. The enzyme containing supernatant was sterile filtered before purification.

Example 4

Purification Assay:
Substrate: Z-Ala-Phe-OH(Sachem C-1155).
Temperature: 37° C.
Assay buffer: 100 mM succinic acid, 100 mM HEPES, 100 mM CHES, 100 mM CABS, 1 mM $CaCl_2$, 150 mM KCl, 0.01% Triton X-100, pH 6.0.

100 µl Z-Ala-Phe-OH substrate (50 mg dissolved in 1.0 ml DMSO and further diluted 25× in 0.01% Triton X-100) was mixed with 1541 Assay buffer in an Eppendorf tube and placed on ice. 50 µl peptidase sample (diluted in 0.01% Triton X-100) was added. The assay was initiated by transferring the Eppendorf tube to an Eppendorf thermomixer, which was set to 37° C. The tube was incubated for 15 minutes on the Eppendorf thermomixer at its highest shaking rate (1400 rpm.). The tube was then transferred back to the ice bath and when the tube had cooled, 500 µl Stop reagent (17.9 g TCA+29.9 g Na-acetate trihydrate+19.0 ml conc. $CH_3COOH$ and deionised water ad 500 ml) was added and the tube was vortexed and left for 15 min at room temperature (to ensure complete precipitation). The tube was centrifuged (15000×g, 3 min, room temp), 30 µl supernatant was transferred to a microtiter plate and 225 µl freshly prepared OPA-reagent (3.81 g disodium tetraborate and 1.00 g SDS were dissolved in approx. 80 ml deionised water—just before use 80 mg ortho-phtaldialdehyde dissolved in 2 ml ethanol was added and then 1.0 ml 10% (w/v) DIE and finally the volume was adjusted ad 100 ml with deionised water) was added. After 2 minutes, $A_{340}$ was read in a MTP reader. The $A_{340}$ measurement relative to an enzyme blind (50 µl 0.01% Triton X-100 instead of peptidase sample) was a measure of carboxypeptidase activity.

Purification of the 510 Carboxypeptidase from *Myceliophthora heterothallica*:

(The S10 Carboxypeptidase was Expressed in *A. oryzae*.)

The culture broth was centrifuged (20000×g, 20 min) and the supernatant was carefully decanted from the precipitate. The supernatant was filtered through a Nalgene 0.2 µm filtration unit in order to remove the rest of the *Aspergillus* host cells. The 0.2 µm filtrate was transferred to 20 mM MES/NaOH, 0.5 mM $CaCl_2$, pH 6.0 on a G25 sephadex column (from GE Healthcare). The G25 sephadex transferred carboxypeptidase was applied to a Q-sepharose FF column (from GE Healthcare) equilibrated in 20 mM MES/NaOH, pH 6.0. After washing the column extensively with the equilibration buffer, the S10 carboxypeptidase was eluted with a linear gradient between the equilibration buffer and 20 mM MES/NaOH, 5 mM $CaCl_2$, 500 mM NaCl, pH 6.0 over five column volumes. The eluted fractions were analysed for carboxypeptidase activity and active fractions were further analysed by SDS-PAGE. Fractions with one band at approx. 50 kDa were pooled as the purified product and was used for further characterization.

Characteristics for the Purified S10 Carboxypeptidase from *Myceliophthora heterothallica*:

The relative molecular weight as determined by SDS-PAGE was approx. Mr=50 kDa.

The major N-terminal sequence determined by EDMAN degradation was: TVDPSKL (60%). Two minor N-terminal sequences were also determined: KTVDPSK (20%) and VKTVDPS (20%) suggesting that that the N-termini were somewhat ragged.

The S10 carboxypeptidase from *Myceliophthora heterothallica* was glycosylated and therefore the purified carboxypeptidase was treated with Endo H before Intact MS analysis. The measured peak pattern could be assigned to the mature sequence.

Example 5

Cloning and Expression of a SIC Peptidase from *Chaetomium strumarium* Gene

A fungal strain was isolated and based on both morphological and molecular characterization (ITS sequencing) classified as *Chaetomium strumarium*. The *Chaetomium strumarium* strain was annotated as *Chaetomium strumarium* strain and fully genome sequenced. The genomic DNA sequence of a S10 peptidase polypeptide encoding sequence was identified in the genome of *Chaetomium strumarium* strain and the genomic DNA sequence and deduced amino acid sequence are shown in SEQ ID NO: 5 and SEQ ID NO: 6, respectively. The genomic DNA sequence of 1722 nucleotides contains 1 intron of 57 bp (nucleotides 503 to 559). The genomic DNA fragment encodes a polypeptide of 554 amino acids.

Expression Vector

The *Aspergillus* expression vector pDau109 (WO 2005/042735) consists of an expression cassette based on the partly duplicated *Aspergillus niger* neutral amylase II (NA2) promoter fused to the *Aspergillus nidulans* triose phosphate isomerase non translated leader sequence (Pna2/tpl) and the *Aspergillus niger* amyloglycosidase terminator (Tamg). Also present on the vector is the *Aspergillus* selective marker amdS from *Aspergillus nidulans* enabling growth on acetamide as sole nitrogen source and the ampicillin resistance gene (beta lactamase) allowing for facile selection for positive recombinant *E. coli* clones using commercially available and highly competent strains on commonly used LB ampicillin plates. pDau109 contains a multiple cloning site situated between the promoter region and terminator, allowing for insertion of the gene of interest in front of the promoter region.

Expression Cloning

The gene encoding the *Chaetomium strumarium* S10 peptidase (SEQ ID NO: 5) was PCR amplified from genomic DNA isolated from *Chaetomium strumarium* strain. The PCR product encoding the *Chaetomium strumarium* S10 peptidase (SEQ ID NO: 5) was cloned into the pDau109 *Aspergillus* expression vector using the unique restriction sites BamHI and HindIII and transformed into *E. coli* (Top10, Invitrogen). Expression plasmids containing the insert were purified from the *E. coli* transformants, and sequenced with vector primers and gene specific primers in order to determine a representative plasmid expression clone that was free of PCR errors. The plasmid expression clone was transformed into *A. oryzae* and a recombinant *A. oryzae* clone containing the integrated expression construct were grown in liquid culture. Expression of the *Chaetomium strumarium* S10 peptidase was verified by SDS-page. The enzyme containing supernatant was sterile filtered before purification.

Example 6

Strains

The strain *Lasiodiplodia theobromae* was isolated from soil, Yunnan, China in 1999.

Cloning of S10 Carboxypeptidase from *Lasiodiplodia theobromae*

The carboxypeptidase with nucleotide sequence SEQ ID NO: 7 was PCR amplified from genomic DNA isolated from *Lasiodiplodia theobromae* and cloned into the expression vector pCaHj505 (WO2013029496).

The final expression plasmid was transformed into the *Aspergillus oryzae* MT3568 expression host. *A. oryzae* MT3568 is a derivative of *A. oryzae* JaL355 (WO02/40694) in which pyrG auxotrophy was restored by disrupting the *A. oryzae* acetamidase (amdS) gene with the pyrG gene. The carboxypeptidase gene was integrated by homologous recombination into the *A. oryzae* MT3568 host cell genome upon transformation.

The gene coding for amdS was used as marker. Transformants were selected on pyrG media agar supplemented with 10 mM acetamide. One recombinant *Aspergillus oryzae* clone containing the carboxypeptidase expression construct was selected and was cultivated on a rotary shaking table in 4 2-liter baffled Erlenmeyer flasks each containing 400 ml YPM (1% Yeast extract, 2% Peptone and 2% Maltose). After 3 days cultivation time at 30° C., enzyme containing supernatants were harvested by filtration using a 0.22 µm 1-liter bottle top vacuum filter (Corning Inc., Corning, N.Y., USA). The protein sequence is SEQ ID NO: 8.

Example 7

Purification:

The culture supernatant of O23GV9 was firstly precipitated with ammonium sulfate (80% saturation), then dialyzed with 20 mM Bis-Tris at pH7.5. The solution was filtered with 0.45 um filter and then loaded into Q Sepharose Fast Flow column (GE Healthcare) equilibrated with 20 mM Bis-Tris at pH7.5. A gradient of NaCl concentration from zero to 1M was applied as elution buffer, and then elution fractions and flow-through fraction were collected separately for SDS-PAGE analysis. The fractions with target protein were pooled together for evaluation.

Example 8

Strain

A fungal strain designated was isolated from a soil sample collected from Yunnan Province, China, by dilution on PDA plates at 45° C. and then purified by transferring a single conidium onto a YG agar plate. The strain was identified as *Thermoascus aurantiacus*, based on both morphological characteristics and ITS rDNA sequence.

Media

PDA medium was composed of 39 grams of potato dextrose agar and deionized water to 1 liter.

YPG medium contained 0.4% of yeast extract, 0.1% of $KH_2PO_4$, 0.05% of $MgSO_4.7H_2O$, 1.5% glucose in deionized water.

YPM medium contained 1% yeast extract, 2% of peptone, and 2% of maltose in deionized water.

Genomic DNA Extraction of *Thermoascus aurantiacus*

*Thermoascus aurantiacus* strain was inoculated onto a PDA plate and incubated for 3 days at 45° C. in the darkness. Several mycelia-PDA plugs were inoculated into 500 ml shake flasks containing 100 ml of YPG medium. The flasks were incubated for 3 days at 45° C. with shaking at 160 rpm. The mycelia were collected by filtration through MIRACLOTH®) and frozen in liquid nitrogen. Frozen mycelia were ground, by a mortar and a pestle, to a fine powder, and genomic DNA was isolated using a DNeasy® Plant Maxi Kit following the manufacturer's instructions.

Genome Sequencing, Assembly and Annotation

The extracted genomic DNA samples were delivered to Beijing Genome Institute (BGI, Shenzhen, China) for genome sequencing using an ILLUMINA® GA2 System (Illumina, Inc., San Diego, Calif., USA). The raw reads were assembled at BGI using program SOAPdenovo (Li et al., 2010, *Genome Research* 20(2): 265-72). The assembled sequences were analyzed using standard bioinformatics methods for gene finding and functional prediction. GeneID (Parra et al., 2000, *Genome Research* 10(4): 511-515) was used for gene prediction. Blastall version 2.2.10 (Altschul et al., 1990, *J. Mol. Biol.* 215 (3): 403-410, National Center for Biotechnology Information (NCBI), Bethesda, Md., USA) and HMMER version 2.1.1 (National Center for Biotechnology Information (NCBI), Bethesda, Md., USA) were used to predict function based on structural homology. The carboxypeptidase gene, S10_Ta, was identified directly by analysis of the Blast results. The Agene program (Munch and Krogh, 2006, *BMC Bioinformatics* 7: 263) and SignalP program (Nielsen et al., 1997, *Protein Engineering* 10: 1-6) were used to identify start codons. The SignalP program was further used to predict signal peptides. Pepstats (Rice et al., 2000, *Trends Genet.* 16(6): 276-277) was used to predict the isoelectric points and molecular weights of the deduced amino acid sequences.

Cloning of the Carboxypeptidase Genes of *Thermoascus aurantiacus* from Genomic DNA The expression vector pCaHj505 was used for gene cloning. It contained the TAKA-amylase promoter derived from *Aspergillus oryzae* and the *Aspergillus niger* glucoamylase terminator elements. Furthermore pCaHj505 had pUC18 derived sequences for selection and propagation in *E. coli*, and an amdS gene, which encoded an acetoamidase gene derived from *Aspergillus nidulans* for selection of an amdS+ *Aspergillus* transformant.

The carboxypeptidase gene, S10_Ta, SEQ ID NO: 9 for the genomic DNA sequence and SEQ ID NO: 10 for the deduced amino acid sequence, was selected for expression cloning.

Based on the DNA information obtained from genome sequencing, oligonucleotide primers, shown below, were designed to amplify the coding sequence of the carboxypeptdase genes from the genomic DNA of *Thermoascus aurantiacus* NN044936. The primers were synthesized by Invitrogen, Beijing, China.

```
Primer1:
                                           [SEQ ID NO: 19]
5' ACACAACTGGGGATC CACC atgttgggctacgggctgttg 3'

Primer2:
                                           [SEQ ID NO: 20]
5' CCCTCTAGATCTCGAG ggaatggcatcagatcagatcaga 3'
```

Lowercase characters of the forward primer represent the coding region of the gene and lowercase characters of the reverse primer represent the flanking region of the gene, while captalized characters represent a region homologous to insertion sites of pCaHj505 (WO2013029496). The 4 underlined characters ahead of the coding sequence in the forward primer represent the Kozak sequence as the initiation of translation process.

Ten picomoles of the forward and reverse primers above, primer1 and primer2 were used in a PCR reaction for amplification of the *Thermoascus aurantiacus* carboxypeptidase gene S10_Ta. The PCR reaction was composed of 2 µl of genomic *Thermoascus aurantiacus*, 10 µl of 5× Phusion® HF Buffer (Finnzyrnes Oy, Espoo, Finland), 1.5 µl of DMSO, 1.5 ul of 2.5 mM each of dATP, dTTP, dGTP, and dCTP, and 0.6 unit of PHUSION™ High Fidelity DNA Polymerase (Finnzymes Oy, Espoo, Finland) in a final volume of 50 µl. The amplification was performed using a Peltier Thermal Cycler (MJ Research Inc., South San Francisco, Calif., USA) programmed for denaturing at 98° C. for 1 minute; 7 cycles of denaturing each at 98° C. for 30 seconds, annealing at 65° C. for 30 seconds with 1° C. decrease per cycle, and elongation at 72° C. for 2 minutes; 25 cycles each at 94° C. for 30 seconds, 60° C. for 30 seconds, and 72° C. for 2 minutes; and a final extension at 72° C. for 5 minutes. The heat block then went to a 4° C. soak cycle.

The PCR product was isolated by 1.0% agarose gel electrophoresis using 90 mM Trisborate and 1 mM EDTA (TBE) buffer where a single product band of approximately 2.3 kb from the reaction was visualized under UV light. The PCR product was then purified from solution by using an Illustra™ GFX™ PCR DNA and Gel Band Purification Kit (GE Healthcare, Buckinghamshire, UK) according to the manufacturer's instructions.

Plasmid pCaHj505 was digested with Bam HI and Xho I, isolated by 1.0% agarose gel electrophoresis using TBE buffer, and purified using an ILLUSTRA™ GFX™ PCR DNA and Gel Band Purification Kit according to the manufacturer's instructions.

In-Fusion® HD Cloning Kit (Clontech Laboratories. Inc., Mountain View, Calif., USA) was used to clone the PCR fragment directly into the expression vector pCaHj505, without the need for restriction digestion.

The purified PCR fragment and the digested vector were ligated together using the In-Fusion® HD Cloning Kit according to the manufacturer's instructions resulting in plasmid p505-S10_Ta, in which the transcription of the carboxypeptidase polypeptide coding sequence was under the control of an *Aspergillus oryzae* alpha-amylase gene promoter. In brief, 0.8 ul of 30 ng/ul of pCaHj505, digested with Bam HI and Xho I, and 3.2 ul of the purified PCR fragment containing ~60 ng of the *Thermoascus aurantiacus* carboxypeptidase gene PCR fragment were added to 1 ul of 5× In-Fusion® HD Enzyme Premix. The reaction was incubated at 50° C. for 15 minutes. The ligation reaction was used to transform *E. coli* TOP10 competent cells (TIANGEN Biotech Co. Ltd., Beijing, China). *E. coli* transformants containing an expression construct were detected by colony PCR. Colony PCR is a method for quick screening of plasmid inserts directly from *E. coli* colonies. Briefly, a single colony was transferred to a premixed PCR solution in a PCR tube, including PCR buffer, $MgCl_2$, dNTPs, Taq DNA polymerase and primer pairs from which the PCR fragment was generated. Several colonies were screened. After the PCR, reactions were analyzed by 1.0% agarose gel electrophoresis using TBE buffer. Plasmid DNA was prepared using a QIAPREP® Spin Miniprep Kit (QIAGEN GmbH, Hilden, Germany) from the colony showing an insert with the expected size. The carboxypeptidase gene coding sequence inserted in p505-S10_Ta was confirmed by DNA sequencing using 3730XL DNA Analyzers (Applied Biosystems Inc, Foster City, Calif., USA).

Expression of the *Thermoascus aurantiacus* Carboxypeptidase Gene in *Aspergillus oryzae*

*Aspergillus oryzae* strain MT3568 was used for heterologous expression of the gene encoding the *Thermoascus aurantiacus* carboxypeptidase gene. *A. oryzae* MT3568 is an amdS (acetamidase) disrupted derivative of *A. oryzae* JaL355 (WO02/40694) in which pyrG auxotrophy was restored by disrupting the *A. oryzae* acetamidase (amdS) gene with the pyrG gene.

Protoplasts were prepared according to the method described as "Transformation of *Aspergillus* Expression Host" in Example 2 of US20140179588 A1 Three µg of p505-S10_Ta were used to transform *Aspergillus oryzae* MT3568.

The transformation of *Aspergillus oryzae* MT3568 with p505-S10_Ta yielded about 10 transformants. Four transformants were isolated to plate for reisolation and were then inoculated separately into 3 ml of YPM medium in 24-well plate and incubated at 30° C., 150 rpm. After 3 days incubation, 20 µl of supernatant from each culture were analyzed on NUPAGE® NOVEX® 4-12% Bis-Tris Gel with 50 mM MES (Invitrogen Corporation, Carlsbad, Calif., USA) according to the manufacturer's instructions. The resulting gel was stained with INSTANTBLUE® (Expedeon Ltd., Babraham Cambridge, UK). SDS-PAGE profiles of the cultures showed that the majority of the transformants had a smear band of approximately 65 kDa. The expression strain was designated as O13U8S.

Fermentation of *Aspergillus oryzae* Expression Strain O13U8S.

A slant of the expression strain 013U8S, was washed with 10 ml of YPM and inoculated into 4 2-liter flasks each containing 400 ml of YPM medium, shaking at 30 C, 80 rpm. The culture was harvested on day 3 and filtered using a 0.45 μm DURAPORE Membrane (Millipore, Bedford, Mass., USA).

Example 9

Purification of Recombinant Carboxypeptidase by Hydrophobic Interaction Chromatography (HIC)

The culture broth harvested in example 8 was precipitated with ammonium sulfate (80% saturated). Precipitates were re-dissolved in 80 ml of 20 mM PBS pH 6.0, and ammonium sulfate was replenished to get final concentration 1.2 M. Crude protein solution was filtered through a 0.45 μm filter, and then applied to a 50 ml self-packed Phenyl Sepharose 6 Fast Flow (low sub) column (GE Healthcare, Buckinghamshire, UK) equilibrated with 20 mM PBS pH 6.0 and 1.2 M ammonium sulfate buffer. Proteins were eluted with a linear 1.2 M-0 M ammonium sulfate gradient. Fractions were analyzed by SDS-PAGE using a Mini-PROTEAN TGX Stain-Free 4-15% Precast Gel (Bio-Rad Laboratories, CA, United States). Carboxypeptidase activities of fractions were assessed by halo zone assay on skim-milk agarose plate at pH 5.0, 50° C. Fractions were pooled containing recombinant protein bands and showing positive activities. Then the pooled solution was concentrated by ultrafiltration.

Example 10

Testing the Carboxypeptidase Specificity According to Assay I and II

The activity of carboxypeptidases of SEQ ID NO: 2, 4, 6, 8 and 10 were tested in Assay I and II together with two benchmark carboxypeptidases, i.e. CP1 (SEQ ID NO: 15) and CPY (SEQ ID NO: 14) from *A. oryzae*. Results are given in the below table 2. Calculated values for ACHA, ACLA and Pro/ACHA*100 are given in table 3.

TABLE 2

Activity of different carboxypeptidases as measured in Assay I and Assay II

|     | SEQ ID NO: 2 | SEQ ID NO: 4 | SEQ ID NO: 6 | SEQ ID NO: 10 | SEQ ID NO: 8 | SEQ ID NO: 14 | SEQ ID NO: 15 |
|-----|------|------|------|------|------|------|------|
| Pro | 0.35 | 0.18 | 0.22 | 0.04 | 0.01 | 0.13 | 0.02 |
| Ala | 0.46 | 0.33 | 0.39 | 0.05 | 0.01 | 0.28 | 0.12 |
| Val | 0.57 | 0.56 | 0.57 | 0.09 | 0.03 | 0.55 | 0.22 |
| Leu | 0.59 | 0.61 | 0.57 | 0.04 | 0.03 | 0.60 | 0.21 |
| Ile | 0.63 | 0.61 | 0.59 | 0.09 | 0.02 | 0.57 | 0.25 |
| Met | 0.59 | 0.57 | 0.58 | 0.08 | 0.03 | 0.54 | 0.21 |
| Phe | 0.60 | 0.59 | 0.59 | 0.03 | 0.02 | 0.56 | 0.16 |
| Trp | 0.49 | 0.40 | 0.44 | 0.06 | 0.02 | 0.38 | 0.15 |
| Gly | 0.05 | 0.03 | 0.03 | 0.01 | 0.00 | 0.01 | 0.01 |
| Ser | 0.15 | 0.07 | 0.09 | 0.04 | 0.01 | 0.05 | 0.08 |
| Tyr | 0.44 | 0.44 | 0.44 | 0.05 | 0.03 | 0.31 | 0.12 |
| Asn | 0.14 | 0.06 | 0.07 | 0.05 | 0.00 | 0.04 | 0.09 |
| Gln | 0.00 | 0.04 | 0.02 | 0.01 | 0.05 | 0.07 | 0.01 |
| Asp | 0.04 | 0.01 | 0.02 | 0.01 | 0.00 | 0.01 | 0.01 |
| Glu | 0.02 | 0.01 | 0.01 | 0.01 | 0.00 | 0.01 | 0.02 |
| His | 0.08 | 0.05 | 0.06 | 0.06 | 0.00 | 0.02 | 0.07 |
| Lys | 0.00 | 0.01 | 0.00 | 0.22 | 0.24 | 0.11 | 0.32 |
| Arg | 0.03 | 0.01 | 0.01 | 0.23 | 0.14 | 0.02 | 0.23 |

The result show that the carboxypeptidases of SEQ ID NO: 2, 4 and 6 all have an activity of at least 0.15 on Proline, whereas the prior art carboxypeptidase CPY has an activity of 0.13.

TABLE 3

Average activity on hydrophobic amino acids excluding Pro (ACHA) and relative activity on Pro compared to average activity on hydrophobic amino acids excluding Pro (Pro/ACHA*100). Average activity on lys, Arg (ACLA) and relative activity on Lys, Arg compared to average activity on hydrophobic amino acids excluding Pro (ACLA/ACHA).

|     | SEQ ID NO: 2 | SEQ ID NO: 4 | SEQ ID NO: 6 | SEQ ID NO: 10 | SEQ ID NO: 8 | SEQ ID NO: 14 | SEQ ID NO: 15 |
|-----|------|------|------|------|------|------|------|
| ACHA | 0.56 | 0.52 | 0.53 | 0.06 | 0.02 | 0.50 | 0.19 |
| Pro/ACHA *100 | 61 | 35 | 42 | 58 | 53 | 25 | 11 |
| ACLA | 0.01 | 0.01 | 0.00 | 0.23 | 0.19 | 0.06 | 0.28 |
| ACLA/ACHA*100 | 2 | 2 | 0 | 364 | 854 | 12 | 146 |

As seen in the table the new carboxypeptidases are all characterised by having a higher ratio of activity on Pro versus average activity on hydrolphobic amino acids (Pro/ACHA*100) compared to the benchmark carboxypeptidases (SEQ ID NO: 14 and 15).

Example 11

Testing of Carboxy-Peptidases in Soy and Gluten on Top of Alcalase and Flavourzyme in Small Scale The carboxy-peptidases (exo-peptidases) were screened on top of Alcalase (Alc) and Flavourzyme (FZ using a 6% protein suspension of either soy bean meal or wheat gluten.

Incubation was done in a Deep Well Plate (DWP) with shaking overnight. After incubation the samples were diluted in MQ water and analysed using the OPA assay (Assay V).

Substrate:

Soy bean meal: Protein content: 52% w/w on soy bean meal

Wheat gluten: Protein content: 73.3% w/w on wheat gluten

Enzymes and Dosages:

Alcalase AF 2.4 L: 0.4% on protein

Flavourzyme 1000 L: 0.8% on protein

Exo-peptidase candidate: 1.5-2 mg enzymeprotein/g protein

DWP: 1 ml DPW, wide-bottomed to ensure mixing; incubation in Eppendorf Thermomixer Incubation:

Temperature: 55° C.

pH as is: 6.0-6.5

Shaking: 1200 rpm

Time: overnight, 18-19 hrs

Set-Up:

DPW assay: Suspensions of the substrates were made giving a final protein concentration of 6.5% based on the protein content given above, and considering the further dilution of the substrate when enzymes were added. Total volume in the wells were 285 ul. All enzymes were diluted as appropriate before addition. Substrates were pretreated using Alcalase and Flavourzyme to ensure that dispensing into the wells were possible. Alcalase and Flavourzyme were therefore added to a larger portion of the substrate and the mixture incubated at 55'C for 50-60 min. 245 ul substrate per well was then transferred to the MWP and 40 ul of the exo-peptidase added.

The outer column and row of the deep well plate were not used due to temperature fluctuations. Samples were run in quadruplicate and a sample holding Alcalase and Flavourzyme included as a reference. Plates were left overnight in a Thermomixer. After incubation the samples were diluted in MQ water (e.g. 15 ul in 985 ul, DWP) and the degree of hydrolysis determined using an OPA assay (Assay V). Samples were analysed within 20 min, since no inactivation of the samples were done.

Results are given in the tables 4-5 below. DH of the sample having only Alcalase and Flavourzyme were set as 100% and the response of the samples with exo-peptidase on top of Alcalase and Flavourzyme compared to this. Benchmark enzymes included were SEQ ID NO: 14 a carboxy-peptidase from *A. oryzae* with preference for hydrophobic amino acids and SEQ ID NO: 15 a carboxypeptidase from *A. oryzae* with preference for basic amino acids but also activity on hydrophobic amino acids.

As seen the top candidate in both soy and gluten were enzyme sample SEQ ID NO: 2, characterised as a carboxy-peptidase with a high activity on hydrophobic amino acids in general, and with a high activity on Pro in particular. Table 1: Final DH obtained in soy hydrolysates relative to the DH of the sample with background enzymes (Alcalase+Flavourzyme) set to 100. Dosages of exo-candidates were 2 mg enzyme protein/g protein except for SEQ ID NO: 4 and SEQ ID NO: 6 where dosages were 1.5 and 1.8 mg ep/g protein respectively.

TABLE 4

| Enzyme ID | $DH/DH_{Alc+FZ}*100$ |
| --- | --- |
| SEQ ID NO: 2 | 200 |
| SEQ ID NO: 4 | 169 |
| SEQ ID NO: 10 | 166 |
| SEQ ID NO: 6 | 160 |
| SEQ ID NO: 8 | 151 |
| SEQ ID NO: 14 = CPY | 141 |
| SEQ ID NO: 15 = CP1 | 138 |

TABLE 5

Final DH obtained in gluten hydrolysates relative to the DH of the sample with background enzymes (Alcalase + Flavourzyme) set to 100. Dosages of exo-candidates were 2 mg enzyme protein/g protein except for SEQ ID NO: 6 where 1.8 mg ep/g protein was used.

| Enzyme ID | $DH/DH_{Alc+FZ}*100$ |
| --- | --- |
| SEQ ID NO: 2 | 157 |
| SEQ ID NO: 10 | 154 |
| SEQ ID NO: 6 | 150 |
| SEQ ID NO: 15 = CP1 | 151 |
| SEQ ID NO: 4 | 144 |
| SEQ ID NO: 8 | 136 |
| SEQ ID NO: 14 = CPY | 120 |

Example 12

Testing of Carboxy-Peptidase in Soy on Top of Alcalase

Further small scale tests in the DWP set-up were done combining carboxy-peptidase and aminopeptidase (AP2) in soy and using either 0.5% Alcalase and 1% Flavourzyme as a background or 0.5% Alcalase alone. Dosage of exo-peptidase were 1 mg ep/g protein both when used alone or in combinations. Results are shown in table 6.

When using single candidates, results showed that SEQ ID NO: 2 was clearly superior giving the highest DH both when combined with Alcalase alone (DH 37) or with Alcalase and Flavourzyme (DH 46). When added on top of Alcalase only, the performance of SEQ ID NO: 2 was better than when using 1% FZ (37 vs. 28) on top of Alcalase. Performance of SEQ ID NO: 15 and SEQ ID NO: 16 were comparable both when added on top of Alc+Fz and when used with Alc only. The combined treatment showed the highest final DH value.

TABLE 6

DH obtained when hydrolysing soy protein with best candidates. Background was 0.5% Alc +/- 1% FZ. Candidates were dosed 1 mg ep/g protein in single treatments and 1 + 1 mg ep/g protein in combined treatment.

| | Alcalase | Alcalase + Flavourzyme |
| --- | --- | --- |
| Background | 14 | 28 |
| +SEQ ID NO: 16 | 26 | 37 |
| +SEQ ID NO: 15 | 27 | 37 |
| +SEQ ID NO: 2 | 37 | 46 |
| +SEQ ID NO: 2 + SEQ ID NO: 16 + SEQ ID NO: 15 | 54 | 55 |

Example 13: Testing of Best Candidate in Dose Response in Soy or Gluten on Top of Alcalase and Flavourzyme Dose response of the best candidate, carboxypeptidase SEQ ID NO: 2 was done in soy on a background of 0.8%

Alcalase+1.6% Flavourzyme and in gluten on a background of 0.4% Alcalase+0.8% Flavourzyme. Test were run in the DWP set-up. Results are given in table www and show a significant effect on DH also at the lowest dosages.

TABLE 7

% DH obtained when hydrolysing soy or gluten with best exo-peptidase in increasing dosage.

| Mg ep/g protein of carboxypeptidase | Soy | Gluten |
|---|---|---|
| 0 (=Background) | 23 | 31 |
| +0.5 | 40 | 46 |
| +1.0 | 42 | 48 |
| +1.5 | 44 | 47 |
| +2.0 | 46 | 49 |

Example 14: Testing of Carboxy-Peptidases in Soy and Gluten on Top of Alcalase and Flavourzyme in 25 g Scale 25 g scale: Substrate suspensions were prepared as above and Alcalase and Flavourzyme added for pretreatment. Compared to the DWP assay dosages of Alcalase and FZ was doubled (0.8% and 1.6%). After incubation for 50 min at 55° C., 21.5 g substrate was transferred to 50 ml blue cap flasks and 3.5 g of the diluted exo-peptidase added (1 mg enzyme protein/g protein). Combinations of a carboxypeptidase and an aminopeptidase were also tested. Dosages were 1+1 mg ep/g protein. Flasks were held in a heated water bath (55° C.) with magnetic stirring. After overnight incubation (20 hrs), 1.8 ml samples were withdrawn and enzymes inactivated in a Thermomixer at 95° C. for 10 min. Samples were diluted and analysed using OPA assay (Assay V).

Results are given in table 8 and show that the best performing candidate (SEQ ID NO: 2) identified in the smaller scale assay (DWP) also proved superior in larger scale.

TABLE 8

DH obtained in 25 g scale when hydrolysing soy or gluten protein with best candidates. Background was 0.8% Alc + 1.6% FZ. Candidates were dosed 1 mg ep/g protein in single treatments and 1 + 1 mg ep/g protein in combined treatments.

| | Soy | | Gluten | |
|---|---|---|---|---|
| | DH | Delta DH | DH | Delta DH |
| Background | 37 | | 45 | |
| +SEQ ID NO: 16 | 46 | 9 | 48 | 3 |
| +SEQ ID NO: 15 | 47 | 10 | 53 | 8 |
| +SEQ ID NO: 2 | 53 | 16 | 53 | 8 |
| +SEQ ID NO: 2 + SEQ ID NO: 16 | 65 | 28 | 58 | 13 |
| +SEQ ID NO: 15 + SEQ ID NO: 16 | 55 | 18 | 58 | 13 |

Background or reference DH obtained in the larger scale assay was clearly higher than in the DWP assay, which could be expected since the background dosages of Alcalase and FZ were higher. In addition to higher enzyme dosage improved mixing in larger scale might also increase hydrolysis.

Looking at the effect of the single candidates in the 25 g scale experiment and the combined treatments using one carboxypeptidase+one aminopeptidase, overall effects on DH seemed to be more or less additive.

Amino Acids Analysis

Results of analysing the amino acid composition of the hydrolysates are shown in table 9.

TABLE 9

Amino acids in soy or gluten hydrolysates using the best candidates on a background of 0.8% Alcalase and 1.6% Flavourzyme. Data are mg/L amino acids and summed per amino acid characteristics. Groups are: Hydrophobic amino acids consisting of: Ala, Val, Met, Trp, Phe, Ile, & Leu; Pro is given separately; Polar uncharged amino acids consisting of: Asn, Ser, Gln, Thr, Tyr & His/Gly (His/Gly could not be separated on the column so His is included in the polar uncharged group, even though it is a basic amino acid); Acidic amino acids consisting of: Glu & Asp; and Basic amino acids consisting of: Lys & Arg. Cys was not analysed.

| | Amino acids, mg/L | | | | | |
|---|---|---|---|---|---|---|
| | Hydrophobic | Pro | Polar uncharged + His | Acidic | Basic | Sum |
| Soy | | | | | | |
| Background: | 7399 | 230 | 5104 | 2171 | 1455 | 16359 |
| +SEQ ID NO: 16 | 9426 | 239 | 8435 | 4200 | 4620 | 26921 |
| +SEQ ID NO: 15 | 11023 | 816 | 8864 | 3967 | 5253 | 29922 |
| +SEQ ID NO: 2 | 14038 | 957 | 9722 | 3417 | 4835 | 32968 |
| +SEQ ID NO: 2 + SEQ ID NO: 16 | 15433 | 790 | 12706 | 5254 | 6061 | 40245 |
| +SEQ ID NO: 15 + SEQ ID NO: 16 | 12820 | 642 | 11711 | 5957 | 5587 | 36717 |
| Gluten | | | | | | |
| Background | 11001 | 283 | 14657 | 2394 | 2347 | 30682 |
| +SEQ ID NO: 16 | 11714 | 647 | 17294 | 2848 | 2656 | 35159 |
| +SEQ ID NO: 15 | 12756 | 2174 | 18116 | 2704 | 2538 | 38297 |
| +SEQ ID NO: 2 | 14726 | 2580 | 18518 | 2724 | 2833 | 41381 |
| +SEQ ID NO: 2 + SEQ ID NO: 16 | 15629 | 3385 | 20557 | 2771 | 2412 | 44454 |
| +SEQ ID NO: 15 + SEQ ID NO: 16 | 14540 | 3025 | 22259 | 4072 | 2830 | 46726 |

As seen in the table the sum of free amino acids increased when the exo-peptidases were added on top of Alcalase and Flavourzyme. Best performance was achieved when combining carboxy, and aminopeptidases. Of the single candidates SEQ ID NO: 2 was superior, showing 100% increase in total amount of liberated amino acids in soy and 35% in gluten.

Example 15

Testing of Best Candidates at Higher Protein Concentration on Top of Alcalase

A wheat gluten suspension was made having a final protein concentration of 10% based on a protein content of 73.3% w/w as is in the vital wheat gluten and considering that the substrate was diluted further when enzymes were added, Hydrolysis was carried out in 2 ml Eppendorf tubes holding 1.8 ml substrate, incubated in an Eppendorf thermomixer with shaking (1200 rpm). Duplicate determinations were made. Incubation temperature was 55° C., and incubation time 18 hours. pH was not adjusted. Enzymes were inactivated by holding the samples at 90° C. for 10 min, and % DH (OPA analysis) and free amino acids (HPLC) were analyzed.

Amino Acids Analysis

Results of analysing the amino acid composition of the hydrolysate are shown in table ccc.

TABLE 10

DH (OPA assay V) and amino acids in gluten hydrolysates using the best candidates on a background of 1% Alcalase. Dosage of candidates were 0.5 mg ep/g protein and 0.5 + 0.5 mg ep/g protein in the combined treatment. Data are mg/L amino acids and are summed per amino acid characteristics. Groups are: Hydrophobic amino acids consisting of: Ala, Val, Met, Trp, Phe, Ile, & Leu; Pro is given separately; Polar uncharged amino acids consisting of: Asn, Ser, Gln, Thr, Tyr & His/Gly (His/Gly could not be separated on the column so His is included in the polar uncharged group, even though it is a basic amino acid); Acidic amino acids consisting of: Glu & Asp; and Basic amino acids consisting of: Lys & Arg. Cys was not analysed.

|  | % DH | mg/L Hydrophobic | Pro | Polar uncharged + His | Acidic | Basic | Sum |
|---|---|---|---|---|---|---|---|
| Background | 9 | 1433 | 35 | 1061 | 235 | 351 | 3125 |
| +SEQ ID NO: 15 | 21 | 6734 | 1569 | 9103 | 873 | 858 | 19137 |
| +SEQ ID NO: 2 | 30 | 11379 | 2323 | 9122 | 819 | 934 | 24576 |
| +SEQ ID NO: 8 | 25 | 7663 | 378 | 9813 | 1330 | 1753 | 20938 |
| +SEQ ID NO: 6 | 26 | 10083 | 1579 | 7694 | 685 | 841 | 20882 |
| +SEQ ID NO: 16 | 32 | 8076 | 38 | 13539 | 1251 | 1552 | 24455 |
| +SEQ ID NO: 15 + SEQ ID NO: 16 | 40 | 11506 | 930 | 19233 | 1958 | 1884 | 35511 |

As seen in the table, the sum of free amino acids increased significantly when the exo-peptidases were added on top of Alcalase. Best performance was achieved when combining carboxy, and aminopeptidases. Of the single candidates SEQ ID NO: 2 was superior, showing the highest amount of liberated amino acids, followed by SEQ ID NO: 16. For the carboxypeptidases (SEQ ID NO: 2 and SEQ ID NO: 6) especially levels of hydrophobic amino acids and Pro were high, while for the aminopeptidase (SEQ ID NO: 16) levels of polar uncharged, acidic and basic amino acids were high.

Example 16

Testing of best candidates in combination with aminopeptidase (SEQ ID NO: 16) at higher protein concentration on top of Alcalase Testing of the different carboxypetidases combined with aminopeptidase were done in a 10% wheat gluten protein suspension. The set-up was the same as the one used in Example 15.

TABLE 11

DH (OPA analysis) and amino acids in gluten hydrolysates using the best candidates combined with aminopeptidase on a background of 1% Alcalase. Dosage of carboxypeptidases and of aminopeptidase were: 0.5 mg ep/g protein. Data are mg/L amino acids and are summed per amino acid characteristics. Groups are: Hydrophobic amino acids consisting of: Ala, Val, Met, Trp, Phe, Ile, & Leu; Pro is given separately; Polar uncharged amino acids consisting of: Asn, Ser, Gln, Thr, Tyr & His/Gly (His/Gly could not be separated on the column so His is included in the polar uncharged group, even though this is a basic amino acid); Acidic amino acids consisting of: Glu & Asp; and Basic amino acids consisting of: Lys & Arg. Cys was not analysed.

|  | % DH | mg/L Hydrophobic | Pro | Polar uncharged + His | Acidic | Basic | Sum |
|---|---|---|---|---|---|---|---|
| Background | 10 | 1527 | 46 | 1119 | 241 | 382 | 3315 |
| +SEQ ID NO: 15 + SEQ ID NO: 16 | 48 | 13470 | 1038 | 21767 | 2087 | 1931 | 40293 |
| +SEQ ID NO: 2 + SEQ ID NO: 16 | 57 | 16649 | 2157 | 21379 | 2201 | 2218 | 44607 |

TABLE 11-continued

DH (OPA analysis) and amino acids in gluten hydrolysates using the best candidates combined with aminopeptidase on a background of 1% Alcalase. Dosage of carboxypeptidases and of aminopeptidase were: 0.5 mg ep/g protein. Data are mg/L amino acids and are summed per amino acid characteristics. Groups are: Hydrophobic amino acids consisting of: Ala, Val, Met, Trp, Phe, Ile, & Leu; Pro is given separately; Polar uncharged amino acids consisting of: Asn, Ser, Gln, Thr, Tyr & His/Gly (His/Gly could not be separated on the column so His is included in the polar uncharged group, even though this is a basic amino acid); Acidic amino acids consisting of: Glu & Asp; and Basic amino acids consisting of: Lys & Arg. Cys was not analysed.

| | % DH | Hydrophobic | Pro | Polar uncharged + His | Acidic | Basic | Sum |
|---|---|---|---|---|---|---|---|
| +SEQ ID NO: 10 + SEQ ID NO: 16 | 48 | 13525 | 945 | 21900 | 2112 | 1911 | 40392 |
| +SEQ ID NO: 6 + SEQ ID NO: 16 | 54 | 17883 | 1562 | 21490 | 2189 | 2398 | 45522 |

As seen in the table the sum of free amino acids increased significantly when the combination of carboxy-peptidases and aminopeptidase were added on top of alcalase. Best performance was achieved with the carboxypeptidases SEQ ID NO: 2 and SEQ ID NO: 6. Especially levels of hydrophobic amino acids and pro were high in these samples.

Example 17

Testing of Carboxy-Peptidases in Whey in Combination with Alcalase

Performance of the carboxy-peptidase (SEQ ID: 2) was compared to the benchmark enzymes CPY and CP1 (SEQ ID 14 and SEQ ID 15) when combined with Alcalase in a 6% whey protein solution at pH 7.5.

Substrate:
Whey Protein Isolate: Protein content: 90% w/w
Enzymes and Dosages:
Alcalase AF 2.4 L: 0.4% w/w on protein
Exo-peptidase candidate: 0.05-0.2 mg enzymeprotein/g protein
Incubation:
Temperature: 55° C.
pH: 7.5
Time: 4 hrs
Set-up Incubation was done in 50 ml glass flasks with stirring. After incubation pH was readjusted to 7.5 using NaOH and enzymes inactivated by holding the samples at 95° C. for 15 min (total time including heat-up). Samples were then diluted in MQ water and analysed using an OPA assay (Assay V).

Results are given in the table 12 below. DH of the sample with Alcalase alone was 14. Dosing of the carboxypeptidases were adjusted to give a final DH of approximately 20 in all samples. As seen, performance of SEQ ID: 2 was clearly superior, when comparing on enzyme protein dosage level, giving a final DH of 20.3 at a dosage of 0.05 mg enzyme protein/g protein. The benchmark enzymes had to be dosed at 0.1 and 0.2 mg ep/g, respectively, for a similar performance. This clearly illustrates the better performance and higher specific activity of the SEQ ID: 2 carboxypeptidase.

TABLE 12

Final DH obtained in whey protein hydrolysates. Dosage of Alcalase was 0.4%, and of exo-peptidases between 0.05 and 0.2 mg enzyme protein/g protein.

| Enzyme ID | DH |
|---|---|
| Alcalase 0.4% | 14 |
| Alcalase 0.4% + SEQ ID: 14, 0.1 mg ep/g | 20.5 |
| Alcalase 0.4% + SEQ ID: 15, 0.2 mg ep/g | 19.2 |
| Alcalase 0.4% + SEQ ID: 2, 0.05 mg ep/g | 20.3 |
| Alcalase 0.4% + SEQ ID: 2, 0.06 mg ep/g | 21.8 |
| Alcalase 0.4% + SEQ ID: 2, 0.1 mg ep/g | 23.5 |
| Alcalase 0.4% + SEQ ID: 2, 0.2 mg ep/g | 27.1 |

The invention claimed is:

1. A nucleic acid construct or expression vector comprising a polynucleotide encoding a polypeptide having carboxypeptidase activity, wherein the polypeptide has at least 99% sequence identity to the sequence of amino acids 1-426 of SEQ ID NO: 2 and wherein the polynucleotide is operably linked to one or more control sequences that direct the production of the polypeptide in a host cell.

2. The nucleic acid construct or expression vector of claim 1, wherein at least one control sequence is foreign to the polynucleotide.

3. The nucleic acid construct or expression vector of claim 1, wherein the polypeptide comprises the sequence of amino acids 1-426 of SEQ ID NO: 2.

4. A recombinant host cell comprising the nucleic acid construct of claim 1.

5. A recombinant host cell comprising the nucleic acid construct of claim 2.

6. A recombinant host cell comprising the nucleic acid construct of claim 3.

7. The recombinant host cell of claim 4, wherein the polypeptide is heterologous to the host cell.

8. The recombinant host cell of claim 5, wherein the polypeptide is heterologous to the host cell.

9. The recombinant host cell of claim 6, wherein the polypeptide is heterologous to the host cell.

10. The recombinant host cell of claim 7, which is a prokaryotic host cell selected from the group consisting of *Bacillus, Campylobacter, Clostridium, Enterococcus, E. coli, Flavobacterium, Fusobacterium Geobacillus, Helicobacter, Ilyobacter, Lactobacillus, Lactococcus, Neisseria, Oceanobacillus, Pseudomonas, Salmonella, Staphylococcus, Streptococcus, Streptomyces*, and *Ureaplasma* cells.

11. The recombinant host cell of claim 7, which is a fungal host cell.

12. The recombinant host cell of claim 11, which is a filamentous fungal host cell.

13. The recombinant host cell of claim 12, wherein the filamentous fungal host cell is selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, and *Trichoderma* cells.

14. The recombinant host cell of claim 13, wherein the filamentous fungal host cell is selected from the group consisting of *Aspergillus awamori, Aspergillus foetidus, Aspergillus fumigatus, Aspergillus japonicus, Aspergillus nidulans, Aspergillus niger*, and *Aspergillus oryzae* cells.

15. The recombinant host cell of claim 13, wherein the filamentous fungal host cell is selected from the group consisting of *Trichoderma harzianum, Trichoderma koningii, Trichoderma longibrachiatum, Trichoderma reesei*, and *Trichoderma viride* cells.

16. A method for producing a polypeptide having carboxypeptidase activity, comprising cultivating the host cell of claim 4 under conditions conducive for production of the polypeptide.

17. A method for producing a polypeptide having carboxypeptidase activity, comprising cultivating the host cell of claim 7 under conditions conducive for production of the polypeptide.

18. A method for producing a polypeptide having carboxypeptidase activity, comprising cultivating the host cell of claim 12 under conditions conducive for production of the polypeptide.

19. A method for producing a polypeptide having carboxypeptidase activity, comprising cultivating the host cell of claim 13 under conditions conducive for production of the polypeptide.

20. The method of claim 16, wherein the polypeptide has an activity of at least 0.15 on proline using Assay 1.

* * * * *